United States Patent
Morisset-Lopez et al.

(10) Patent No.: US 9,494,585 B2
(45) Date of Patent: Nov. 15, 2016

(54) TOOLS FOR THE IDENTIFICATION OF LINGO-1, LINGO-2, LINGO-3 AND LINGO-4 LIGANDS, AND USES THEREOF

(75) Inventors: Severine Morisset-Lopez, Saint-Pryve-Saint-Mesmin (FR); Helene Benedetti, Saint-Jean-de-Braye (FR)

(73) Assignee: CENTRE NATIONAL DE LA RECHERCHE SCIENTIFIQUE-CNRS, Paris (FR)

( * ) Notice: Subject to any disclaimer, the term of this patent is extended or adjusted under 35 U.S.C. 154(b) by 320 days.

(21) Appl. No.: 13/637,952

(22) PCT Filed: Apr. 1, 2011

(86) PCT No.: PCT/FR2011/050743
§ 371 (c)(1),
(2), (4) Date: Dec. 10, 2012

(87) PCT Pub. No.: WO2011/121257
PCT Pub. Date: Oct. 6, 2011

(65) Prior Publication Data
US 2013/0090249 A1 Apr. 11, 2013

(30) Foreign Application Priority Data
Apr. 1, 2010 (FR) ...................... 10 01374

(51) Int. Cl.
C40B 30/10 (2006.01)
G01N 33/566 (2006.01)
C07K 14/705 (2006.01)
C12Q 1/68 (2006.01)
G01N 33/542 (2006.01)

(52) U.S. Cl.
CPC ........... *G01N 33/566* (2013.01); *C07K 14/705* (2013.01); *C12Q 1/6897* (2013.01); *G01N 33/542* (2013.01); *C07K 2319/60* (2013.01); *C07K 2319/61* (2013.01); *C07K 2319/70* (2013.01); *G01N 2500/02* (2013.01)

(58) Field of Classification Search
None
See application file for complete search history.

(56) References Cited

U.S. PATENT DOCUMENTS

2007/0026463 A1 2/2007 Xie et al.
2007/0274918 A1* 11/2007 Mosyak et al. ................ 424/9.2
2009/0246189 A1 10/2009 Mi et al.

OTHER PUBLICATIONS

Mosyak L, et al. 2006 Journal of Biological Chemistry 281: 36378-36390.*
Zhang Z, et al. 2009 Journal of Biological Chemistry 284: 15717-15728.*
Dinant, C. et al 2008 Journal of Microscopy 231, Pt. 1: 97-104.*
Hamdan, F. et al 2006 Current Protocols in Neuroscience 5.23.1-5.23.20.*
Hoshino, H. et al 2007 Nature Methods 4: 637-639.*
Cobret et al 2015 British Journal of Pharmacology 172:841-56.*
Nyguyen et al (2005 Nature Biotechnology 23:355-60).*
Anonymous, Title: "LINGO1 (NM_032808) Human cDNA ORF Clone," XP-002600130, downloaded from URL http://www.origene.com/orf_clone/trueclone/NM_032808/RG203867/LINGO1.aspx on Sep. 9, 2010, pp. 1-2. Publisher: OriGene Technologies, Inc., Rockville, Maryland.
Anonymous, Title: "LINGO2 (NM_152570) Human cDNA ORF Clone," XP-002600131, downloaded from URL http://www.origene.com/orf_clone/search/retrieve_results.mspx?accn=NM152570&sku=RG214465 on Sep. 9, 2010, pp. 1-2. Publisher: OriGene Technologies, Inc., Rockville, Maryland.
Anonymous, Title: "LINGO3 (NM_001101391) Human cDNA ORF Clone," XP-002600132, downloaded from URL http://www.origene.com/orf_clone/trueclone/accession/NM_001101391/RG225998.aspx on Sep. 9, 2010, pp. 1-2. Publisher: OriGene Technologies, Inc., Rockville, Maryland.
Anonymous, Title: "LINGO4 (NM_001004432) Human cDNA ORF Clone," XP-002600133, downloaded from URL http://www.origene.com/orf_clone/trueclone/NM_001004432/RG215621/LINGO4.aspx on Sep. 9, 2010, pp. 1-2. Publisher: OriGene Technologies, Inc., Rockville, Maryland.

* cited by examiner

*Primary Examiner* — Christopher M Gross
(74) *Attorney, Agent, or Firm* — Arent Fox LLP

(57) ABSTRACT

The present invention relates to a system comprising coupling products formed by a monomer of a protein chosen from Lingo-1, Lingo-2, Lingo-3 and Lingo-4 and by a probe emitting a signal when said monomer undergoes conformational changes, and to a screening method using said system, enabling ligands of a protein chosen from Lingo-1, Lingo-2, Lingo-3 and Lingo-4 to be identified. The present invention is industrially applicable in the field of methods for detecting molecules, for detecting interaction between molecules and for molecular screening, and also in the medical field.

5 Claims, 9 Drawing Sheets a b a b a   HEK-293 cells expressing Lingo-1-RLuc b   HEK-293 cells expressing Lingo-YFP (clone Y1)

a b c

TOOLS FOR THE IDENTIFICATION OF LINGO-1, LINGO-2, LINGO-3 AND LINGO-4 LIGANDS, AND USES THEREOF

CROSS-REFERENCE TO RELATED APPLICATION

This Application is a National Stage entry of International Application No. PCT/FR2011/050743, having an international filing date of Apr. 1, 2011; which claims priority to French Application No.: 1001374, filed Apr. 1, 2010; the disclosure of each of which is hereby incorporated in its entirety by reference.

SEQUENCE LISTING

The instant application contains a Sequence Listing which has been submitted in ASCII format via EFS-Web and is hereby incorporated by reference in its entirety. Said ASCII copy, created on Nov. 21, 2012, is named 02130500.txt and is 101,368 bytes in size.

TECHNICAL FIELD

The present invention relates to a coupling product comprising a monomer of a protein chosen from Lingo-1, Lingo-2, Lingo-3 and Lingo-4 and a probe emitting a signal when said monomer undergoes conformational changes, to nucleic acid sequences encoding this product, to vectors enabling the preparation thereof, to a system comprising it and to a screening method which makes it possible to identify ligands of a protein chosen from Lingo-1, Lingo-2, Lingo-3 and Lingo-4.

The present invention is industrially applicable in the field of methods for detecting molecules, for detecting interaction between molecules and for molecular screening, and also in the medical field.

In the description below, the references between square brackets ([ ]) refer to the list of references given after the examples.

PRIOR ART

Neurodegenerative diseases are characterized by the degeneration of certain neurons and the destruction of the nervous system. Parkinson's disease and multiple sclerosis are two of these diseases.

Parkinson's disease affects 1 to 2 individuals in 1000. The degeneration involves dopaminergic neurons which produce a neurotransmitter, dopamine, which is involved in particular in the control of body movements. Apparently, the treatments developed against the disease, essentially dopaminergics and dopamine agonists, enable an improvement in the problems by slowing down the development of the disease. However, these treatments do not make it possible to cure the disease.

Multiple sclerosis is an autoimmune disease which has a prevalence of 1 in 1000 and in which the myelin of the axons of the brain and of the spinal cord is destroyed. This causes difficulties in conduction of nerve influx, thus affecting virtually all biological functions. The current treatments call upon immunosuppressants or immunomodulators. However, once again, these treatments only manage to slow down the progression of the disease and not to cure it.

One and the same protein, called Lingo-1, is at the intersection of these two diseases. Moreover, the Lingo-4 protein has a role in diseases involving myelin (WO 2009/061500). Lingo-1 is a transmembrane protein of 580 residues (without the signal peptide). It has a significant extracellular region (516 amino acids) consisting of 12 LRR (leucine-rich repeat) motifs and of an Ig (immunoglobulin) domain. The cytoplasmic portion, comprising 38 residues, contains a canonical site of phosphorylation by EGFR (Epidermal Growth Factor Receptor). Lingo-1 belongs to the family of LRR proteins which play key roles in the biology of the central nervous system (CNS) and constitute attractive targets for the treatment of neurological and neurodegenerative diseases.

The expression profile of Lingo-1 is nervous system-specific, with abundant expression in the CNS and more particularly in the neurons and the oligodendrocytes. This transmembrane protein exercises several inhibitory functions: that of neuron survival, that of axon and neurite regeneration after damage and that of oligodendrocyte maturation and of myelination.

Lingo-1 is a component of the NgR1/p75 complex and its inhibition promotes neurite and axon growth. Indeed, the gene encoding Lingo-1 was cloned in 2003 by Carim-Todd et al., ("LRRN6A/LERN1 (leucine-rich repeat neuronal protein 1), a novel gene with enriched expression in limbic system and neocortex". 2003, Eur. J; Neurosci. 18 (12): 3167-82, [1]) and it is in 2004 that Mi et al. (Mi et al., "LINGO-1 is a component of the Nogo-66 receptor/p75 signaling complex". 2004, Nat Neurosci. 7(3):221-8, [2]) showed that Lingo-1 was an integral part of the NgR1/p75 and NgR1/TROY receptor complex. These complexes, located in the membrane of neurons, inhibit neurite and axon regeneration in the presence of myelin constituents (OMGp, Nogo and MAG) via the activation of the RhoA kinase. This has been confirmed in an in vivo experimental model of axonal regeneration in rat. In this model, the spinal cord is injured and this is reflected by an increase in the expression of Lingo-1 and strong apoptosis of the oligodendrocytes and of the neurons surrounding the injury. Treatment of the injured rats with a Lingo-1 function antagonist, Lingo-1-Fc (a soluble form of Lingo-1 capable of competing with endogenous Lingo-1) makes it possible to obtain significant improvements in their mobility, sizeable regeneration of the axons and an increase in the survival of the neurons and oligodendrocytes around the injury (Ji et al., "LINGO-1 antagonist promotes functional recovery and axonal sprouting after spinal cord injury", 2006, Mol Cell Neurosci. 33(3):311-20, [3]).

Moreover, Lingo-1, expressed in the oligodendrocytes or the axons, inhibits oligodendrocyte differentiation and myelination (Mi et al., "Lingo-1 negatively regulates myelination by oligodendrocytes", 2005, Nature Neuroscience 8: 745-751, [4]). This has subsequently been confirmed by Lee et al. ("NGF regulates the expression of axonal LINGO-1 to inhibit oligodendrocyte differentiation and myelination". 2007, J Neurosci. 27(1):220-5, [5]) and Zhao et al. ("An in vitro study on the involvement of LINGO-1 and Rho GTPases in Nogo-A regulated differentiation of oligodendrocyte precursor cells", 2007, Mol Cell Neurosci. 36(2): 260-9, [6]). Indeed, although the use of Lingo-1 antagonists (Lingo-1-Fc, an anti-Lingo-1 antibody, DN-Lingo-1 (dominant negative) corresponding to Lingo-1 without its cytoplasmic domain, Lingo-1 RNAi, Lingo-1 knockout) induces increased differentiation of oligodendrocytes and the formation of abundant myelin sheets, the overproduction of whole Lingo-1 on the other hand causes opposite effects. Lee et al. (2007) ([5]) have, furthermore, shown that the expression of the Lingo-1 protein in the axons plays just as important a role in the differentiation of the adjacent oligodendrocytes and myelination as a Lingo-1 protein expressed in the oligodendrocytes. Lingo-1 expression in the axons is activated by NGF and its receptor, TrkA. In order to test the role that the inhibition of Lingo-1 might play in diseases affecting myelination, such as multiple sclerosis, an experimental animal model of the disease, called "MOG-induced murine experimental autoimmune encephalomyelitis" (EAE) has been tested. The use of an anti-Lingo-1 antibody (Lingo-1 antagonist) and of Lingo-1-knockout mice in this model has made it possible to demonstrate that decreased Lingo-1 function is associated with better axon integrity and increased remyelination thereof (Mi et al., "Lingo-1 antagonist promotes spinal cord remyelination and axonal integrity in MOG-induced experimental autoimmune encephalomyelitis", 2007, Nature medicine 13: 1228-1233, [7]).

Moreover, Lingo-1 inhibits the survival of dopaminergic (DA) neurons and of retinal ganglion cells (RGCs). Several studies carried out in animal models or cell cultures using Lingo-1 antagonists show that Lingo-1 plays an important role in neuronal survival and more particularly in the survival of retinal ganglion cells (RGCs) (destroyed in glaucoma) (Fu et al., "Blocking LINGO-1 function promotes retinal ganglion cell survival following ocular hypertension and optic nerve transection". Invest Ophthalmol Vis Sci. 2008, 49(3):975-85, [8]; Fu et al., "Combined effect of brain-derived neurotrophic factor and Lingo-1 fusion protein on long-term survival of retinal ganglion cells in chronic glaucoma", 2009, Neuroscience 162: 375-382, [9]), in cerebellar neurons (Zhao et al., "Inactivation of glycogen synthase kinase-3beta and up-regulation of LINGO-1 are involved in LINGO-1 antagonist regulated survival of cerebellar granular neurons", 2008, Cell Mol Neurobiol. 28(5): 727-35, [10]), and also in DA neurons (involved in Parkinson's disease) (Inoue et al., "Inhibition of the leucine-rich repeat protein Lingo-1 enhances survival, structure, and function of dopaminergic neurons in Parkinson's disease models", 2007, PNAS 104: 14430-14435, [11]). In the DA neurons of patients suffering from Parkinson's disease and in mouse experimental models, it appears that Lingo-1 is overproduced. Since Lingo-1 inhibits EGFR in these neurons, and since EGFR activates the PI3k/Akt pathway, the action of Lingo-1 on neuronal survival could come from an inhibition of the PI3k/Akt pathway.

In the animal model for glaucoma, it is known that BDNF (Brain-derived neurotrophic factor) is an important survival factor for RGCs which delays their death. Fu et al. (2009) ([9]) have recently established that the combined effect of Lingo-Fc and BDNF is much more effective than BDNF alone and allows increased long-term survival of RGCs. Since Lingo-1 is capable of interacting with the BDNF receptor, TrkB, and of inhibiting it, this molecular mechanism could be that involved in the long-term protection of RGCs.

The Lingo proteins, and in particular Lingo-1, constitute a new, particularly advantageous therapeutic target against these diseases, since inhibition thereof generates neuroprotective effects and stimulates myelin synthesis. Experiments carried out in vitro and in vivo on experimental animal models have validated the hypothesis that Lingo-1 inhibition is an innovative and promising approach for curing several nervous system diseases, in particular Parkinson's disease and multiple sclerosis.

The natural ligands of the Lingo proteins, and in particular of the Lingo-1 protein, are currently unknown. The identification of novel chemical molecules which are Lingo-1 antagonists would therefore make it possible to develop novel therapies against these two nervous system diseases.

However, no method which makes it possible to measure the binding of Lingo-1 ligands is currently available. Furthermore, no method of identification that can be automated and that can be adapted to the high-throughput of Lingo-1 ligands and antagonists currently exists. The only current means for identifying Lingo-1 ligands or antagonists are biological tests that are laborious to implement on cerebellar granular neurons (Mi et al., 2004, [2]; Zho at al., 2008, [10]), retinal ganglion cells (Fu et al., 2009, [9]), or oligodendrocytes (Mi et al., 2005, [4]) or in experimental murine models of autoimmune encephalomyelitis (Mi et al., 2007, [7]) or of Parkinson's disease (Inoue et al., 2007, [11]). These tests cannot be adapted to high-throughput.

For this reason, the applicant has sought to develop a method for identifying ligands, and in particular antagonists, of Lingo, and in particular Lingo-1, that can be automated and can be adapted to high-throughput.

DESCRIPTION OF THE INVENTION

The invention actually makes it possible to overcome the drawbacks of the prior art and to meet these needs.

The applicant has observed, surprisingly and after considerable research, that Lingo-1 forms a dimer in vivo. It was described in the literature that the extracellular part of Lingo-1 was capable of tetramerization (Mosyak et al., "The structure of Lingo-1 ectodomain, a module implicated in CNS repair inhibition", 2006, J. Biol. Chem. 281: 36378-36390, [12]). The applicant has shown, for the first time, that the whole and membrane form of Lingo-1 forms a dimer in vivo.

The applicant has thus developed a method for identifying a ligand of a protein chosen from Lingo-1, Lingo-2, Lingo-3 and Lingo-4, which can be easily automated and adapted to high-throughput, and which will make it possible to screen large libraries of chemical molecules in order to discover the most suitable inhibitors and exploit them for therapeutic purposes.

This method is based on the principle that, when Lingo, and in particular Lingo-1, interacts with a ligand, the conformation of the Lingo-1 dimer changes. The method of identification makes it possible to detect this conformational change and to identify Lingo-1 ligands.

The method of the invention comprises in particular the following steps:

a) incubating a system comprising coupling products formed by a monomer of a protein chosen from Lingo-1, Lingo-2, Lingo-3 and Lingo-4 and by a probe capable of emitting a detectable signal when said monomer undergoes conformational changes, and a candidate molecule, b) detecting a modification of the signal emitted by at least one of the probes, the modification of the signal revealing the binding of said candidate molecule to at least one of said coupling products.

The invention relates to a coupling product comprising a monomer of a protein chosen from Lingo-1, Lingo-2, Lingo-3 and Lingo-4, and a probe capable of emitting a signal when the monomer undergoes conformational changes.

For the purpose of the present invention, the term "monomer" means a protein composed of a single polypeptide molecule. In other words, it is a three-dimensional arrangement of atoms in a single polypeptide chain. Advantageously, the monomers are capable of forming dimers. In other words, the monomers are capable of associating with one another so as to form a molecule composed of two monomers, i.e. of two monomeric subunits. It may, for example, be a homodimer, i.e. two monomers of the same protein bonded to one another. Alternatively, it may be a heterodimer, i.e. two monomers of two different proteins bonded to one another. Advantageously, the dimer may be formed by polymerization of the monomers in vivo, under appropriate conditions. For example, these conditions may be suitable for the formation of disulfide bridges or to that of hydrophobic interactions.

For the purpose of the present invention, the term "Lingo-1, Lingo-2, Lingo-3 and Lingo-4" means any protein which has substantially the sequence of the wild-type protein. It may be a protein which has all or part of the wild-type protein, or a protein which has one or more mutations, for example by addition, deletion or substitution. It may be a human or non-human protein, for example a murine, equine, for example horse, porcine, rabbit, rat, ovine, for example sheep, bovine, for example cow, monkey, for example macaque, protein.

When the protein is Lingo-1, it may be the wild-type human protein, in particular composed of 580 residues, comprising an extracellular region (516 amino acids) consisting of 12 LRR (leucine-rich repeat) motifs and of an Ig (immunoglobulin) domain, and a cytoplasmic portion of 38 residues. Advantageously, the sequence of the Lingo-1 monomer may be the sequence SEQ ID No. 1. It may be the sequence described in Genbank (http://www.ncbi.nlm.nih.gov/Genbank/) by accession number NP_116197.4. It may also be the protein resulting from the polynucleotide sequence corresponding to the mRNA described by the sequence SEQ ID No. 5, or by the sequence NM_032808 in Genbank.

When the protein is Lingo-2, it may be the wild-type human protein, in particular composed of 606 amino acids, and comprising an extracellular domain composed of 515 amino acids, and a cytoplasmic portion of 40 residues. Advantageously, the sequence may be the sequence SEQ ID No. 2. It may be the sequence described in Genbank by accession number NP_689783.1. It may also be the protein resulting from the polynucleotide sequence corresponding to the mRNA described by the sequence SEQ ID No. 6, or by the sequence NM_152570 in Genbank.

When the protein is Lingo-3, it may be the wild-type human protein. Advantageously, the sequence may be the sequence SEQ ID No. 3. It may be the sequence described in Genbank by accession number NP_001094861. It may also be the protein resulting from the polynucleotide sequence corresponding to the mRNA described by the sequence SEQ ID No. 7, or by the sequence NM_001101391 in Genbank.

When the protein is Lingo-4, it may be the wild-type human protein, in particular composed of 593 amino acids. Advantageously, the sequence may be the sequence SEQ ID No. 4. It may also be the protein resulting from the polynucleotide sequence corresponding to the mRNA described by the sequence SEQ ID No. 8, or by the sequence NM_001004432 (human sequence), or the murine sequence NP 796224 in Genbank.

Advantageously, the interaction of the monomer or of the dimer with a ligand of the protein can cause a change in a physical characteristic of the monomer and/or of the dimer. It may, for example, be the spatial conformation of the monomer and/or dimer.

For the purpose of the present invention, the expression "conformational change in the monomer" means any spatial modification of the monomer. Advantageously, this modification may result from the interaction of the monomer and/or of the dimer with a ligand.

For the purpose of the present invention, the expression "probe capable of emitting a signal" means any molecule capable of producing an effect when a physical characteristic of the monomer undergoes a change, in particular when the monomer undergoes a conformational change. Advantageously, it may be a conformationally sensitive detectable label. Advantageously, the interaction of the ligand with the monomer or the dimer causes a conformational change in the monomer or in the dimer, this change involving the emission of a detectable signal.

Advantageously, the probe may be a molecule chosen from a chemical tag, for example an antibody, a luminescent molecule or a fluorescent molecule, a fragment integrated into the monomer, for example a protease cleavage site, or an immunodetectable fragment.

For the purpose of the present invention, the term "luminescent molecule" means any molecule which has the property of releasing, in the form of photons with an energy of nonthermal origin, a part of the energy absorbed during an excitation. It therefore involves the deactivation of an excited molecule toward a lower energy state. In other words, a luminescent molecule is a molecule capable of acting on an appropriate substance in order to generate luminescence.

The luminescent molecule may, for example, be a protein, or a chemical compound. Advantageously, the luminescent protein has the property of emitting a blue, yellow or green light. The protein may be chosen from those which are known to those skilled in the art, described for example in the documents Kamal et al., "Improved donor/acceptor BRET couples for monitoring beta-arrestin recruitment to G protein-coupled receptors". Biotechnol J. 2009 September; 4(9):1337-44, [17]; Kocan M et al., "Demonstration of improvements to the bioluminescence resonance energy transfer (BRET) technology for the monitoring of G protein-coupled receptors in live cells", J Biomol Screen. 2008 October; 13(9):888-98, [18]; Michelini E et al., "Luminescent probes and visualization of bioluminescence", Methods Mol Biol. 2009; 574:1-13, [19]). For example, the luminescent protein may be luciferase. The luciferase can be chosen from molecules known to those skilled in the art, for example those cited in WO 01/046691. It may, for example, be *Renilla* luciferase, RLuc2, RLuc8, firefly luciferase, *Gaussia* luciferase or Aequorin, and also mutants or derivatives thereof. If it is *Renilla* luciferase, it may be a protein encoded by the sequence SEQ ID No. 12.

For example, the luminescent protein may be *Renilla* luciferase, and the monomer may be Lingo-1. In this case, the coupling product can have the peptide sequence SEQ ID No. 14.

For the purpose of the present invention, the term "signal" means any physical or chemical effect. It may, for example, be a luminous signal, for example fluorescent, luminescent, colorimetric, electric, this list not being limiting.

For the purpose of the present invention, the term "fluorescent molecule" means any molecule which has the property of absorbing light energy (excitation light) and of rapidly releasing it in the form of fluorescent light, by emission of a photon very rapidly (emission light). Once the energy of the photon has been absorbed, the molecule is then generally in an electronically excited state. In other words, it may be a fluorophore or a fluorochrome.

Advantageously, the luminescent or fluorescent protein can be a protein capable of emitting a blue, yellow or green light.

Particularly advantageously, the luminescent or fluorescent protein can be a fluorescent protein capable of emitting a yellow or green light. The fluorescent protein can, for example, be chosen from GFP ("Green Fluorescent Protein"), YFP ("Yellow Fluorescent Protein"), Enhanced Yellow Fluorescent Protein (eYFP), eGFP, GFP2, GFP10, RGFP (*Renilla* Green Fluorescent Protein) and YPet, or mutants or derivatives thereof as described in document WO 01/46691. If it is eYFP, it can be a protein encoded by the sequence SEQ ID No. 9.

For example, the fluorescent protein may be eYFP, and the monomer may be Lingo-1. In this case, the coupling product can have the peptide sequence SEQ ID No. 11.

For the purpose of the present invention, the term "coupling product" means any product in which the monomer and the probe are bonded to one another. In other words, the coupling product can be a combination of the monomer and of the probe with one another. Again in other words, the coupling product can be a conjugate of the monomer and of the probe with one another.

Advantageously, the probe and the monomer can be coupled via one or more bonds that are stable in biological media. In other words, the probe and the monomer can be bonded via one or more bonds which do not alter at the time in the medium in which the coupling product is stored or produced. Advantageously, the medium can be a cell medium, or a medium used in the context of in vitro or in vivo operations.

The probe and the monomer can be covalently bonded. In this regard, the bond can be a bond between two atoms resulting from the sharing of two electrons originating separately from each of them.

The probe and the monomer can form a fusion protein, i.e. an artificial protein obtained through the combination of different proteins, or parts of proteins.

The coupling product can be obtained by means of techniques known to those skilled in the art, for example by expression by a host organism of a nucleic acid molecule encoding the coupling product, or by in vitro synthesis of the peptide and coupling after chemical ligation. For example, if it is a fusion protein, the coupling product can be obtained following the creation, by DNA recombination, of a gene comprising the open reading frames corresponding to the probe and to the monomer, insertion of the gene into an expression vector, insertion of the expression vector into a host cell, production of the corresponding fusion protein by the host cell and purification of the fusion protein.

The invention also relates to an isolated and purified nucleic acid molecule encoding a coupling product as previously defined.

For the purpose of the present invention, the term "nucleic acid molecule" means any molecule consisting of a series of nucleotides. It may, for example, be deoxyribonucleic acid (DNA), ribonucleic acid (RNA), messenger RNA (mRNA) or complementary DNA (cDNA).

For the purpose of the present invention, the term "isolated" means being separated from the natural environment. Advantageously, the nucleic acid can undergo the routine manipulations carried out in the context of recombinant DNA technology, for example sequencing, digestion with restriction enzymes, mutagenesis, and cloning into expression vectors.

For the purpose of the present invention, the term "purified" means the characteristic of being substantially separated from the contaminants.

The nucleic acid molecule can comprise a nucleic acid sequence encoding a luminescent or fluorescent protein as previously defined, and a nucleic acid sequence encoding a monomer as previously defined. Advantageously, the nucleic acid molecule can comprise the sequence SEQ ID No. 10 (the monomer being Lingo-1 and the protein being eYFP) or the sequence SEQ ID No. 13 (the monomer being Lingo-1 and the protein being *Renilla* luciferase).

The nucleic acid molecule can be obtained by means of techniques known to those skilled in the art. It can in particular be constructed artificially and obtained by chemical synthesis or genetic engineering, for example as described in Lewin B.: Genes VI, De Boeck University, 6th edition, Chapter 20, 1999. It can, for example, be obtained by recombination of the DNA of a gene comprising the open reading frames corresponding to the probe and to the monomer. By way of indication, the recombinant DNA can be inserted into a host expression organism, such as in particular a bacterium, by means of an expression vector, in particular a bacterial plasmid or a bacteriophage.

The invention also relates to an expression vector comprising a nucleic acid molecule as previously defined.

For the purpose of the present invention, the term "expression vector" means any molecule which has a structure that allows a nucleic acid molecule having a coding sequence to be transcribed or translated into a protein. Advantageously, it can comprise at least one of the following sequences: a promoter, a transcription start sequence, a transcription stop sequence, such as a polyadenylation sequence, a selectable gene, an enhancer, a regulatory sequence and an inducible sequence.

The vector can be any vector known to those skilled in the art, for instance a virus, such as an adenovirus or a retrovirus, a plasmid, a bacteriophage, a cosmid or a phagemid. It can, for example, be a commercially available vector, such as the plasmids p3xFlag (Sigma), pcDNA$_3$ (Invitrogen) or peYFP-N1 (Clontech).

Such a vector can be prepared according to techniques known to those skilled in the art, as described for example by Lewin B.: Genes VI, De Boeck University, 6th edition, Chapter 20, 1999.

The invention also relates to a host cell comprising at least one nucleic acid molecule as previously defined or an expression vector as previously defined.

For the purpose of the present invention, the term "host cell" means any organism which has the capacity to produce a protein when an expression vector encoding the protein is introduced therein. Advantageously, the host cell can express the coupling product when an expression vector encoding the coupling product is introduced therein.

Advantageously, the host cell can express at least one coupling product as previously defined. For example, the host cell can express a coupling product comprising *Renilla* luciferase and Lingo-1, or a coupling product comprising eYFP and Lingo-1.

Advantageously, the host cell can comprise two nucleic acid molecules or an expression vector. For example, the host cell can comprise and express a nucleic acid molecule encoding a coupling product comprising a luminescent protein and a monomer, and a nucleic acid molecule encoding a coupling product comprising a fluorescent protein and a monomer. For example, the host cell can comprise and express a nucleic acid molecule encoding a coupling product comprising *Renilla* luciferase and a Lingo-1 monomer, and a nucleic acid molecule encoding a coupling product comprising eYFP and a Lingo-1 monomer.

Advantageously, the coupling products can form dimers in the host cell. This is because the applicant has shown that, in vivo, the monomers expressed in the cells form dimers.

The host cell can be any organism suitable for the production of recombinant proteins that is known to those skilled in the art. It may be a eukaryotic or prokaryotic cell. For example, it may be YB2/0 (ATCC CRL-1662), CHO-K1 (ATCC CCL-61), for example HEK 293 (ATCC CRL-1573), BHK (ATCC CRL-12072) or COS (ATCC CRL-1650), PC12 (ATCC CRL-1721) or SH-SY5Y (ATCC CRL-2266) or Hela (ATCC CCL-2).

The host cell can be produced by insertion of an expression vector as previously defined or of a nucleic acid molecule as previously defined, into the host cell, by means of techniques known to those skilled in the art. Mention may be made, for example, of electroporation, or calcium phosphate, described in the document "Molecular Cloning: A Laboratory Manual 2nd edition" (1989), Cold Spring Harbor Laboratory Press, "Current Protocols in Molecular Biology" (1987), John Wiley & Sons, Inc. ISBNO-471-50338-X, and the like, an electroporation method described in "Methods in Electroporation: Gene Pulser/*E. coli* Pulser System" Bio-Rad Laboratories (1993).

The host cell can be cultured in any suitable medium known to those skilled in the art. Mention may be made, for example, of DMEM medium (Dulbecco's Modified Eagle Medium, Invitrogen™), Ham's F-12 medium, Eagle's Minimum Essential Medium (MEM), and Neuronal Base Medium (PAA Laboratories).

The coupling product can be purified by any means known to those skilled in the art, for example by immunopurification or by affinity chromatography.

A first subject of the invention relates to a system comprising:

a) a first coupling product comprising a monomer of a protein chosen from Lingo-1, Lingo-2, Lingo-3 and Lingo-4, and a probe capable of emitting a detectable signal which is modified when the monomer undergoes conformational changes, as previously defined, b) a second coupling product comprising a monomer of a protein chosen from Lingo-1, Lingo-2, Lingo-3 and Lingo-4, and a probe capable of emitting a detectable signal which is modified when the monomer undergoes conformational changes, as previously defined, wherein the first coupling product and the second coupling product form a dimer, and in which a change in interaction between the monomers causes a change in signal.

For the purpose of the present invention, the term "system" means a dimer (i.e. a complex of proteins made of two subunits very close to one another owing to the intermolecular interaction) resulting from couplings formed by a monomer of a protein chosen from Lingo-1, Lingo-2, Lingo-3 and Lingo-4 and by a probe capable of emitting a signal which is detectable, said signal being modified when said monomer and/or dimer undergo conformational changes, by any suitable technique known to those skilled in the art, for example a system suitable for detection by bioluminescence resonance energy transfer (BRET), by fluorescence resonance energy transfer (FRET), by TR-FRET (time-resolved-FRET) or by HTRF (homogeneous time resolved fluorescence). Preferably, it is a system of detection by bioluminescence resonance energy transfer (BRET). Said system of the invention can be in the form of a cell suspension, of a culture of adherent cells, of membranes or tissues, etc., expressing the donor/acceptor couple.

For the purpose of the present invention, the term "dimer" means any molecule composed of two monomers. Advantageously, the distance between the monomers making up the dimer is less than 150 Å, for example less than 100 Å, advantageously less than 75 Å or 50 Å.

For the purpose of the invention, the term "change in interaction" means any physical or structural modification between the monomers. It may in particular be a spatial or conformational modification of the monomers. Advantageously, this change can result from the binding of a ligand to the dimer or to at least one of the monomers, or from the proximity of a ligand on the dimer or at least one of the monomers.

For the purpose of the present invention, the term "ligand" means any molecule which binds to the coupling product. Advantageously, this binding can take place when the coupling product is in dimer form. The ligand can be a hormone, a neurotransmitter, a chemical compound, a medicament, a diagnostic agent, an antibody or a peptide sequence. It can be a total or partial agonist or a total or partial antagonist. Advantageously, a ligand can be capable of binding a monomer or a dimer with an affinity of between 1 µM and 1 pM, preferentially between 1 nM and 1 pM. Advantageously, the ligands can treat or prevent Parkinson's disease or multiple sclerosis, glaucomas or diseases involving myelin.

The applicant has in fact shown, firstly, that the coupling product, and more particularly the monomer, dimerizes, in particular in vivo, and secondly, that the binding of the ligand to the dimer can cause a conformational change in the dimer.

Advantageously, the conformational change causes a change in emission of a signal by a probe. Advantageously, the signal can be detected by any suitable technique known to those skilled in the art. Advantageously, the system can be suitable for detection by bioluminescence resonance energy transfer (BRET), a fluorescence resonance energy transfer (FRET) system, TR-FRET (time-resolved-FRET) or HTRF (homogeneous time resolved fluorescence).

For example, the system of the invention can be implemented in the context of detection by BRET, according to a protocol known to those skilled in the art. Mention may be made, for example, of Xu et al., "A bioluminescence resonance energy transfer (BRET) system: application to interacting circadian clock proteins" (1999) Proc. Natl. Acad. Sci. USA. 96, 151-156 [13]; Angers et al., "Detection of beta 2-adrenergic receptor dimerization in living cells using bioluminescence resonance energy transfer (BRET)" (2000) Proc. Natl. Acad. Sci. USA 97: 3684-3689 [14]). In particular, BRET can be implemented by means of a coupling product comprising Rluc and Lingo-1, and a coupling product comprising eYFP and Lingo-1. Rluc is an enzyme which produces blue light in the presence of a substrate, for example coelenterazine or a commercially available derivative thereof (Molecular Probes Eugene Oreg., Biosynth Napierville Ill.). When the spatial orientation is appropriate, eYFP is capable of absorbing a portion of blue light and emits as a consequence a light with a different wavelength, in the yellow range. In other words, in the presence of coelenterazine, eYFP emits a yellow light if Rluc and eYFP are sufficiently close to one another. For the purpose of the present invention, the term "sufficiently close" means at a distance of less than 150 Å, or else less than 100 Å, and advantageously less than 75 Å or 50 Å. If Rluc and eYFP are too far apart, the energy is not efficiently transferred and only the blue light of Rluc is detected. It so happens that the spatial disposition of Rluc and eYFP with respect to one another is dependent on the spatial arrangement of the monomers with respect to one another. If a molecule binds to a monomer or to the dimer, then the spatial conformation of the dimer changes. In particular, the monomers move close together or further apart. When the two monomers, and in particular Rluc and eYFP, are sufficiently close, eYFP can absorb a portion of the blue light emitted by Rluc, and can emit a wavelength in the yellow range. Thus, in order to detect whether a molecule binds to the dimer or to the monomer, the efficiency of the energy transfer is determined by measuring the luminous efficiency at the wavelength of the donor (Rluc) and at the wavelength of the acceptor (eYFP) after addition of coelenterazine. Moreover, the "luminous efficiency of the acceptor/luminous efficiency of the donor" ratio is calculated in order to quantify the BRET.

Alternatively, the system of the invention can be implemented in the context of detection by FRET, according to a protocol known to those skilled in the art. Mention may, for example, be made of U.S. Pat. No. 7,183,066, (Kroeger et al., "Constitutive and agonist-dependent homo-oligomerization of the thyrotropin-releasing hormone receptor" (2001) J Biol Chem, 276, 12736-12743, [20]). For example, a donor fluorophore and an acceptor chromophore known to those skilled in the art can be used, for example by means of the fluorescein/rhodamine or CFP (cyan fluorescent protein)/YFP couples.

Advantageously, the system of the invention can be implemented in the context of detection by TR-FRET, according to a protocol known to those skilled in the art, for example described in Maurel D et al., "Cell-surface protein-protein interaction analysis with time-resolved FRET and snap-tag technologies: application to GPCR oligomerization" (2008), Nat Methods (6):561-7, [21]). For example, it is possible to improve the signal-to-noise of the FRET by dispensing with a part of the parasitic signals by virtue of a time-resolved reading. This is possible through the use of long-life fluorophores such as rare earth cryptates or chelates.

Advantageously, the system of the invention can be implemented in the context of detection by HTRF®, according to a protocol known to those skilled in the art, for instance that of Hermand P et al., "Functional adhesiveness of the CX3CL1 chemokine requires its aggregation. Role of the transmembrane domain" (2008) J Biol Chem 283(44):30225-34; ([22]), or Whitfield J et al., "High-throughput methods to detect dimerization of Bcl-2 family proteins" (2003), Anal Biochem, 322(2):170-8 ([23]). For example, antibodies labeled with a fluorescence donor such as europium cryptate or a fluorescence acceptor such as a pigment of a phycobiliprotein purified from a red alga (for example, XL665) recognize tags on each of the monomers. The interaction of the monomers is detected by energy transfer, for example by excitation at 337 nm and emission at 665 nm. The system can be obtained by cotransfection of a cell with two expression vectors as previously defined. The system can, for example, be implemented in vitro, for example on plates.

Another subject of the invention relates to the use of a system as previously defined, for identifying ligands of a protein chosen from Lingo-1, Lingo-2, Lingo-3 and Lingo-4.

Another subject of the invention relates to the use of a system as previously defined, for detecting conformational changes in a protein chosen from Lingo-1, Lingo-2, Lingo-3 and Lingo-4.

Another subject of the invention relates to a method for identifying a ligand of a protein chosen from Lingo-1, Lingo-2, Lingo-3 and Lingo-4, comprising the following steps:

a) incubating a system as previously defined and a candidate molecule, said system comprising:

(i) a first coupling product comprising a monomer of a protein chosen from Lingo-1, Lingo-2, Lingo-3 and Lingo-4, and a probe capable of emitting a detectable signal which is modified when said monomer undergoes conformational changes, (ii) a second coupling product comprising a monomer of a protein chosen from Lingo-1, Lingo-2, Lingo-3 and Lingo-4, and a probe capable of emitting a detectable signal which is modified when said monomer undergoes conformational changes, b) detecting a signal emitted by at least one of the probes, the signal revealing the binding of said candidate molecule to at least one of the coupling products.

For the purpose of the present invention, the term "incubating" means bringing together the first coupling product, the second coupling product and the candidate molecule. Advantageously, the incubation is carried out under conditions which allow the dimerization of the monomers of the first and second coupling products. Advantageously, the incubation is carried out under known conditions which allow the binding of the candidate molecule to at least one of the monomers or to the dimer, if the candidate molecule is a ligand of the protein. The term "candidate molecule" means any test molecule. It may be, for example, a protein, a peptide, a chemical molecule, an antibody, this list not being limiting. The molecule can, for example, be derived from a protein library, a cell suspension, a chemical library, this list not being limiting. The molecule can be a ligand of Lingo-1, Lingo-2, Lingo-3 or Lingo-4.

Advantageously, when the candidate molecule is not a ligand of the protein, the BRET signal, resulting from the formation of the dimer, is not modified following the addition of the candidate molecule. Advantageously, there is, in this case, no modification of a physical property of the monomers, of the dimer, of the probes or of the coupling products.

Advantageously, the variations in the BRET signal after the addition of a ligand may be monitored over time, for 30 minutes for example.

Advantageously, when the candidate molecule is a ligand of the protein, the BRET signal, resulting from the formation of the dimer, is modified, for example increased or decreased, following the addition of the candidate molecule. Advantageously, there is, in this case, a modification of at least one physical property of at least one monomer, of the dimer, of the probes or of the coupling products. Advantageously, the binding of the candidate molecule causes a conformational modification of at least one monomer, of the dimer, of the probes or of the coupling products.

Advantageously, the signal can be detected in the context of a BRET, FRET, TR-FRET or HTRF system.

Advantageously, the method of the invention can also comprise a step of adding a substrate which makes it possible for the signal to occur. It may, for example, be coelenterazine or a coelenterazine derivative, for example coelenterazine 400a, or DeepBlueC. The substrate can be added in any way known to those skilled in the art, for example exogenously, or added in the form of a nucleic acid encoding the substrate.

Advantageously, the method can comprise any step or condition required for implementing a BRET, FRET, TR-FRET or HTRF process. These steps are well known to those skilled in the art, and can comprise a step of measuring the signal, of calculating the emission and absorption wavelengths, of using filters in order to distinguish the wavelengths, of calculating the wavelength intensity by means, for example, of a photomultiplier tube or of a CDD (Charged Coupled Device) camera, of calculating energy transfer efficiency, of detecting the emission peaks, and of using instruments such as BRETCount, Mithras (Berthold), microplate scintillation and luminescence counters (Berthold, Packard Instruments).

The method can be implemented in vitro or in vivo. Advantageously, the method can be implemented on live cells. For example, the method can be implemented with stably or transiently transfected cell lines, under physiological conditions.

Advantageously, the method can be implemented on preparations of membranes, optionally prepared in advance and frozen, or on purified proteins.

Advantageously, the method can also comprise a high-throughput screening system. For the purpose of the present invention, the term "high-throughput screening system" means any means of automation which makes it possible to accelerate the identification method. It may be any means known to those skilled in the art, involving, for example, information technology, bioinformatics, genomics, proteomics, robotics, and sometimes nanotechnologies, this list not being limiting.

Advantageously, the method can also comprise a test which makes it possible to identify the agonist (activator) ligands and the antagonist (inhibitor) ligands of the proteins. It may, for example, be a biological test. It may be any test which makes it possible to identify the impact of a candidate molecule on at least one signaling pathway in which the protein plays a role, for example oligodendrocyte differentiation, as implemented, for example, in Mi et al., 2005, ([4]), axonal myelination, or the survival of dopaminergic neurons and of retinal ganglion cells, as implemented, for example, in Fu et al., 2009, ([9]).

Advantageously, the method can make it possible to determine whether, downstream, cell signaling pathways involving the RhoA or Akt protein kinases are activated or inhibited by the ligand. The effect of the ligands can, for example, be tested on the Rho pathway (RhoA test sold by Pierce) or on the Akt pathway (test using AlphaScreen from Perkin or by Western blotting analysis using specific antibodies from Cell Signaling).

Advantageously, the method can make it possible to determine whether ligands disrupt the interaction between the protein and the membrane receptors NgR1, EGFR and TrkB. In this regard, the interaction between Lingo-1 and NgR, Lingo-1-EGFR and Lingo-1/TrkB can be measured.

The invention also relates to a device, also called kit, for implementing the method as defined above, which can make it possible to study at least one interaction described above. The kit can comprise all or a part of the elements required for implementing the method, for example the coupling products, substrates, at least one means for detecting or measuring the BRET signal, this list not being limiting. The kit can, for example, contain the plasmids of the fusion proteins, for example Lingo-1-RLuc, Lingo-1-YFP, Lingo-2-RLuc, Lingo-2-YFP, Lingo-3-RLuc, Lingo-3-YFP, Lingo-4-RLuc, Lingo-4-YFP, NgR-RLuc, NgR-YFP, EGFR-RLuc, EGFR-YFP, TrkB-RLuc and TrkB-YFP, and also a substrate, for example coelenterazine.

RLuc/Lingo-3-YFP (triangles) and Lingo-4-RLuc/Lingo-4-YFP (diamonds). (b) The BRET signal is measured (mBU) for Lingo-1-RLuc/Lingo-1-YFP. The BRET measurement is carried out 48 hours after transfection on the live cells. The BRET ratio was calculated with a set of filters, using the 540±40 nm filter for the light emitted by eYFP and the 480±20 nm filter for the light emitted by RLuc.

Figure 7:
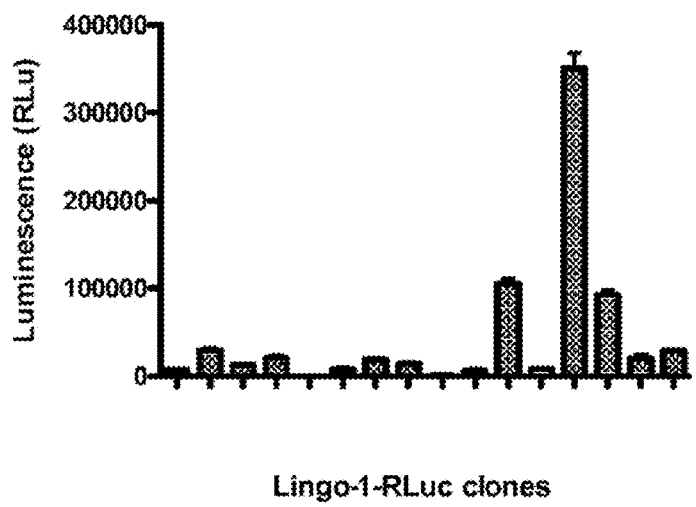

FIG. 7 represents stable HEK-293 cell lines expressing hLingo-1-RLuc or hLingo-1-YFP.

Figure 8:
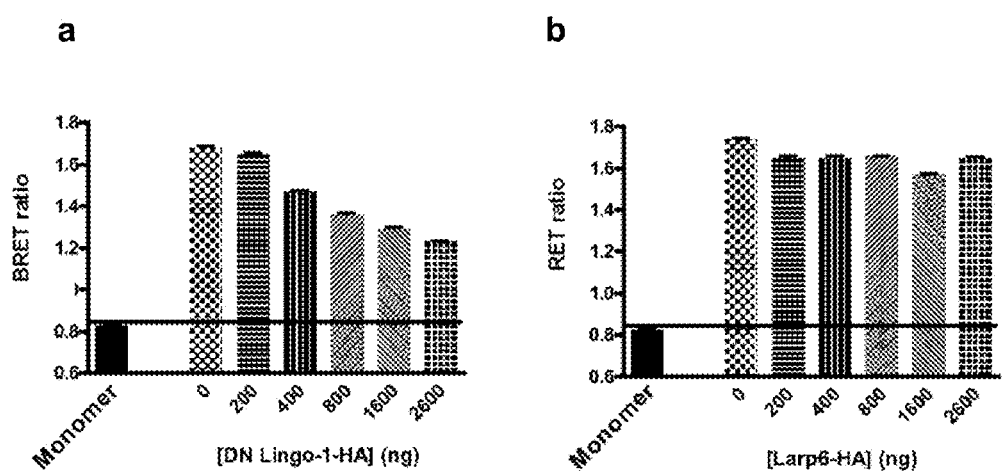

FIG. 8 represents the validation and the specificity of the screening test using the system of the invention with a known inhibitor of Lingo-1 (DN-Lingo-1).

Figure 9:
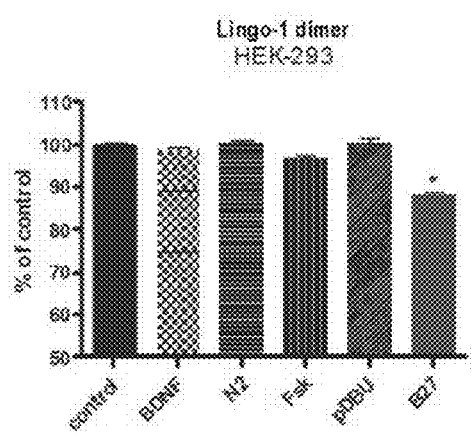
Figure 9:
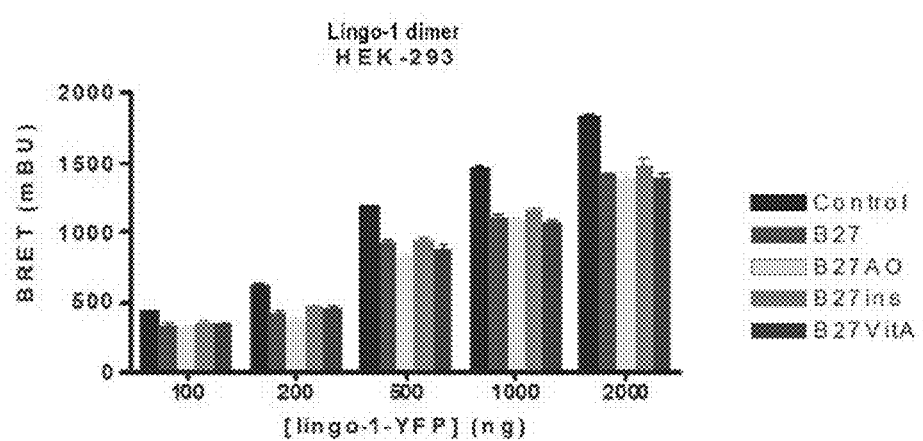
Figure 9:
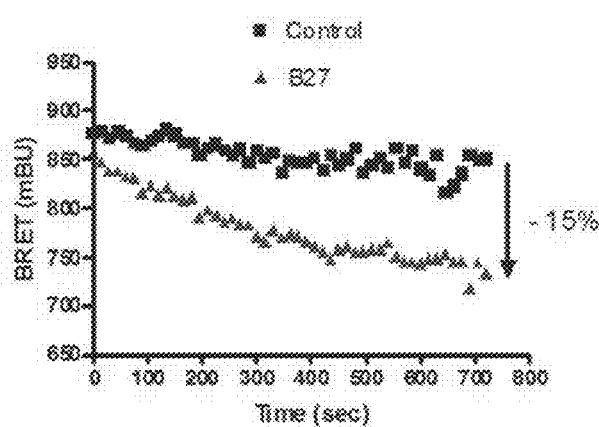

FIG. 9 represents (a, b) the identification and the validation of potential ligands of Lingo-1 (dimerization inhibitors) using the system of the invention, (c) the kinetics of the effect of the specific ligand B27 thus identified.

Figure 10:
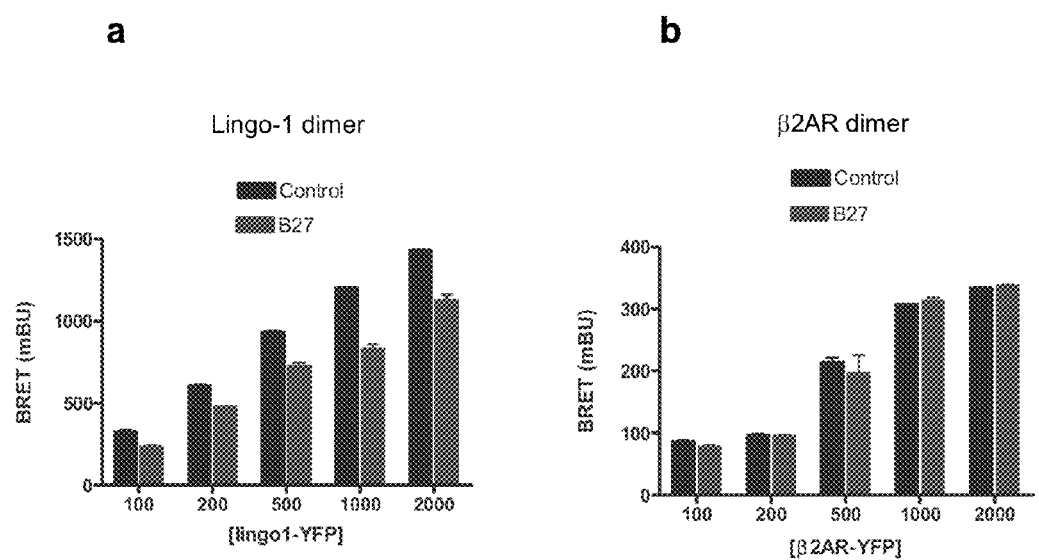

FIG. 10 represents the study of the specificity of B27 in a counter-screening test (study of the signal originating from the dimerization of the (β2 adrenergic receptor, (β2AR).

EXAMPLES

Materials and Methods

1. Cells

The HEK-293 (human embryonic kidney fibroblasts, ATCC CRL-1573) and SH-SY5Y (human neuroblastomas, ATCC CRL-2266) cell lines are cultured in a DMEM medium (Dulbecco's Modified Eagle Medium) supplemented with fetal calf serum (10%, BioWest, France), penicillin (100 U/ml, Eurobio), streptomycin (100 µg/ml, Eurobio, France) and L-glutamine (2 mM, Eurobio). The primary neuron cultures are prepared from the cortex of rat embryos taken at E18 (embryonic day 18). The neurons are cultured in Neurobasal™ (Gibco®, Invitrogen, composed of glycine, L-alanine, L-arginine hydrochloride, L-asparagine-$H_2O$, L-cysteine, L-histidine hydrochloride-$H_2O$, L-isoleucine, L-leucine, L-lysine hydrochloride, L-methionine, L-phenylalanine, L-proline, L-serine, L-threonine, L-tryptophan, L-tyrosine, L-valine, choline chloride, D-calcium pantothenate, folic acid, niacinamide, pyridoxine hydrochloride, riboflavin, thiamine hydrochloride, vitamin B12, i-inositol, calcium chloride, ferric nitrate, magnesium chloride, potassium chloride, sodium bicarbonate, sodium chloride, monobasic sodium phosphate, zinc sulfate, HEPES, phenol red) supplemented with B27 (composed in particular of d-biotin, bovine serum albumin, free of fatty acid, catalase, L-carnitine HCl, corticosterone, ethanolamine HCl, D-galactose, glutathione, insulin, linoleic acid, linolenic acid, progesterone, putrescine.2HCl, sodium selenite, superoxide dismutase, T-3/albumin, DL-alpha-tocopherol, DL-alpha-tocopherol acetate, transferrin, vitamin A acetate, Gibco®), penicillin (100 U/ml) and streptomycin (100 µg/ml). The cells are cultured in incubators at 37° C. under a humid atmosphere, at 5% $CO_2$.

2. Construction of the Expression Vectors:

Five expression vectors were used: Lingo-1-HA: the sequence encoding the human Lingo-1 protein (620 amino acids, accession number NP_116197) followed by a hemagglutinin epitope tag (HA) was amplified by PCR (for "Polymerase Chain Reaction"). The fragment obtained was introduced into the pcDNA₃ plasmid (Invitrogen). The Lingo-1-HA plasmid has the sequence SEQ ID No. 19.

DN-Lingo-1-HA: the sequence encoding the extracellular part of Lingo and also its transmembrane domain (amino acids 1-577), followed by a hemagglutinin epitope tag (HA), was amplified by PCR. The fragment obtained was introduced into the pcDNA₃ plasmid (supplied by Invitrogen, 5446 bp in size, containing in particular a cytomegalovirus promoter, a T7 sequencing primer, an ampicillin resistance gene and the neomycin selection gene).

Lingo-1-RLuc: contains the sequence encoding the whole human Lingo-1 protein (620 amino acids) 3' tagged with the sequence of a luminescence label (*Renilla luciformis*). The Lingo-1-RLuc plasmid has the sequence SEQ ID No. 17.

Lingo-1-eYFP: contains the sequence encoding the whole human Lingo-1 protein (620 amino acids) 3' tagged with the sequence of a yellow fluorescence label (eYFP: enhanced yellow fluorescent protein), the physical characteristics of which, in particular its fluorescence intensity, have been improved compared with YFP. The Lingo-1-eYFP plasmid has the sequence SEQ ID No. 18.

pRLuc-N1: contains the coding sequence of *Renilla* luciferase (RLuc) downstream of a multiple cloning site. This plasmid was constructed from the commercially available plasmid pEYFP-N1 by removing the sequence of eYFP and replacing it with the sequence of RLuc. The pRLuc-N1 plasmid has the sequence SEQ ID No. 15.

The Lingo-1-RLuc and Lingo-1-eYFP fusion proteins were obtained by conventional subcloning techniques (digestion of DNA fragments or plasmids with the restriction enzymes Sal I, BamH I, NotI, Hind III, EcoR I, Nhe I; ligation of DNA fragments in a plasmid; transformation of DH5α competent bacteria, Invitrogen), using a commercially available expression vector (peYFP-N1, Clonetech) or an expression vector available in the laboratory (pRLuc-N1) having multiple cloning sites adjacent to the coding sequences for *Renilla* luciferase (Rluc) or the eYFP fluorescent protein.

The Lingo-1-Rluc and Lingo-1-eYFP fusion proteins were obtained by fusing RLuc and eYFP to the C-terminal end of the human form of Lingo (620 amino acids, accession number NP_116197). The sequence of Lingo-1 devoid of its stop codon was amplified by PCR. The fragment obtained was introduced into the peYFP-N1 plasmid (supplied by Clontech, of sequence SEQ ID No. 16), approximately 4700 bp in size, containing in particular a CMV promoter, an EGFP-N sequencing primer of sequence 5'd[CGTCGC-CGTCCAGCTCGACCAG]3' (SEQ ID NO: 20), a kanamycin resistance gene, a neomycin resistance gene for selection (with G418 or geneticin) of mammalian cells, in order to obtain the construct Lingo-1-eYFP, or into the pRLuc-N1 plasmid in order to obtain the construct Lingo-1-Rluc.

3. Transfection of the Constructs

Figure 1:
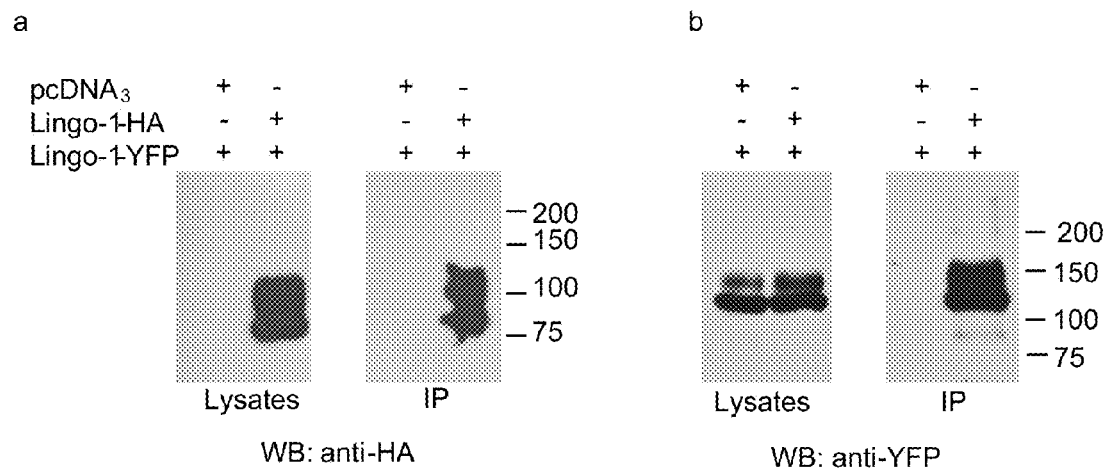
FIG. 1 represents coimmunoprecipitation experiments showing that Lingo-1 forms a dimer in HEK-293 cells. The HEK-293 cells are cotransfected (+ sign) with 5 μg of the pcDNA3, Lingo-1-HA or Lingo-1-YFP plasmids. A coimmunoprecipitation is carried out with agarose beads coupled to an anti-HA antibody (cf. part a, showing the anti-HA Western Blot or WB) or an anti-YFP antibody (cf. part b, showing the anti-YFP Western Blot or WB). The incubation of the corresponding membrane with an anti-HA antibody shows that the Lingo-HA protein has indeed been immunoprecipitated (a). Two immunoreactive bands appear specifically at approximately 120 kDa and 140 kDa and attest to the presence of Lingo-YFP in the immunoprecipitate (b).

For the Western Blot and coimmunoprecipitation experiments (FIG. 1), the HEK-293 cells are transfected using a transfection lipid: Lipofectamine™ LTX (Invitrogen™).

The day before the transfection, the cells are distributed, in their culture medium without antibiotics, onto collagen-coated dishes (collagen type I, Serva).

The HEK-293 cells are cotransfected with 5 µg of various plasmids. Two days after transfection, the cells are lysed in a buffer containing 0.5% of triton X100. On the day of the transfection, the plasmid DNA (5 to 10 µg) diluted in Optimem medium (3 ml, Cat No. 31985-047 Gibco®, Invitrogen, composed in particular of L-glutamine, 2400 mg/L of sodium bicarbonate, HEPES, sodium pyruvate, hypoxanthine, thymidine, growth factors, mg/L phenol red) is incubated for 5 minutes in the presence of Plus Reagent™ (10 µl, Cat No. 11514015, Invitrogen™). The lipofectamine LTX (20 µl, Cat No. 15338-500, Invitrogen™) is then added to the mixture and incubated for 30 minutes. After the medium has been changed (7 ml/dish), the complex formed by the DNA and the lipofectamine is added dropwise to the cells. In order to avoid a toxic effect of the lipofectamine, the transfection medium is drawn off after 5 hours and it is replaced with fresh medium without antibiotics.

For the BRET experiments, the HEK-293 cells cultured in 6-well plates, pre-treated with collagen, are transiently transfected using the calcium phosphate technique. Briefly, the plasmid DNA is mixed into a phosphate buffer (2×BBS, composed in particular of 50 mM BES (Cat No. B4554, Sigma), 280 mM NaCl, 1.5 mM $Na_2HPO_4$, adjusted to pH 6.95) with calcium chloride (2.5 M). After incubation for 15 minutes, the precipitate obtained is applied to the cells for 24 hours. The cells are then rinsed and incubated for a further 24 hours in a culture medium without antibiotics.

For the BRET experiments, the SH-SY5Y cells cultured in 6-well plates, pre-treated with collagen, are transiently transfected using a transfection lipid: lipofectamine 2000 (Cat No. 11668019, Invitrogen™). On the day of the transfection, the plasmid DNA diluted in Optimem medium (500 µl) is mixed with the lipofectamine 2000 (5 µl) and then incubated for 20 minutes. After the medium has been changed (2 ml of fresh medium without antibiotics, per well), the complex is applied to the cells for 24 hours. The cells are then rinsed and incubated for a further 24 hours in the culture medium without antibiotics.

4. Preparation of the Lysates, Chemical Bridging, Western Blotting

When chemical bridging is carried out, it is performed on the live cells before lysis. After having rinsed the cells with PBS, the cells are incubated with DSP (Lomant's Reagent, dithiobis[succinimidyl propionate], Cat No. 22585, Thermo Scientific) (160 µg/ml, diluted in an HBSS buffer) for 10 minutes at ambient temperature. After three rinses with PBS ("phosphate buffered saline"), the cells are then lysed. The lysis is carried out on ice. After three rinses with cold PBS, the cells are incubated in the lysis buffer for 10 minutes (50 mM Tris/HCl, pH 7.5, Triton X100 from 0.5 to 1% depending on the experiments, 100 mM NaCl, 50 mM NaF, 5 mM EDTA, 10 µg/ml of aprotinin, 10 mM sodium pyrophosphate), to which a cocktail of protease and phosphatase inhibitors is added. The cells are then recovered using a scraper and then centrifuged (15 minutes at 22 000 g at 4° C.). The supernatant is stored at −20° C., loaded onto a gel or used directly for the coimmunoprecipitation experiments. To do this, a fixed amount of the cell lysate is incubated with the beads of agarose coupled to the anti-HA antibody (40 µl of beads, EZview, Sigma), at 4° C., on a wheel overnight. After 5 successive washes with the lysis buffer, the immunoprecipitate is recovered by adding 40 µl of 4× Laemmli buffer (200 mM Tris, pH 6.8, 4% SDS, 40% glycerol, 0.5 mM β-mercaptoethanol, 0.02% bromophenol blue). The cell lysates and the immunoprecipitates are then loaded onto an 8% acrylamide gel under denaturing and reducing conditions. The electrophoresis is carried out in a Tris/glycine migration buffer, and then the proteins are transferred onto a PVDF Hybond-P membrane (Amersham Biosciences). The membrane is saturated in a solution of TBS-T (0.1% Tween 20)-5% skimmed milk for 1 hour. The primary antibodies are incubated in the same solution for 2 hours at ambient temperature: anti-Lingo (antibodies directed against amino acids 40 to 556 of the Lingo-1 sequence; accession number AAH11057, Cat No. AF3086, R &D Systems) at $1/1000^{th}$, anti-HA (Roche, rat) at $1/5000^{th}$, Living Colors® antibody (Clontech) at $1/5000^{th}$. Several washes in TBS-T (Tris buffered saline—0.1% Tween 20) are carried out before incubating the membrane with the corresponding secondary antibodies coupled to peroxydase at a $1/33000^{th}$ dilution in TBS-T (0.1% Tween 20)—5% skimmed milk for 1 hour. Once again, after several washes, the membrane is incubated with the substrate (SuperSignal West Dura, Pierce) for 5 minutes before exposure on film (CL-Xposure, Amersham Biosciences).

5. Measurement of BRET, Luminescence and Fluorescence

The cells are resuspended in a physiological buffer (HBSS for *Hank's Buffered Salt Solution* (Cat No. 14025100, Gibco, composed in particular of calcium chloride, magnesium chloride, magnesium sulfate, potassium chloride, monobasic potassium phosphate, sodium bicarbonate, sodium chloride, anhydrous dibasic sodium phosphate)) 48 hours after transfection and distributed into 96-well plates (100 000 to 200 000 cells per well) or into 384-well plates (20 000 to 40 000 cells per well). The fluorescence and luminescence readings are carried out at ambient temperature on a microplate reader, Mithras LB 940 (Berthold). The yield from transfection of the Lingo-1-eYFP, Lingo-2-eYFP, Lingo-3-eYFP or Lingo-4-eYFP construct is evaluated by reading the fluorescence of the eYFP emitted at 530-540 nm after excitation at 480 nm. The yield from transfection of the Lingo-1-RLuc, Lingo-2-RLuc, Lingo-3-RLuc or Lingo-4-RLuc construct is evaluated by reading the luminescence (1 second) obtained immediately after the addition of the coelenterazine substrate (5 µM).

The measurement of the BRET signal is carried out immediately after the addition of coelenterazine. This causes the appearance of a bioluminescence signal with an emission peak at 480 nm, in agreement with the spectral properties of the Rluc. The energy transfer which takes place in the fusion protein between the Rluc and the eYFP causes the appearance of a fluorescence signal with a maximum emission at 530-540 nm, characteristic of the spectral properties of eYFP. The "BRET ratio" is defined as the ratio of the value of light emitted by the eYFP (530-540 nm) to the value of the light emitted by the RLuc (480 nm) after subtraction of the ratio obtained when the RLuc construct is expressed alone. Two sets of BRET filters were used: the first pair of filters (termed old filters) corresponds to a 480 nm filter, bandwidth of 20 nm, light transmittance of 60% and to a 530 nm filter, bandwidth of 25 nm, light transmittance of 60%. The second set of filters (termed new filters) corresponds to a 480 nm filter, bandwidth of 20 nm, light transmittance of 75% and to a 540 nm filter, bandwidth of 40 nm, light transmittance of 75%. The results are expressed in milli-BRET (mBu) which corresponds to the value of the BRET ratio multiplied by 1000.

The BRET measurement can also be carried out on adherent cells. In this case, the substrate is preincubated for 15 minutes before the luminescence reading.

6. Method of Screening for Lingo-1 Ligands

HEK-293 cells cultured in dishes (10 cm diameter) were transfected with Lingo-1-RLuc (250 ng) and Lingo-1-YFP (1500 ng) so as to reach approximately 50-60% of the BRETmax. The cells were resuspended in a physiological buffer (HBSS) 48 hours after transfection and distributed in 80 µl into 96-well plates (100 000 to 200 000 cells per well).

Prior to the addition of the cells, the various ligands (generally used at a final concentration of 20 µM) were distributed into the 96-well plates (in 10 µl).

After an incubation time of 15 minutes, coelenterazine h (Interchim) was added (in 10 µl) so as to obtain a final concentration of 5 µM.

The BRET reading was carried out at ambient temperature on a microplate reader, Mithras LB 940 (Berthold), using the new BRET filters. These experiments are also carried out using a stable line expressing Lingo-1-RLuc and Lingo-1-YFP.

7. Counter-Screening Test

The specificity of the effect of the molecules identified by means of our method was evaluated on the basis of the BRET signal originating from the formation of dimers of the β2 adrenergic receptor (counter-screening test).

To do this, HEK-293 cells were transfected with the β2 adrenergic receptor fused at the C-terminal with *Renilla* luciferase (β2AR-RLuc, 50 ng) acting as donor, and increasing concentrations of β2 adrenergic receptor fused at the C-terminal with the yellow fluorescent protein (β2AR-YFP, from 50 to 1000 ng), acting as acceptor. The cells were resuspended in a physiological buffer (HBSS) 48 hours after transfection and distributed into 96-well plates, in 80 μl (100 000 to 200 000 cells per well).

Prior to the addition of the cells, the products were distributed into the 96-well plates (in 10 μl).

After an incubation time of 15 minutes, coelenterazine h (Interchim) was added (in 10 μl) so as to obtain a final concentration of 5 μM. The BRET reading was carried out at ambient temperature on a microplate reader, Mithras LB 940 (Berthold), using the new BRET filters.

Example 1

Lingo-1 Forms a Dimer In Vivo

1/Lingo-1 Forms a Dimer in HEK-293 Cells

HEK-293 cells were first of all cotransfected with two plasmids which allow the expression of the Lingo-1 protein tagged with HA and Lingo-1 tagged with a fluorescent protein, YFP. Communoprecipitation experiments showed that, when the HA-tagged Lingo-1 protein is immunoprecipitated with agarose beads coupled to an anti-HA antibody (FIG. 1a), the YFP-tagged Lingo-1 protein is coimmunoprecipitated (FIG. 1b). These results show, for the first time, that Lingo-1 formed a dimer in vivo. These results also show for the first time that the whole and membrane form of Lingo-1 was capable of forming dimers in HEK-293 cells.

2/Lingo-1 Forms a Dimer in Neurons

Figure 2:
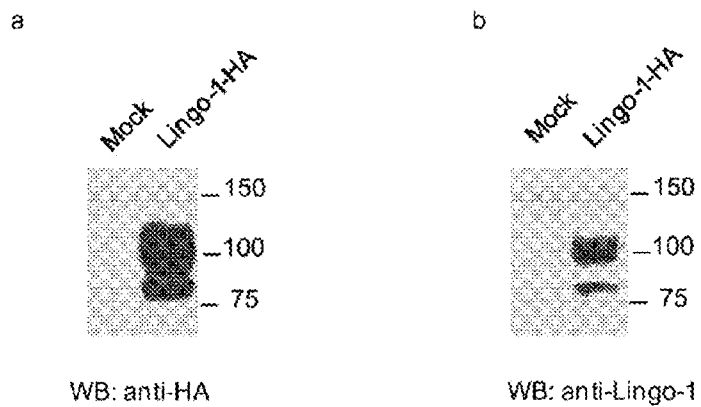
FIG. 2 represents the validation of the anti-Lingo-1 antibody. The cell lysates originating from HEK-293 cells transfected with a control plasmid, pcDNA$_3$ (mock), or the plasmid encoding the Lingo-1 protein fused at the N-terminal to an HA tag are analyzed on an acrylamide gel (8%). The use of an anti-HA antibody makes it possible to detect two immunoreactive bands at 80 and 100 kDa, probably corresponding to two different glycosylation states (cf. part a, showing the anti-HA Western Blot or WB). The presence of these same two immunoreactive bands can also be observed when the cell lysates are incubated with a Lingo-1 specific antibody (cf. part b, showing the anti-YFP Western Blot or WB).

After validation of the anti-Lingo-1 antibody (FIG. 2), existence of dimers in cortical neurons in culture was tested (FIG. 3a). Given that certain detergents used during the lysis can induce the formation of protein aggregates and result in the artefactual formation of dimers, the effect of chemical bridging before lysis of the cells was tested (FIG. 3b).

Figure 3:
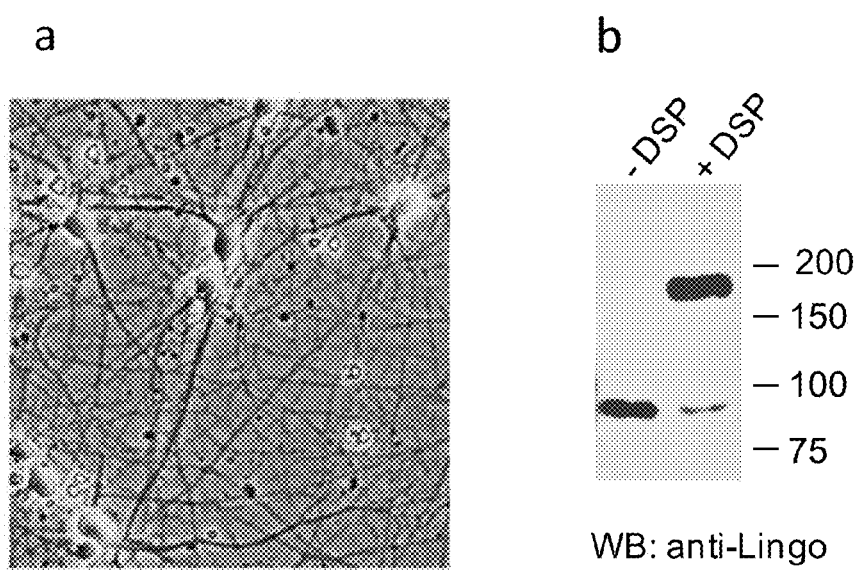
FIG. 3 represents the detection of Lingo-1 dimers in rat cortical neurons in culture. Twelve days after placing in culture, the cortical neurons put out extensions and form a network (cf. part a). The neurons are treated (+DSP) or not treated (−DSP) with a bridging agent, DSP (cf part b: anti-Lingo-1 Western Blot or WB b). Lingo-1 is indeed expressed in the cortical neurons, as attested to by the presence of an immunoreactive band at 90 kDa when the Western blot is incubated in the presence of the anti-Lingo-1 antibody (lane: −DSP). When the neurons are treated with DSP, an additional immunoreactive band appears at 180 kDa corresponding to the dimeric form of Lingo-1, this being to the detriment of the monomer at 90 kDa, which disappears (lane: +DSP).

Twelve days after having been placed in culture, cortical neurons put out extensions and formed a network (cf. FIG. 3, part a). The neurons were treated (+DSP) or not treated (−DSP) with a bridging agent, DSP, which acts at the level of the amine functions, before being lysed in a buffer containing 1% of triton X-100. Lingo-1 was indeed expressed in the cortical neurons, as attested to by the presence of an immunoreactive band at 90 kDa when the Western blot is incubated in the presence of the anti-Lingo-1 antibody (cf. FIG. 3, part b). When the neurons were treated with DSP, Lingo-1 indeed appeared in the form of dimers at 180 kDa (additional immunoreactive band appears at 180 kDa), this being to the detriment of the monomer at 90 kDa, which disappeared (cf. FIG. 3, part b).

Example 2

Detection of the Oligomerization of the Lingo-1 Protein in Live Cells Using the Bret Technique HEK-293 or SHSY-5Y cells were transfected with a fixed concentration of donor (100 ng of Lingo-1-RLuc plasmid) and increasing concentrations of acceptors, Lingo-1-YFP or the YFP fluorescent protein alone (from 50 ng to 4000 ng of plasmids). The BRET measurement was carried out 48 hours after transfection on live cells using sets of old filters and of new filters.

Figure 4:
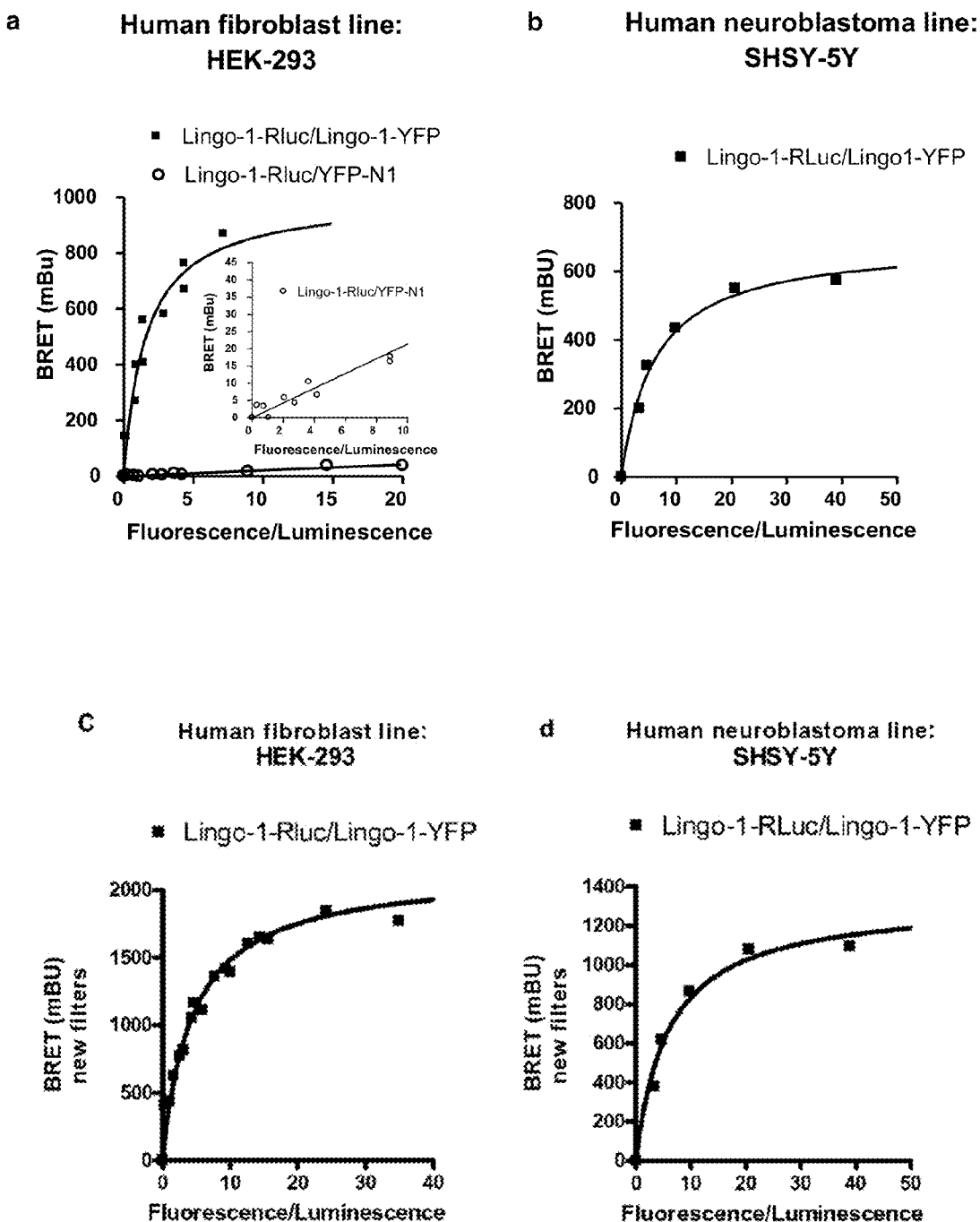
FIG. 4 represents the detection of the oligomerization of the Lingo-1 protein in live cells using the BRET technique. HEK-293 (parts a and c) and SHSY-5Y (parts b and d) cells were transfected with a fixed concentration of donor (100 ng of Lingo-1-RLuc plasmid) and increasing concentrations of acceptors, Lingo-1-YFP or the YFP fluorescent protein alone (from 50 ng to 4000 ng of YFP-N1 plasmids). The BRET measurement is carried out 48 hours after transfection on the live cells using the sets of old filters (parts a and b) and of new filters (parts c and d). The BRET signal is measured in mBu, for the Lingo-1-RLuc/Lingo-1-YFP product (squares) and the Lingo-1-RLuc/YFP-N1 product (circles).

The BRET signal observed with the old filters corresponding to the oligomerization of Lingo-1 is clearly specific since, when Lingo-1-RLuc and Lingo-1-YFP were coexpressed, the signal increased according to a hyperbolic curve and reached an asymptote in the two cell types (cf. FIGS. 4a and 4b). Furthermore, when Lingo-1-Rluc was coexpressed with the YFP protein alone, the BRET signal was much weaker (<20 mBU) and increased in a linear manner (cf. FIG. 4a, insert); thereby attesting to the appearance of nonspecific and random interactions.

These results show that the Lingo-1-RLuc and Lingo-1-YFP fusion proteins were capable of interacting so as to form dimers (or even oligomers) in live cells in culture. Indeed, with the old filters, a very strong BRET signal (of 100 to 800 mBU) was observed after coexpression of Lingo-1-Rluc and Lingo-1-YFP in HEK-293 cells (cf. FIG. 4a). Since Lingo-1 is exclusively expressed in the nervous system, it was also investigated whether Lingo-1 was capable of dimerizing in a more physiological environment, i.e. in human neuroblastoma cultures (cf. FIG. 4b). Once again, with the old filters, a very strong BRET signal (of 100 to 600 mBu) was observed. This signal is specific since, when saturation curves were plotted, the BRET signal reached a plateau both in the HEK-293 cells (cf. FIG. 4a) and in the SH-SY5Y cells (cf. FIG. 4b). In conclusion, the dimerization of Lingo-1 induced a strong and specific BRET signal.

In addition, the results obtained with a BRET measurement carried out under the same conditions with the set of new filters in the HEK-293 cells (cf. FIG. 4c) and in the SHSY-5Y human neuroblastoma cells (cf. FIG. 4d) coexpressing Lingo-1-Rluc and Lingo-1-YFP, made it possible to optimize the test, with a BRET signal that was twice as strong as previously being obtained.

Example 3

Figure 5:
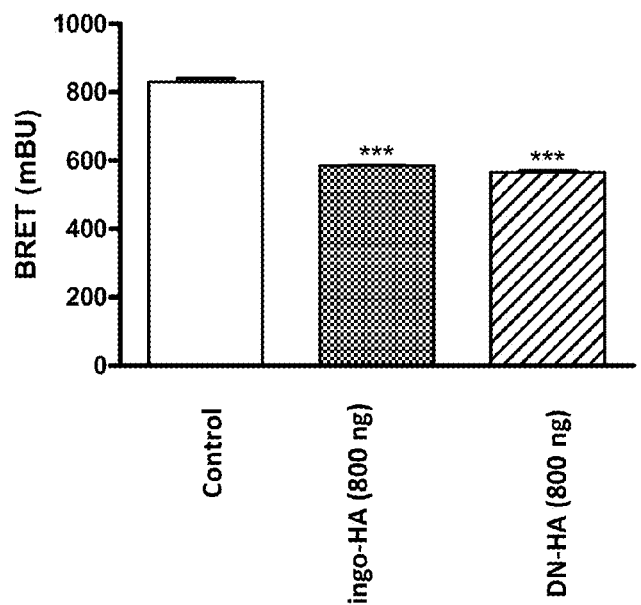
FIG. 5 represents the specificity of the interaction between Lingo-1-RLuc and Lingo-1-YFP. HEK-293 cells are transfected with the Lingo-1-RLuc and Lingo-1-YFP fusion proteins (with a constant donor/acceptor ratio) and increasing concentrations of the whole Lingo-1 protein (amino acids 1-620, "Lingo-HA" lane) or its dominant negative (amino acids 1-577, "DN-HA" lane) tagged with HA. The BRET measurement (mBu) is carried out 48 hours after the transfection on live cells. The HA-tagged constructs significantly reduce the BRET signal obtained between Lingo-1-RLuc and Lingo-1-YFP ("Control" lane) (p<0.001 vs control, ANOVA, NewMan Keuls).
Figure 5:
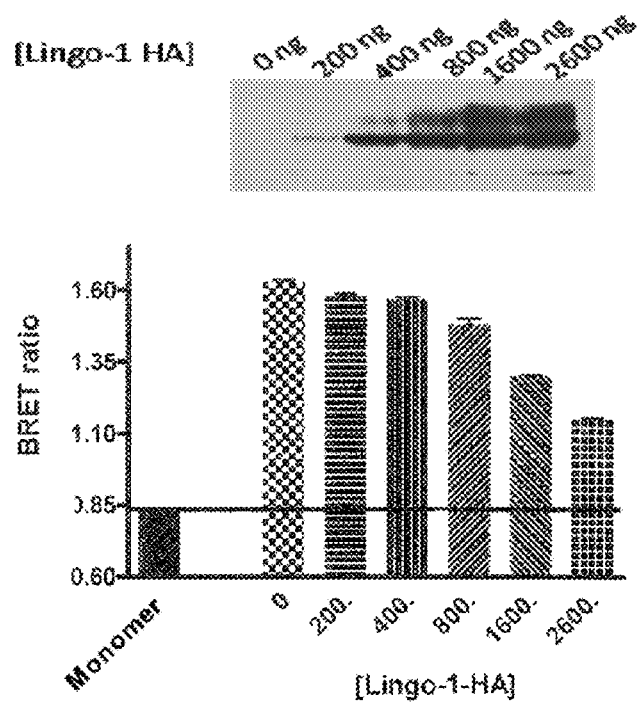

The Interaction Between Lingo-1-RLuc and Lingo-1-YFP is Specific and can be Modulated HEK-293 cells were transfected with the Lingo-1-RLuc and Lingo-1-YFP fusion proteins (the donor/acceptor ratio remains constant) and increasing concentrations of the whole Lingo-1 protein (Lingo-1-HA, amino acids 1-620) or the dominant negative thereof (DN-HA, amino acids 1-577) tagged with HA. The BRET measurement was carried out 48 hours after the transfection on live cells. The HA-tagged constructs significantly decreased the BRET signal obtained between Lingo-1-RLuc and Lingo-1-YFP (p<0.001 vs control, ANOVA, NewMan Keuls). The results are shown in FIG. 5.

The BRET signal obtained between the Lingo-1-RLuc and Lingo-1-YFP proteins is therefore specific and can be modulated. Indeed, when the HA-tagged whole Lingo-1 protein (620 amino acids) or the HA-tagged dominant negative of Lingo-1 (577 amino acids, without the cytoplasmic portion of the protein) was overexpressed at 800 ng, the BRET signal obtained between Lingo-1-RLuc and Lingo-1-YFP decreased significantly (FIG. 5a). In addition, when increasing concentrations of HA-tagged Lingo-1 protein were added (Lingo-1-HA at 0, 200, 400, 800, 1600 and 2600 ng), the BRET signal decreased (FIG. 5b); thereby making it possible to plot inhibition curves.

Thus, the results show that the HA-tagged Lingo-1 proteins prevent, by competition, the interaction of Lingo-1-RLuc with Lingo-1-YFP.

Example 4

Detection of the Oligomerization of the Lingo-1, Lingo-2, Lingo-3 and Lingo-4 Proteins in Live Cells Using the BRET Technique HEK-293 cells were transfected with a fixed concentration of donor (100 ng of Lingo-1-RLuc, Lingo-2-RLuc or Lingo-3-RLuc or Lingo-4-RLuc plasmid) and increasing concentrations of acceptors, Lingo-2-YFP or Lingo-3-YFP or Lingo-4-YFP (from 50 ng to 4000 ng of plasmids). The BRET measurement was carried out 48 hours after the transfection on live cells in 96-well and 384-well plates.

Figure 6:
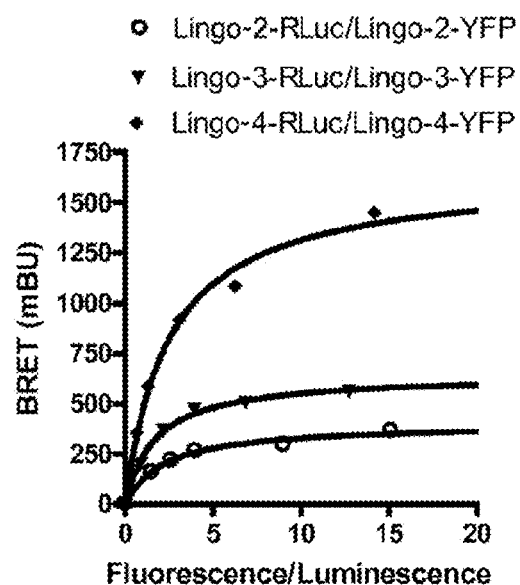
FIG. 6 shows the detection of the oligomerization of the Lingo-1, Lingo-2, Lingo-3 and Lingo-4 proteins in live cells using the BRET technique in 96-well plates (a) and in 384-well plates (b). HEK-293 cells are transfected with a fixed concentration of donor (100 ng of Lingo-1-RLuc, Lingo-2-RLuc or Lingo-3-RLuc or Lingo-4-RLuc plasmid) and increasing concentrations of acceptors (from 50 ng to 4000 ng of the Lingo-1-YFP, Lingo-2-YFP or Lingo-3-YFP or Lingo-4-YFP plasmids). (a) The BRET signal is measured (mBU) for Lingo-2-RLuc/Lingo-2-YFP (circles), Lingo-3-
Figure 6:
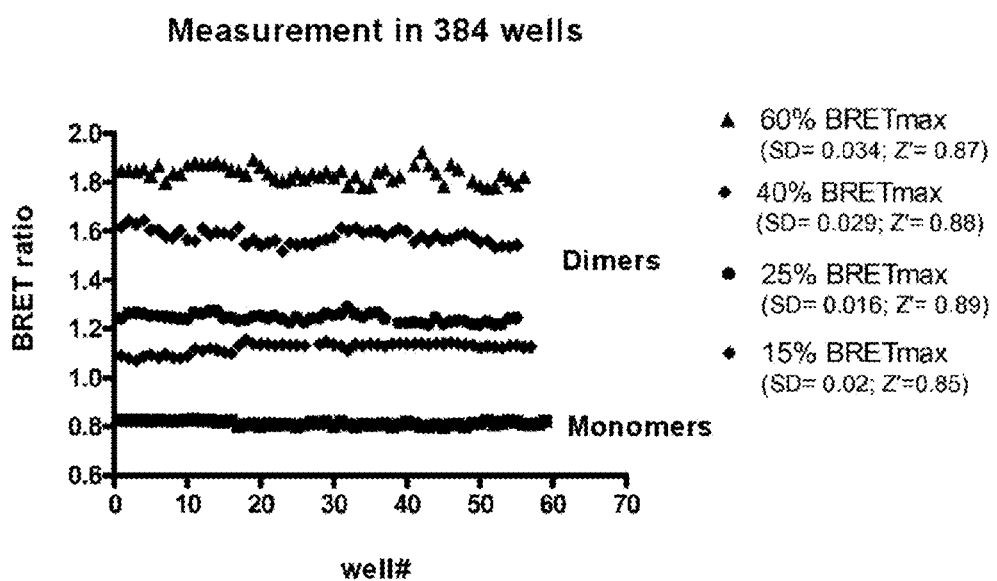

The BRET signal observed in 96-well plates, corresponding to the oligomerization of Lingo-2 and Lingo-3 and Lingo-4, is clearly specific since it increased according to a hyperbolic curve and reached an asymptote for each pair of proteins (cf. FIG. 6a).

In addition, the results show that a BRET signal obtained with Lingo-1 could be detected without any difficulty when the measurements were carried out in 384-well plates (high/medium-throughput). Moreover, the calculation of Z' (value p>0.85) shows how robust the test is (FIG. 6b).

The applicant therefore showed that it is possible, by measuring the luminescence transfer (BRET) between each modified monomer, to detect conformational variations in the dimer in vivo, in live cells in real time. In addition, it showed that the BRET measurement can be carried out on adherent cells or cells in suspension in 96-well plates and that it is adaptable to high/medium-throughput.

Example 5

Construction of Stable Lines

In order to ensure reproducibility of the high/medium-throughput BRET measurements, stable lines of HEK-293 cells expressing Lingo-1-RLuc or Lingo-1-YFP were developed.

The HEK-293 cells were transfected as previously described with Lingo-1-RLuc or Lingo-1-YFP plasmids carrying in particular neomycin resistance, as previously described. The cells having integrated the plasmid DNA were selected 48 hours after the transfection by adding the selection antibiotic (G-418 or geneticin at 2 mg/ml) to the culture medium. After two to three weeks of selection, several tens of antibiotic-resistant clones were recovered. Each clone was subsequently amplified so as to obtain a sufficient amount of cells to carry out the Lingo-1 expression test. This test consists in reading fluorescence in the case of clones of cells expressing Lingo-1-YFP or in reading luminescence after the addition of coelenterazine in the case of clones of cells expressing Lingo-1-RLuc, as previously described.

The results show that, among the clones tested (approximately a hundred or so clones tested) expressing Lingo-1-RLuc, several clones (for example C5, D1 and D2) express hLingo-1-RLuc at a satisfactory level (FIG. 7a) and were frozen. In addition, clone C5, which exhibits a good luminescence signal with good cell viability, was deposited, on 31 Mar., 2011, with the CNCM [National Collection of Microorganism Cultures] (Institut Pasteur, Paris) under number I-4463.

The results show a clone Y1 expressing hLingo-1-YFP at a satisfactory level, namely exhibiting a good fluorescence signal with good cell viability (FIG. 7b). In addition, clone Y1 was deposited, on 31 Mar., 2011, with the CNCM (Institut Pasteur, Paris) under number 1-4462.

Likewise, stable lines of HEK-293 cells coexpressing Lingo-1-RLuc and Lingo-1-YFP are developed. The clones coexpressing the two proteins at a satisfactory level are frozen and deposited with the CNCM.

Example 6

Method for Identifying Lingo-1 Ligands Using the System of the Invention

Validation of the Method of Identification of the Invention

HEK-293 cells were transfected with a fixed concentration of Lingo-1-RLuc (250 ng) and Lingo-1-YFP (1500 ng) so as to achieve approximately 50-60% of the BRETmax. The BRET measurement using the set of new filters was carried out 48 hours after the transfection on live cells in 96-well plates, in the presence of increasing concentrations of an HA-tagged known Lingo-1 inhibitor (DN-Lingo-1-HA at 0, 200, 400, 800, 1600 and 2600 ng) or of an HA-tagged neuronal protein which does not interact with Lingo-1 (Larp6-HA at 0, 200, 400, 800, 1600 and 2600 ng).

The results show that the HA-tagged known Lingo-1 inhibitor (DN-Lingo-1-HA) significantly decreased the BRET signal obtained between the Lingo-1-RLuc and Lingo-1-YFP proteins (FIG. 8a). In addition, the results show that this inhibitory effect was specific since the neuronal protein which does not interact with Lingo-1, called HA-tagged Larp6, did not modify the BRET signal (FIG. 8b).

Identification and Validation of a New Lingo-1 Dimerization Inhibitor: B27

HEK-293 cells were transfected with a fixed concentration of Lingo-1-RLuc (250 ng) and Lingo-1-YFP (1500 ng) so as to achieve approximately 50-60% of the BRETmax. The BRET measurement using the set of new filters was carried out 48 hours after the transfection on live cells in 96-well plates, in the presence of a fixed concentration of ligands (BDNF, N2, Fsk, pDBU at a final concentration of 20 µM) or of a solution of B27 (50×B27, Gibco, reference 17-504-044, 10 µl of pure solution), which are capable of modifying the BRET signal obtained between the Lingo-1-RLuc and Lingo-1-YFP proteins.

The results show that the B27 compound significantly decreased the dimerization of Lingo-1 in the HEK-293 cells (FIG. 9a). The effect of the B27 compound was reproduced at various levels of BRET and with various batches of B27: B27 without antioxidant (B27AO), B27 without insulin (B27ins) or without vitamin A (B27VitA) (FIG. 9b).

A kinetic study of the effect of B27 was also carried out, and revealed that the decrease caused by B27 was gradual and reached a plateau (−15%) after 10 minutes (FIG. 9c).

Counter-Screening Test: Specificity of B27

The specificity of B27 was evaluated in a counter-screening test (study of the signal originating from the dimerization of the $\beta$2-adrenergic receptor, $\beta$2AR), this dimerization having been previously described by Angers et al. [14].

HEK-293 cells were transfected with (i) a dimer of the $\beta$2AR receptor: the $\beta$2 adrenergic receptor fused at the C-terminal with *Renilla* luciferase ($\beta$2AR-RLuc, 50 ng) acting as donor, and increasing concentrations of $\beta$2 adrenergic receptor fused at the C-terminal with the yellow fluorescent protein ($\beta$2AR-YFP, from 100 to 2000 ng) acting as acceptor, or (ii) a dimer of Lingo-1: Lingo-1-RLuc acting as donor, and increasing concentrations of Lingo-1-YFP (from 100 to 2000 ng) acting as acceptor. The BRET measurement using the set of new filters was carried out 48 hours after the transfection on live cells in 96-well plates, in the absence or presence of a fixed concentration of B27 (50×B27, Gibco, reference 17-504-044, 10 µl of pure solution).

The results show that the BRET signal originating from the dimerization of the β2-adrenergic receptor was not modified in the counter-screening test (FIG. 10b), unlike the BRET signal originating from the dimerization of Lingo-1 (FIG. 10a).

The applicant thus showed that the screening method using the system of the invention makes it possible to identify specific ligands of Lingo-1.

REFERENCES

1. Carim-Todd et al., "LRRN6A/LERN1 (leucine-rich repeat neuronal protein 1), a novel gene with enriched expression in limbic system and neocortex". 2003, Eur. J; Neurosci. 18 (12):3167-82.
2. Mi et al., "LINGO-1 is a component of the Nogo-66 receptor/p75 signaling complex". 2004, Nat Neurosci. 7(3):221-8.
3. Ji et al., "LINGO-1 antagonist promotes functional recovery and axonal sprouting after spinal cord injury", 2006, Mol Cell Neurosci. 33(3):311-20.
4. Mi et al., "Lingo-1 negatively regulates myelination by oligodendrocytes", 2005, Nature Neuroscience 8: 745-751.
5. Lee et al. "NGF regulates the expression of axonal LINGO-1 to inhibit oligodendrocyte differentiation and myelination". 2007, J Neurosci. 27(1):220-5.
6. Zhao et al. "An in vitro study on the involvement of LINGO-1 and Rho GTPases in Nogo-A regulated differentiation of oligodendrocyte precursor cells", 2007, Mol Cell Neurosci. 36(2):260-9.
7. Mi et al., "Lingo-1 antagonist promotes spinal cord remyelination and axonal integrity in MOG-induced experimental autoimmune encephalomyelitis", 2007, Nature medicine 13: 1228-1233.
8. Fu et al., "Blocking LINGO-1 function promotes retinal ganglion cell survival following ocular hypertension and optic nerve transection". Invest Ophthalmol Vis Sci. 2008, 49(3):975-85.
9. Fu et al., "Combined effect of brain-derived neurotrophic factor and Lingo-1 fusion protein on long-term survival of retinal ganglion cells in chronic glaucoma", 2009, Neuroscience 162: 375-382.
10. Zhao et al. "Inactivation of glycogen synthase kinase-3beta and up-regulation of LINGO-1 are involved in LINGO-1 antagonist regulated survival of cerebellar granular neurons", 2008, Cell Mol Neurobiol. 28(5):727-35.
11. Inoue et al., "Inhibition of the leucine-rich repeat protein Lingo-1 enhances survival, structure, and function of dopaminergic neurons in Parkinson's disease models", 2007, PNAS 104: 14430-14435.
12. Mosyak et al., "The structure of Lingo-1 ectodomain, a module implicated in CNS repair inhibition", 2006, J. Biol. Chem. 281: 36378-36390.
13. Xu et al., "A bioluminescence resonance energy transfer (BRET) system: application to interacting circadian clock proteins" (1999) Proc. Natl. Acad. Sci. USA. 96, 151-156.
14. Angers 2000, "Detection of beta 2-adrenergic receptor dimerization in living cells using bioluminescence resonance energy transfer (BRET)" (2000) Proc. Natl. Acad. Sci. USA 97: 3684-3689.
15. Mi et al., "Lingo-1 and its role in CNS repair", 2008, The Int. J. Bioch. Cell. Biol. 40: 1971-1978.
16. Rudick et al., "Lingo-1 antagonists as therapy for multiple sclerosis: in vitro and in vivo evidence", 2008, Expert Opin. Biol. Ther. 8: 1561-1570.
17. Kamal et al., "Improved donor/acceptor BRET couples for monitoring beta-arrestin recruitment to G protein-coupled receptors". Biotechnol J. 2009 September; 4(9): 1337-44.
18. Kocan M et al., "Demonstration of improvements to the bioluminescence resonance energy transfer (BRET) technology for the monitoring of G protein-coupled receptors in live cells", J Biomol Screen. 2008 October; 13(9):888-98.
19. Michelini E et al., "Luminescent probes and visualization of bioluminescence", Methods Mol Biol. 2009; 574: 1-13.
20. Kroeger et al., "Constitutive and agonist-dependent homo-oligomerization of the thyrotropin-releasing hormone receptor" (2001) J Biol Chem, 276, 12736-12743.
21. Maurel D et al., "Cell-surface protein-protein interaction analysis with time-resolved FRET and snap-tag technologies: application to GPCR oligomerization" (2008), Nat Methods (6):561-7.
22. Hermand P et al., "Functional adhesiveness of the CX3CL1 chemokine requires its aggregation. Role of the transmembrane domain" (2008) J Biol Chem 283(44): 30225-34.
23. Whitfield J et al., "High-throughput methods to detect dimerization of Bcl-2 family proteins" (2003), Anal Biochem, 322(2):170-8.

The invention claimed is:

1. A detection system comprising:
a) a first coupling product (i) comprising a monomer (A) of a whole or membrane form of a protein selected from the group consisting of: Lingo-1, Lingo-2, Lingo-3 and Lingo-4, and (ii) a first probe which is a fluorescent protein selected from the group consisting of GFP ("Green Fluorescent Protein"), YFP ("Yellow Fluorescent Protein"), Enhanced Yellow Fluorescent Protein (eYFP), eGFP, GFP2, GFP10, RGFP (*Renilla* Green Fluorescent Protein") and YPet, said first probe being capable of emitting a detectable signal when said monomer (A) undergoes conformational changes,
b) a second coupling product comprising (i) a monomer (B) of a whole or membrane form of a protein selected from the group consisting of: Lingo-1, Lingo-2, Lingo-3 and Lingo-4, and (ii) a second probe which is a luciferase selected from the group consisting of *Renilla* luciferase, RLuc8, firefly luciferase, *Gaussia* luciferase and Aequorin, said second probe being capable of emitting a detectable signal when said monomer (B) undergoes conformational changes,
wherein said first coupling product and said second coupling product form a dimer by interaction between said monomers (A) and (B) and,
said dimer undergoes a conformational change upon binding to a candidate molecule, and said conformational change causes a change of the detectable signal emitted by said first and second probes, generated by a transfer of energy from the first probe to the second probe, and wherein said system is in the form of a cell suspension, or a culture of adherent cells, membranes or tissues.

2. The detection system as claimed in claim 1, said system being a bioluminescence resonance energy transfer system.

3. A method for identifying a ligand of a protein chosen from Lingo-1, Lingo-2, Lingo-3 and Lingo-4, comprising the following steps:
   a) incubating a system as defined in claim 1 and a candidate molecule,
   b) detecting a modification of the signal emitted by the second probe,
   said modification of the signal revealing the binding of said candidate molecule to at least one of said coupling products.

4. The method as claimed in claim 3, performed with a high-throughput screening system.

5. The system as in claim 1, comprising a high-throughput screening system.

* * * * *

SEQUENCE LISTING

<160> NUMBER OF SEQ ID NOS: 20

<210> SEQ ID NO 1
<211> LENGTH: 620
<212> TYPE: PRT
<213> ORGANISM: Homo sapiens

<400> SEQUENCE: 1

Met Gln Val Ser Lys Arg Met Leu Ala Gly Gly Val Arg Ser Met Pro
1               5                   10                  15

Ser Pro Leu Leu Ala Cys Trp Gln Pro Ile Leu Leu Leu Val Leu Gly
            20                  25                  30

```
Ser Val Leu Ser Gly Ser Ala Thr Gly Cys Pro Pro Arg Cys Glu Cys
            35                  40                  45

Ser Ala Gln Asp Arg Ala Val Leu Cys His Arg Lys Arg Phe Val Ala
        50                  55                  60

Val Pro Glu Gly Ile Pro Thr Glu Thr Arg Leu Leu Asp Leu Gly Lys
65                  70                  75                  80

Asn Arg Ile Lys Thr Leu Asn Gln Asp Glu Phe Ala Ser Phe Pro His
                85                  90                  95

Leu Glu Glu Leu Glu Leu Asn Glu Asn Ile Val Ser Ala Val Glu Pro
            100                 105                 110

Gly Ala Phe Asn Asn Leu Phe Asn Leu Arg Thr Leu Gly Leu Arg Ser
        115                 120                 125

Asn Arg Leu Lys Leu Ile Pro Leu Gly Val Phe Thr Gly Leu Ser Asn
130                 135                 140

Leu Thr Lys Leu Asp Ile Ser Glu Asn Lys Ile Val Ile Leu Leu Asp
145                 150                 155                 160

Tyr Met Phe Gln Asp Leu Tyr Asn Leu Lys Ser Leu Glu Val Gly Asp
                165                 170                 175

Asn Asp Leu Val Tyr Ile Ser His Arg Ala Phe Ser Gly Leu Asn Ser
            180                 185                 190

Leu Glu Gln Leu Thr Leu Glu Lys Cys Asn Leu Thr Ser Ile Pro Thr
        195                 200                 205

Glu Ala Leu Ser His Leu His Gly Leu Ile Val Leu Arg Leu Arg His
210                 215                 220

Leu Asn Ile Asn Ala Ile Arg Asp Tyr Ser Phe Lys Arg Leu Tyr Arg
225                 230                 235                 240

Leu Lys Val Leu Glu Ile Ser His Trp Pro Tyr Leu Asp Thr Met Thr
                245                 250                 255

Pro Asn Cys Leu Tyr Gly Leu Asn Leu Thr Ser Leu Ser Ile Thr His
            260                 265                 270

Cys Asn Leu Thr Ala Val Pro Tyr Leu Ala Val Arg His Leu Val Tyr
        275                 280                 285

Leu Arg Phe Leu Asn Leu Ser Tyr Asn Pro Ile Ser Thr Ile Glu Gly
290                 295                 300

Ser Met Leu His Glu Leu Leu Arg Leu Gln Glu Ile Gln Leu Val Gly
305                 310                 315                 320

Gly Gln Leu Ala Val Val Glu Pro Tyr Ala Phe Arg Gly Leu Asn Tyr
                325                 330                 335

Leu Arg Val Leu Asn Val Ser Gly Asn Gln Leu Thr Thr Leu Glu Glu
            340                 345                 350

Ser Val Phe His Ser Val Gly Asn Leu Glu Thr Leu Ile Leu Asp Ser
        355                 360                 365

Asn Pro Leu Ala Cys Asp Cys Arg Leu Leu Trp Val Phe Arg Arg Arg
370                 375                 380

Trp Arg Leu Asn Phe Asn Arg Gln Gln Pro Thr Cys Ala Thr Pro Glu
385                 390                 395                 400

Phe Val Gln Gly Lys Glu Phe Lys Asp Phe Pro Asp Val Leu Leu Pro
                405                 410                 415

Asn Tyr Phe Thr Cys Arg Arg Ala Arg Ile Arg Asp Arg Lys Ala Gln
            420                 425                 430

Gln Val Phe Val Asp Glu Gly His Thr Val Gln Phe Val Cys Arg Ala
        435                 440                 445
```

```
Asp Gly Asp Pro Pro Ala Ile Leu Trp Leu Ser Pro Arg Lys His
450                 455                 460

Leu Val Ser Ala Lys Ser Asn Gly Arg Leu Thr Val Phe Pro Asp Gly
465                 470                 475                 480

Thr Leu Glu Val Arg Tyr Ala Gln Val Gln Asp Asn Gly Thr Tyr Leu
                485                 490                 495

Cys Ile Ala Ala Asn Ala Gly Gly Asn Asp Ser Met Pro Ala His Leu
            500                 505                 510

His Val Arg Ser Tyr Ser Pro Asp Trp Pro His Gln Pro Asn Lys Thr
        515                 520                 525

Phe Ala Phe Ile Ser Asn Gln Pro Gly Glu Gly Glu Ala Asn Ser Thr
530                 535                 540

Arg Ala Thr Val Pro Phe Pro Phe Asp Ile Lys Thr Leu Ile Ile Ala
545                 550                 555                 560

Thr Thr Met Gly Phe Ile Ser Phe Leu Gly Val Val Leu Phe Cys Leu
                565                 570                 575

Val Leu Leu Phe Leu Trp Ser Arg Gly Lys Gly Asn Thr Lys His Asn
            580                 585                 590

Ile Glu Ile Glu Tyr Val Pro Arg Lys Ser Asp Ala Gly Ile Ser Ser
        595                 600                 605

Ala Asp Ala Pro Arg Lys Phe Asn Met Lys Met Ile
610                 615                 620

<210> SEQ ID NO 2
<211> LENGTH: 606
<212> TYPE: PRT
<213> ORGANISM: Homo sapiens

<400> SEQUENCE: 2

Met Leu His Thr Ala Ile Ser Cys Trp Gln Pro Phe Leu Gly Leu Ala
1               5                   10                  15

Val Val Leu Ile Phe Met Gly Ser Thr Ile Gly Cys Pro Ala Arg Cys
                20                  25                  30

Glu Cys Ser Ala Gln Asn Lys Ser Val Ser Cys His Arg Arg Arg Leu
            35                  40                  45

Ile Ala Ile Pro Glu Gly Ile Pro Ile Glu Thr Lys Ile Leu Asp Leu
        50                  55                  60

Ser Lys Asn Arg Leu Lys Ser Val Asn Pro Glu Glu Phe Ile Ser Tyr
65                  70                  75                  80

Pro Leu Leu Glu Glu Ile Asp Leu Ser Asp Asn Ile Ile Ala Asn Val
                85                  90                  95

Glu Pro Gly Ala Phe Asn Asn Leu Phe Asn Leu Arg Ser Leu Arg Leu
            100                 105                 110

Lys Gly Asn Arg Leu Lys Leu Val Pro Leu Gly Val Phe Thr Gly Leu
        115                 120                 125

Ser Asn Leu Thr Lys Leu Asp Ile Ser Glu Asn Lys Ile Val Ile Leu
130                 135                 140

Leu Asp Tyr Met Phe Gln Asp Leu His Asn Leu Lys Ser Leu Glu Val
145                 150                 155                 160

Gly Asp Asn Asp Leu Val Tyr Ile Ser His Arg Ala Phe Ser Gly Leu
                165                 170                 175

Leu Ser Leu Glu Gln Leu Thr Leu Glu Lys Cys Asn Leu Thr Ala Val
            180                 185                 190

Pro Thr Glu Ala Leu Ser His Leu Arg Ser Leu Ile Ser Leu His Leu
        195                 200                 205
```

-continued

```
Lys His Leu Asn Ile Asn Asn Met Pro Val Tyr Ala Phe Lys Arg Leu
    210                 215                 220

Phe His Leu Lys His Leu Glu Ile Asp Tyr Trp Pro Leu Leu Asp Met
225                 230                 235                 240

Met Pro Ala Asn Ser Leu Tyr Gly Leu Asn Leu Thr Ser Leu Ser Val
                245                 250                 255

Thr Asn Thr Asn Leu Ser Thr Val Pro Phe Leu Ala Phe Lys His Leu
            260                 265                 270

Val Tyr Leu Thr His Leu Asn Leu Ser Tyr Asn Pro Ile Ser Thr Ile
        275                 280                 285

Glu Ala Gly Met Phe Ser Asp Leu Ile Arg Leu Gln Glu Leu His Ile
    290                 295                 300

Val Gly Ala Gln Leu Arg Thr Ile Glu Pro His Ser Phe Gln Gly Leu
305                 310                 315                 320

Arg Phe Leu Arg Val Leu Asn Val Ser Gln Asn Leu Leu Glu Thr Leu
                325                 330                 335

Glu Glu Asn Val Phe Ser Ser Pro Arg Ala Leu Glu Val Leu Ser Ile
            340                 345                 350

Asn Asn Asn Pro Leu Ala Cys Asp Cys Arg Leu Leu Trp Ile Leu Gln
        355                 360                 365

Arg Gln Pro Thr Leu Gln Phe Gly Gly Gln Pro Met Cys Ala Gly
    370                 375                 380

Pro Asp Thr Ile Arg Glu Arg Ser Phe Lys Asp Phe His Ser Thr Ala
385                 390                 395                 400

Leu Ser Phe Tyr Phe Thr Cys Lys Lys Pro Lys Ile Arg Glu Lys Lys
                405                 410                 415

Leu Gln His Leu Leu Val Asp Glu Gly Gln Thr Val Gln Leu Glu Cys
            420                 425                 430

Ser Ala Asp Gly Asp Pro Gln Pro Val Ile Ser Trp Val Thr Pro Arg
        435                 440                 445

Arg Arg Phe Ile Thr Thr Lys Ser Asn Gly Arg Ala Thr Val Leu Gly
    450                 455                 460

Asp Gly Thr Leu Glu Ile Arg Phe Ala Gln Asp Gln Asp Ser Gly Met
465                 470                 475                 480

Tyr Val Cys Ile Ala Ser Asn Ala Ala Gly Asn Asp Thr Phe Thr Ala
                485                 490                 495

Ser Leu Thr Val Lys Gly Phe Ala Ser Asp Arg Phe Leu Tyr Ala Asn
            500                 505                 510

Arg Thr Pro Met Tyr Met Thr Asp Ser Asn Asp Thr Ile Ser Asn Gly
        515                 520                 525

Thr Asn Ala Asn Thr Phe Ser Leu Asp Leu Lys Thr Ile Leu Val Ser
    530                 535                 540

Thr Ala Met Gly Cys Phe Thr Phe Leu Gly Val Val Leu Phe Cys Phe
545                 550                 555                 560

Leu Leu Leu Phe Val Trp Ser Arg Gly Lys Gly Lys His Lys Asn Ser
                565                 570                 575

Ile Asp Leu Glu Tyr Val Pro Arg Lys Asn Asn Gly Ala Val Val Glu
            580                 585                 590

Gly Glu Val Ala Gly Pro Arg Arg Phe Asn Met Lys Met Ile
        595                 600                 605

<210> SEQ ID NO 3
<211> LENGTH: 592
```

<212> TYPE: PRT
<213> ORGANISM: Homo sapiens

<400> SEQUENCE: 3

```
Met Thr Cys Trp Leu Cys Val Leu Ser Leu Pro Leu Leu Leu Pro
1               5                   10                  15

Ala Ala Pro Pro Pro Ala Gly Gly Cys Pro Ala Arg Cys Glu Cys Thr
            20                  25                  30

Val Gln Thr Arg Ala Val Ala Cys Thr Arg Arg Leu Thr Ala Val
        35                  40                  45

Pro Asp Gly Ile Pro Ala Glu Thr Arg Leu Leu Glu Leu Ser Arg Asn
    50                  55                  60

Arg Ile Arg Cys Leu Asn Pro Gly Asp Leu Ala Ala Leu Pro Ala Leu
65                  70                  75                  80

Glu Glu Leu Asp Leu Ser Glu Asn Ala Ile Ala His Val Glu Pro Gly
                85                  90                  95

Ala Phe Ala Asn Leu Pro Arg Leu Arg Val Leu Arg Leu Arg Gly Asn
            100                 105                 110

Gln Leu Lys Leu Ile Pro Pro Gly Val Phe Thr Arg Leu Asp Asn Leu
        115                 120                 125

Thr Leu Leu Asp Leu Ser Glu Asn Lys Leu Val Ile Leu Leu Asp Tyr
    130                 135                 140

Thr Phe Gln Asp Leu His Ser Leu Arg Arg Leu Glu Val Gly Asp Asn
145                 150                 155                 160

Asp Leu Val Phe Val Ser Arg Arg Ala Phe Ala Gly Leu Leu Ala Leu
                165                 170                 175

Glu Glu Leu Thr Leu Glu Arg Cys Asn Leu Thr Ala Leu Ser Gly Glu
            180                 185                 190

Ser Leu Gly His Leu Arg Ser Leu Gly Ala Leu Arg Leu Arg His Leu
        195                 200                 205

Ala Ile Ala Ser Leu Glu Asp Gln Asn Phe Arg Arg Leu Pro Gly Leu
    210                 215                 220

Leu His Leu Glu Ile Asp Asn Trp Pro Leu Leu Glu Glu Val Ala Ala
225                 230                 235                 240

Gly Ser Leu Arg Gly Leu Asn Leu Thr Ser Leu Ser Val Thr His Thr
                245                 250                 255

Asn Ile Thr Ala Val Pro Ala Ala Ala Leu Arg His Gln Ala His Leu
            260                 265                 270

Thr Cys Leu Asn Leu Ser His Asn Pro Ile Ser Thr Val Pro Arg Gly
        275                 280                 285

Ser Phe Arg Asp Leu Val Arg Leu Arg Glu Leu His Leu Ala Gly Ala
    290                 295                 300

Leu Leu Ala Val Val Glu Pro Gln Ala Phe Leu Gly Leu Arg Gln Ile
305                 310                 315                 320

Arg Leu Leu Asn Leu Ser Asn Asn Leu Leu Ser Thr Leu Glu Glu Ser
                325                 330                 335

Thr Phe His Ser Val Asn Thr Leu Glu Thr Leu Arg Val Asp Gly Asn
            340                 345                 350

Pro Leu Ala Cys Asp Cys Arg Leu Leu Trp Ile Val Gln Arg Arg Lys
        355                 360                 365

Thr Leu Asn Phe Asp Gly Arg Leu Pro Ala Cys Ala Thr Pro Ala Glu
    370                 375                 380

Val Arg Gly Asp Ala Leu Arg Asn Leu Pro Asp Ser Val Leu Phe Glu
385                 390                 395                 400
```

```
Tyr Phe Val Cys Arg Lys Pro Lys Ile Arg Glu Arg Leu Gln Arg
                405                 410                 415

Val Thr Ala Thr Ala Gly Glu Asp Val Arg Phe Leu Cys Arg Ala Glu
            420                 425                 430

Gly Glu Pro Ala Pro Thr Val Ala Trp Val Thr Pro Gln His Arg Pro
            435                 440                 445

Val Thr Ala Thr Ser Ala Gly Arg Ala Arg Val Leu Pro Gly Gly Thr
        450                 455                 460

Leu Glu Ile Gln Asp Ala Arg Pro Gln Asp Ser Gly Thr Tyr Thr Cys
465                 470                 475                 480

Val Ala Ser Asn Ala Gly Gly Asn Asp Thr Tyr Phe Ala Thr Leu Thr
                485                 490                 495

Val Arg Pro Glu Pro Ala Ala Asn Arg Thr Pro Gly Glu Ala His Asn
                500                 505                 510

Glu Thr Leu Ala Ala Leu Arg Ala Pro Leu Asp Leu Thr Thr Ile Leu
            515                 520                 525

Val Ser Thr Ala Met Gly Cys Ile Thr Phe Leu Gly Val Val Leu Phe
        530                 535                 540

Cys Phe Val Leu Leu Phe Val Trp Ser Arg Gly Arg Gly Gln His Lys
545                 550                 555                 560

Asn Asn Phe Ser Val Glu Tyr Ser Phe Arg Lys Val Asp Gly Pro Ala
                565                 570                 575

Ala Ala Ala Gly Gln Gly Gly Ala Arg Lys Phe Asn Met Lys Met Ile
            580                 585                 590

<210> SEQ ID NO 4
<211> LENGTH: 593
<212> TYPE: PRT
<213> ORGANISM: Homo sapiens

<400> SEQUENCE: 4

Met Asp Ala Ala Thr Ala Pro Lys Gln Ala Trp Pro Pro Trp Pro Pro
1               5                   10                  15

Leu Leu Phe Leu Leu Leu Leu Pro Gly Gly Ser Gly Gly Ser Cys Pro
            20                  25                  30

Ala Val Cys Asp Cys Thr Ser Gln Pro Gln Ala Val Leu Cys Gly His
            35                  40                  45

Arg Gln Leu Glu Ala Val Pro Gly Gly Leu Pro Leu Asp Thr Glu Leu
        50                  55                  60

Leu Asp Leu Ser Gly Asn Arg Leu Trp Gly Leu Gln Gln Gly Met Leu
65                  70                  75                  80

Ser Arg Leu Ser Leu Leu Gln Glu Leu Asp Leu Ser Tyr Asn Gln Leu
                85                  90                  95

Ser Thr Leu Glu Pro Gly Ala Phe His Gly Leu Gln Ser Leu Leu Thr
            100                 105                 110

Leu Arg Leu Gln Gly Asn Arg Leu Arg Ile Met Gly Pro Gly Val Phe
            115                 120                 125

Ser Gly Leu Ser Ala Leu Thr Leu Leu Asp Leu Arg Leu Asn Gln Ile
        130                 135                 140

Val Leu Phe Leu Asp Gly Ala Phe Gly Glu Leu Gly Ser Leu Gln Lys
145                 150                 155                 160

Leu Glu Val Gly Asp Asn His Leu Val Phe Val Ala Pro Gly Ala Phe
                165                 170                 175

Ala Gly Leu Ala Lys Leu Ser Thr Leu Thr Leu Glu Arg Cys Asn Leu
```

```
                180             185             190
Ser Thr Val Pro Gly Leu Ala Leu Ala Arg Leu Pro Ala Leu Val Ala
        195             200             205
Leu Arg Leu Arg Glu Leu Asp Ile Gly Arg Leu Pro Ala Gly Ala Leu
        210             215             220
Arg Gly Leu Gly Gln Leu Lys Glu Leu Glu Ile His Leu Trp Pro Ser
225             230             235             240
Leu Glu Ala Leu Asp Pro Gly Ser Leu Val Gly Leu Asn Leu Ser Ser
        245             250             255
Leu Ala Ile Thr Arg Cys Asn Leu Ser Ser Val Pro Phe Gln Ala Leu
        260             265             270
Tyr His Leu Ser Phe Leu Arg Val Leu Asp Leu Ser Gln Asn Pro Ile
        275             280             285
Ser Ala Ile Pro Ala Arg Arg Leu Ser Pro Leu Val Arg Leu Gln Glu
        290             295             300
Leu Arg Leu Ser Gly Ala Cys Leu Thr Ser Ile Ala Ala His Ala Phe
305             310             315             320
His Gly Leu Thr Ala Phe His Leu Leu Asp Val Ala Asp Asn Ala Leu
        325             330             335
Gln Thr Leu Glu Glu Thr Ala Phe Pro Ser Pro Asp Lys Leu Val Thr
        340             345             350
Leu Arg Leu Ser Gly Asn Pro Leu Thr Cys Asp Cys Arg Leu Leu Trp
        355             360             365
Leu Leu Arg Leu Arg Arg His Leu Asp Phe Gly Met Ser Pro Pro Ala
        370             375             380
Cys Ala Gly Pro His His Val Gln Gly Lys Ser Leu Lys Glu Phe Ser
385             390             395             400
Asp Ile Leu Pro Pro Gly His Phe Thr Cys Lys Pro Ala Leu Ile Arg
        405             410             415
Lys Ser Gly Pro Arg Trp Val Ile Ala Glu Glu Gly His Ala Val
        420             425             430
Phe Ser Cys Ser Gly Asp Gly Asp Pro Ala Pro Thr Val Ser Trp Met
        435             440             445
Arg Pro His Gly Ala Trp Leu Gly Arg Ala Gly Arg Val Arg Val Leu
        450             455             460
Glu Asp Gly Thr Leu Glu Ile Arg Ser Val Gln Leu Arg Asp Arg Gly
465             470             475             480
Ala Tyr Val Cys Val Val Ser Asn Val Ala Gly Asn Asp Ser Leu Arg
        485             490             495
Thr Trp Leu Glu Val Ile Gln Val Glu Pro Pro Asn Gly Thr Leu Ser
        500             505             510
Asp Pro Asn Ile Thr Val Pro Gly Ile Pro Gly Pro Phe Phe Leu Asp
        515             520             525
Ser Arg Gly Val Ala Met Val Leu Ala Val Gly Phe Leu Pro Phe Leu
        530             535             540
Thr Ser Val Thr Leu Cys Phe Gly Leu Ile Ala Leu Trp Ser Lys Gly
545             550             555             560
Lys Gly Arg Val Lys His His Met Thr Phe Asp Phe Val Ala Pro Arg
        565             570             575
Pro Ser Gly Asp Lys Asn Ser Gly Gly Asn Arg Val Thr Ala Lys Leu
        580             585             590
Phe
```

<210> SEQ ID NO 5
<211> LENGTH: 2932
<212> TYPE: DNA
<213> ORGANISM: Homo sapiens

<400> SEQUENCE: 5

| | | | | | |
|---|---|---|---|---|---|
| ggagagacat | gcgattggtg | accgagccga | gcggaccgaa | ggcgcgcccg | agatgcaggt | 60 |
| gagcaagagg | atgctggcgg | ggggcgtgag | gagcatgccc | agcccctcc | tggcctgctg | 120 |
| gcagcccatc | ctcctgctgg | tgctgggctc | agtgctgtca | ggctcggcca | cgggctgccc | 180 |
| gccccgctgc | gagtgctccg | cccaggaccg | cgctgtgctg | tgccaccgca | agcgctttgt | 240 |
| ggcagtcccc | gagggcatcc | ccaccgagac | gcgcctgctg | gacctaggca | agaaccgcat | 300 |
| caaaacgctc | aaccaggacg | agttcgccag | cttcccgcac | ctggaggagc | tggagctcaa | 360 |
| cgagaacatc | gtgagcgccg | tggagcccgg | cgccttcaac | aacctcttca | acctccggac | 420 |
| gctgggtctc | cgcagcaacc | gcctgaagct | catcccgcta | ggcgtcttca | ctggcctcag | 480 |
| caacctgacc | aagctggaca | tcagcgagaa | caagatcgtt | atcctactgg | actacatgtt | 540 |
| tcaggacctg | tacaacctca | agtcactgga | ggttggcgac | aatgacctcg | tctacatctc | 600 |
| tcaccgcgcc | ttcagcggcc | tcaacagcct | ggagcagctg | acgctggaga | aatgcaacct | 660 |
| gacctccatc | cccaccgagg | cgctgtccca | cctgcacggc | ctcatcgtcc | tgaggctccg | 720 |
| gcacctcaac | atcaatgcca | tccgggacta | ctccttcaag | aggctgtacc | gactcaaggt | 780 |
| cttggagatc | tcccactggc | cctacttgga | caccatgaca | cccaactgcc | tctacggcct | 840 |
| caacctgacg | tccctgtcca | tcacacactg | caatctgacc | gctgtgccct | acctggccgt | 900 |
| ccgccaccta | gtctatctcc | gcttcctcaa | cctctcctac | aaccccatca | gcaccattga | 960 |
| gggctccatg | ttgcatgagc | tgctccggct | gcaggagatc | cagctggtgg | gcgggcagct | 1020 |
| ggccgtggtg | gagccctatg | ccttccgcgg | cctcaactac | ctgcgcgtgc | tcaatgtctc | 1080 |
| tggcaaccag | ctgaccacac | tggaggaatc | agtcttccac | tcggtgggca | acctggagac | 1140 |
| actcatcctg | gactccaacc | cgctggcctg | cgactgtcgg | ctcctgtggg | tgttccggcg | 1200 |
| ccgctggcgc | ctcaacttca | accggcagca | gcccacgtgc | gccacgcccg | agtttgtcca | 1260 |
| gggcaaggag | ttcaaggact | tccctgatgt | gctactgccc | aactacttca | cctgccgccg | 1320 |
| cgcccgcatc | cggaccgca | aggcccagca | ggtgtttgtg | gacgagggcc | acacggtgca | 1380 |
| gtttgtgtgc | cgggccgatg | gcgacccgcc | gccgccatc | ctctggctct | caccccgaaa | 1440 |
| gcacctggtc | tcagccaaga | gcaatgggcg | gctcacagtc | ttccctgatg | gcacgctgga | 1500 |
| ggtgcgctac | gcccaggtac | aggacaacgg | cacgtacctg | tgcatcgcgg | ccaacgcggg | 1560 |
| cggcaacgac | tccatgcccg | cccacctgca | tgtgcgcagc | tactcgcccg | actggcccca | 1620 |
| tcagcccaac | aagaccttcg | ctttcatctc | caaccagccg | ggcgagggag | aggccaacag | 1680 |
| cacccgcgcc | actgtgcctt | ccccttcga | catcaagacc | ctcatcatcg | ccaccaccat | 1740 |
| gggcttcatc | tctttcctgg | gcgtcgtcct | cttctgcctg | gtgctgctgt | ttctctggag | 1800 |
| ccggggcaag | ggcaacacaa | agcacaacat | cgagatcgag | tatgtgcccc | gaaagtcgga | 1860 |
| cgcaggcatc | agctccgccg | acgcgccccg | caagttcaac | atgaagatga | tatgaggccg | 1920 |
| gggcgggggg | cagggacccc | cgggcggccg | ggcagggaa | ggggcctggc | cgccacctgc | 1980 |
| tcactctcca | gtccttccca | cctctccct | acccttctac | acacgttctc | tttctccctc | 2040 |
| ccgcctccgt | cccctgctgc | cccccgcag | ccctcaccac | ctgccctcct | tctaccagga | 2100 |
| cctcagaagc | ccagacctgg | ggaccccacc | tacacagggg | cattgacaga | ctggagttga | 2160 |

| | | |
|---|---|---|
| aagccgacga | accgacacgc ggcagagtca ataattcaat aaaaaagtta cgaactttct | 2220 |
| ctgtaacttg | ggtttcaata attatggatt tttatgaaaa cttgaaataa taaaaagaga | 2280 |
| aaaaaactat | ttcctatagc tagtcggaat gcaaactttt gacgtcctga ttgctccagg | 2340 |
| gccctcttcc | aactcagttt cttgttttc tcttcctcct cctcctcttc ttcctccttt | 2400 |
| ctcttctctt | ccccagtggg gagggatcac tcaggaaaac aggaaaggag gttccagccc | 2460 |
| cacccacctg | cccaccccgc cccaggcacc atcaggagca ggctagggggg caggcctggg | 2520 |
| cccagctccg | ggctggcttt ttgcagggcg caggtggagg ggacaggtct gccgatgggg | 2580 |
| gtgggagcct | gtctgctggg ctgccaggcg gcaccactgc aagggggtggg agcctggctt | 2640 |
| gggtgtggct | gagactctgg acagaggctg gggtcctcct gggggacagc acagtcagtg | 2700 |
| gagagagcca | ggggctggag gtggggccca ccccagcctc tggtcccagc tctgctgctc | 2760 |
| acttgctgtg | tggcctcaag caggtcactg gcctctctgg gcctcagtct ccacatctgt | 2820 |
| acaaatggga | acattaccc ctgccctgcc tacctcacag ggctgttgtg aggaattgat | 2880 |
| gagatgatgt | atgtgaaaca ctttgtaacc tgtaaagcgc tgtgcacacg tg | 2932 |

<210> SEQ ID NO 6
<211> LENGTH: 2792
<212> TYPE: DNA
<213> ORGANISM: Homo sapiens

<400> SEQUENCE: 6

| | | |
|---|---|---|
| aatttagaga | agatgtaggg agtgttcaac atgttcgttg tggaagagaa agagctaaga | 60 |
| gagaggagct | taaagacaca acgggtaga atcaaggagt gtgctctcaa atgagaggaa | 120 |
| caggagtgac | attaaccttg aaatgctcgg agactctact ccttcatgac agtaggagga | 180 |
| taattaacaa | tagatacaaa tgcaggaatt gatgagtgcc atcagaaagc tgtatcatga | 240 |
| gctgcctgca | cttctaaagt gtccagtgga tttttaatca catgagcctg aaataggggt | 300 |
| tatgaaaaga | agctcagagc agagcaccga aagtggccac taccagcatg aagagcccaa | 360 |
| caattcaaac | tggtgaagtg agaaaaacag aatgcagctt tcaaggttcg tttcaagcag | 420 |
| ttggcttgtg | ggactctgag agatgctgct gcccatgaca tgcgggaatt atcatgatca | 480 |
| actacccagc | ttggatttca tccagtggcc aagagctttg tgtgggagac ggcaagggtt | 540 |
| ggattttca | aaagagtaaa ccaggataaa tcatgaggaa cctataaccc ttttggccac | 600 |
| atgcaaaaaa | gcaagacccg tgaccaaggt gtagactaag aagtggagtc atgcttcaca | 660 |
| cggccatatc | atgctggcag ccattcctgg gtctggctgt ggtgttaatc ttcatgggat | 720 |
| ccaccattgg | ctgccccgct cgctgtgagt gctctgccca gaacaaatct gttagctgtc | 780 |
| acagaaggcg | attgatcgcc atcccagagg gcattcccat cgaaaccaaa atcttggacc | 840 |
| tcagtaaaaa | caggctaaaa agcgtcaacc ctgaagaatt catatcatat cctctgctgg | 900 |
| aagagataga | cttgagtgac aacatcattg ccaatgtgga accaggagca ttcaacaatc | 960 |
| tctttaacct | gcgttccctc cgcctaaaag gcaatcgtct aaagctggtc cctttgggag | 1020 |
| tattcacggg | gctgtccaat ctcactaagc ttgacattag tgagaataag attgtcattt | 1080 |
| tactagacta | catgttccaa gatctacata acctgaagtc tctagaagtg ggggacaatg | 1140 |
| atttggttta | tatatcacac agggcattca gtgggcttct tagcttggag cagctcaccc | 1200 |
| tggagaaatg | caacttaaca gcagtaccaa cagaagccct ctcccacctc cgcagcctca | 1260 |
| tcagcctgca | tctgaagcat ctcaatatca acaatatgcc tgtgtatgcc tttaaaagat | 1320 |

| | |
|---|---|
| tgttccacct gaaacaccta gagattgact attggccttt actggatatg atgcctgcca | 1380 |
| atagcctcta cggtctcaac ctcacatccc tttcagtcac caacaccaat ctgtctactg | 1440 |
| taccottcct tgcctttaaa cacctggtat acctgactca ccttaacctc tcctacaatc | 1500 |
| ccatcagcac tattgaagca ggcatgttct ctgacctgat ccgccttcag gagcttcata | 1560 |
| tagtggggc ccagcttcgc accattgagc ctcactcctt ccaagggctc cgcttcctac | 1620 |
| gcgtgctcaa tgtgtctcag aacctgctgg aaactttgga agagaatgtc ttctcctccc | 1680 |
| ctagggctct ggaggtcttg agcattaaca acaaccctct ggcctgtgac tgccgccttc | 1740 |
| tctggatctt gcagcgacag cccaccctgc agtttggtgg ccagcaacct atgtgtgctg | 1800 |
| gcccagacac catccgtgag aggtctttca aggatttcca tagcactgcc ctttcttttt | 1860 |
| actttacctg caaaaaaccc aaaatccgtg aaagaagtt gcagcatctg ctagtagatg | 1920 |
| aagggcagac agtccagcta gaatgcagtg cagatggaga cccgcagcct gtgatttcct | 1980 |
| gggtgacacc ccgaaggcgt tcatcacca ccaagtccaa tggaagagcc accgtgttgg | 2040 |
| gtgatggcac cttggaaatc cgctttgccc aggatcaaga cagcgggatg tatgtttgca | 2100 |
| tcgctagcaa tgctgctggg aatgataccct tcacagcctc cttaactgtg aaaggattcg | 2160 |
| cttcagatcg ttttctttat gcgaacagga cccctatgta catgaccgac tccaatgaca | 2220 |
| ccatttccaa tggcaccaat gccaatactt tttccctgga ccttaaaaca atactggtgt | 2280 |
| ctacagctat gggctgcttc acattcctgg gagtggtttt attttgtttt cttctcccttt | 2340 |
| ttgtgtggag ccgagggaaa ggcaagcaca aaaacagcat tgaccttgag tatgtgccca | 2400 |
| gaaaaacaa tggtgctgtt gtggaaggag aggtagctgg acccaggagg ttcaacatga | 2460 |
| aaatgatttg aaggcccacc cctcacatta ctgtctcttt gtcaatgtgg gtaatcagta | 2520 |
| agacagtatg gcacagtaaa ttactagatt aagaggcagc catgtgcagc tgcccctgta | 2580 |
| tcaaaagcag ggtctatgga agcaggagga cttccaatgg agactctcca tcgaaaggca | 2640 |
| ggcaggcagg catgtgtcag agcccttcac acagtgggat actaagtgtt tgcgttgcaa | 2700 |
| atattggcgt tctggggatc tcagtaatga acctgaatat ttggctcaca ctcacggaca | 2760 |
| attattcagc attttctacc actgcaaaaa ac | 2792 |

<210> SEQ ID NO 7
<211> LENGTH: 2130
<212> TYPE: DNA
<213> ORGANISM: Homo sapiens

<400> SEQUENCE: 7

| | |
|---|---|
| ggcggcggcg gcggctgctc gtgtcggctc cgggcggccc ccgcgccgca gcccgcgccg | 60 |
| tgtccgcggc ggagccgccc aggtgcgcag gaggatggtg gcgcggccct aggcccacgc | 120 |
| tccgcaccat gacctgctgg ctgtgcgtcc tgagcctgcc cctgctcctg ctgccgcgg | 180 |
| cgccgccccc ggctggaggc tgccggccc gctgcgagtg caccgtgcag acccgcgcgg | 240 |
| tggcctgcac gcgccgccgc ctgaccgccg tgcccgacgg catcccggcc gagacccgcc | 300 |
| tgctggagct cagccgcaac cgcatccgct gcctgaaccc gggcgacctg gccgcgctgc | 360 |
| ccgcgctgga ggagctggac ctgagcgaga acgccatcgc gcacgtggag cccggcgcct | 420 |
| tcgccaacct gccgcgcctg cgcgtcctgc gtctccgtgg caaccagctg aagctcatcc | 480 |
| cgcccgggt cttcacgcgc ctggacaacc tcacgctgct ggacctgagc gagaacaagc | 540 |
| tggtaatcct gctggactac actttccagg acctgcacag cctgcgccgg ctggaagtgg | 600 |
| gcgacaacga cctggtattc gtctcgcgcc gcgccttcgc ggggctgctg gccctggagg | 660 |

```
agctgaccct ggagcgctgc aacctcacgg ctctgtccgg ggagtcgctg ggccatctgc    720
gcagcctggg cgccctgcgg ctgcgccacc tggccatcgc ctccctggag accagaact    780 tccgcaggct gcccgggctg ctgcacctgg agattgacaa ctggccgctg ctggaggagg    840
tggcggcggg cagcctgcgg ggcctgaacc tgacctcgct gtcggtcacc cacaccaaca    900
tcaccgccgt gccggccgcc gcgctgcggc accaggcgca cctcacctgc tcaatctgt    960 cgcacaaccc catcagcacg gtgccgcggg ggtcgttccg ggacctggtc cgcctgcgcg   1020
agctgcacct ggccggggcc ctgctggctg tggtggagcc gcaggccttc ctgggcctgc   1080
gccagatccg cctgctcaac ctctccaaca acctgctctc cacgttggag agagcacct    1140 tccactcggt gaacacgcta gagacgctgc gcgtggacgg aaccccgctg gcctgcgact   1200
gtcgcctgct gtggatcgtg cagcgtcgca agaccctcaa cttcgacggg cggctgccgg   1260
cctgcgccac cccggccgag gtgcgcggcg acgcgctgcg aaacctgccg gactccgtgc   1320
tgttcgagta cttcgtgtgc cgcaaaccca agatccggga gcggcggctg cagcgcgtca   1380
cggccaccgc gggcgaagac gtccgcttcc tctgccgcgc cgagggcgag ccggcgccca   1440
ccgtggcctg ggtgaccccc cagcaccggc cggtgacggc caccagcgcg ggccgggcgc   1500
gcgtgctccc cggggggacg ctggagatcc aggacgcgcg gccgcaggac agcggcacct   1560
acacgtgcgt ggccagcaac gcgggcggca acgacaccta cttcgccacg ctgaccgtgc   1620
gccccgagcc ggccgccaac cggaccccgg gcgaggccca caacgagacg ctggcggccc   1680
tgcgcgcgcc gctcgacctc accaccatcc tggtgtccac cgccatgggc tgcatcacct   1740
tcctgggcgt ggtcctcttc tgcttcgtgc tgctgttcgt gtggagccgc ggccgcgggc   1800
agcacaaaaa caacttctcg gtggagtact ccttccgcaa ggtggatggg ccggccgccg   1860
cggcgggcca gggaggcgcg cgcaagttca acatgaagat gatctgaggg gtccccaggg   1920
cggaccctcc cctccctcc ccgcggcc ggccgctcgc gtgtccacct atgcatttcc   1980
cggaggggaa ggggacggct gcacggcgct ccccaggcag aacttcccct tttttgtag    2040 acgcccaacc gcaggactgt ttttcatcag catgcgtctt ttttgcagtt tctcaagcgt   2100
tttctaaaga tttcaacccg tcttcctgtc                                    2130

<210> SEQ ID NO 8
<211> LENGTH: 2606
<212> TYPE: DNA
<213> ORGANISM: Homo sapiens

<400> SEQUENCE: 8
gcggccgcag cagcaacagc agcagcagca gcggcaggca gcagccgggc agccaggcag     60
cgggggttga ggcacacagg gaaggtgcag gggcctgagg tgcagctcga atgggacagg    120
gcccccagcg ctggacagat gcagtgccaa acttgatgcc accttccagc ttctccggac    180
tgaagaggga atggatgcag ccacagctcc aaagcaagcc tggcccccat ggccccgct     240 ccttttcctc ctcctcctac ctggagggag cggtggcagc tgccctgctg tgtgtgactg    300
cacctcccag ccccaggctg tgctctgtgg ccacaggcaa ctggaggctg tacctggagg    360
actcccactg gacactgagc tcctggacct gagtgggaac cgcctgtggg ggctccagca    420
gggaatgctc tcccgcctga gcctgctcca ggaattggac ctcagctaca accagctctc    480
aacccttgag cctggggcct ccatggcct acaaagccta tcaccctga ggctgcaggg     540 caatcggctc agaatcatgg ggcctggggt cttctcaggc ctctctgctc tgaccctgct   600
```

```
ggacctccgc tcaaccaga ttgttctctt cctagatgga gcttttgggg agctaggcag    660
cctccagaag ctggaggttg gggacaacca cctggtattt gtggctccgg gggcctttgc    720
agggctagcc aagttgagca ccctcaccct ggagcgctgc aacctcagca cagtgcctgg    780
cctagccctt gcccgtctcc cggcactagt ggccctaagg cttagagaac tggatattgg    840
gaggctgcca gctggggccc tgcgggggct ggggcagctc aaggagctgg agatccacct    900
ctggccatct ctggaggctc tggaccctgg gagcctggtt gggctcaatc tcagcagcct    960
ggccatcact cgctgcaatc tgagctcggt gcccttccaa gcactgtacc acctcagctt   1020
cctcagggtc ctggatctgt cccagaatcc catctcagcc atcccagccc gaaggctcag   1080 cccccctggtg cggctccagg agctacgcct gtcaggggca tgcctcacct ccattgctgc   1140
ccatgccttc catggcttga ctgccttcca cctcctggat gtggcagata acgcccttca   1200
gacactagag gaaacagctt tcccttctcc agacaaactg gtcaccttga ggctgtctgg   1260 caaccccta acctgtgact gccgcctcct ctggctgctc cggctccgcc gccacctgga   1320 cttttggcatg tccccccctg cctgtgctgg ccccatcat gtccagggga agagcctgaa   1380
ggagttttca gacatcctgc tccagggca cttcacctgc aaaccagccc tgatccgaaa   1440
gtcggggcct cgatgggtca ttgcagagga gggcgggcat gcggttttct cctgctctgg   1500
agatggagac ccagccccca ctgtctcctg gatgaggcct catggggctt ggctgggcag   1560
ggctgggaga gtaagggtcc tagaggatgg gacactggaa tccgctcag tgcagctacg   1620 ggacagaggg gcctatgtct gtgtggttag caatgtcgct gggaatgact ccctgaggac   1680
ctggctggaa gtcatccagg tggaaccacc aaacggcaca ctttctgacc caacatcac   1740 cgtgccaggg atcccagggc ctttttttct ggatagcaga ggtgtggcca tggtgctggc   1800
agtcggcttc ctccccttcc tcacctcagt gaccctctgc tttggcctga ttgcccttg   1860 gagcaagggc aaaggtcggg tcaaacatca catgaccttt gactttgtgg cacctcggcc   1920
ctctggggat aaaaactctg ggggtaaccg ggtcactgcc aagctcttct gaccttctct   1980
tccccagtgg ggaacccacc aagtccgctt cagataccaa aggggaagac agaaccaagg   2040
ctgcttgaac cagaacctag tcccgagcag caccgctctc ctgcacctcc cgcctgcgtt   2100
gtgcctcctg ccggagagtc tgcttcctga gcttttccgg tctgaggata gcattgtcat   2160
ttcttctctg agggtcccag ggagctgcag atgcagaccc cgttgttagt ccagcccccg   2220
cttcaccccc tccacacaca aaacaggaaa cataatcaaa gcgctagtca gctagtctaa   2280
ccactaggct ttcttcacac atgcttatat ccttttaataa ccaattgcca accacggcta   2340
taagattatt tcagaggtgg ggctgggaag tgccacttgc tccttagagt ctgtttgtca   2400
accaggcaga gtcccttttct tttctgctcc ccacccccaac cctgcccctt tgtacaggaa   2460
taagagcaaa ggacccacag gctacagaga agaggatggg gacagagtgt gggatggaga   2520
ggacagacca tatactgcac tgtgtttgca tgagcctcta ccaccttcct ctatctacca   2580
gatcattaaa cctgctgtca aagggc                                       2606
```

<210> SEQ ID NO 9
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga cccctgaagtt catctgcacc accggcaagc tgcccgtgcc ctggcccacc    180
ctcgtgacca ccttcggcta cggcctgcag tgcttcgccc gctacccga ccacatgaag      240 cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagct accagtccgc cctgagcaaa gaccccaacg agaagcgcga tcacatggtc    660
ctgctggagt tcgtgaccgc cgccgggatc actctcggca tggacgagct gtacaagtaa    720
```

<210> SEQ ID NO 10
<211> LENGTH: 2604
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
atgcaggtga gcaagaggat gctggcgggg ggcgtgagga gcatgcccag ccccctcctg      60
gcctgctggc agcccatcct cctgctggtg ctgggctcag tgctgtcagg ctcggccacg     120
ggctgcccgc ccgctgcga gtgctccgcc caggaccgcg ctgtgctgtg ccaccgcaag     180
cgctttgtgg cagtccccga gggcatcccc accgagacgc gcctgctgga cctaggcaag    240
aaccgcatca aaacgctcaa ccaggacgag ttcgccagct tcccgcacct ggaggagctg    300
gagctcaacg agaacatcgt gagcgccgtg gagcccggcg ccttcaacaa cctcttcaac    360
ctccggacgc tgggtctccg cagcaaccgc ctgaagctca tcccgctagg cgtcttcact    420
ggcctcagca acctgaccaa gctggacatc agcgagaaca gatcgttat cctactggac    480 tacatgtttc aggacctgta caacctcaag tcactggagg ttggcgacaa tgacctcgtc    540
tacatctctc accgcgcctt cagcggcctc aacagcctgg agcagctgac gctggagaaa    600
tgcaacctga cctccatccc caccgaggcg ctgtcccacc tgcacggcct catcgtcctg    660
aggctccggc acctcaacat caatgccatc cgggactact ccttcaagag gctgtaccga    720
ctcaaggtct ggagatctc ccactggccc tacttggaca ccatgacacc caactgcctc    780
tacgccctca acctgacgtc cctgtccatc acacactgca atctgaccgc tgtgccctac    840
ctggccgtcc gccacctagt ctatctccgc ttcctcaacc tctcctacaa ccccatcagc    900
accattgagg gctccatgtt gcatgagctg ctccggctgc aggagatcca gctggtgggc    960
gggcagctgg ccgtggtgga gccctatgcc ttccgcggcc tcaactacct gcgcgtgctc   1020
aatgtctctg caaccagct gaccacactg gaggaatcag tcttccactc ggtgggcaac   1080
ctggagacac tcatcctgga ctccaacccg ctggcctgcg actgtcggct cctgtgggtg   1140
ttccggcgcc gctggcggct caacttcaac cggcagcagc ccacgtgcgc cacgcccgag   1200
tttgtccagg caaggagtt caaggacttc cctgatgtgc tactgcccaa ctacttcacc   1260
tgccgccgcg cccgcatccg ggaccgcaag gcccagcagg tgtttgtgga cgagggccac   1320
```

```
acggtgcagt tgtgtgccg ggccgatggc gacccgccgc ccgccatcct ctggctctca    1380
ccccgaaagc acctggtctc agccaagagc aatgggcggc tcacagtctt ccctgatggc    1440
acgctggagg tgcgctacgc ccaggtacag gacaacggca cgtacctgtg catcgcggcc    1500
aacgcgggcg gcaacgactc catgcccgcc cacctgcatg tgcgcagcta ctcgcccgac    1560 tggcccatc agcccaacaa gaccttcgct ttcatctcca accagccggg cgagggagag    1620
gccaacagca cccgcgccac tgtgcctttc cccttcgaca tcaagaccct catcatcgcc    1680
accaccatgg gcttcatctc tttcctgggc gtcgtcctct tctgcctggt gctgctgttt    1740
ctctggagcc ggggcaaggg caacacaaag cacaacatcg agatcgagta tgtgccccga    1800
aagtcggacg caggcatcag ctccgccgac gcgccccgca agttcaacat gaagatgata    1860
tcacgggatc accggtcgc caccatggtg agcaagggcg aggagctgtt caccggggtg    1920
gtgcccatcc tggtcgagct ggacggcgac gtaaacggcc acaagttcag cgtgtccggc    1980
gagggcgagg gcgatgccac ctacggcaag ctgaccctga agttcatctg caccaccggc    2040
aagctgcccg tgccctggcc cacccctgtg accaccttcg gctacggcct gcagtgcttc    2100
gcccgctacc ccgaccacat gaagcagcac gacttcttca gtccgccat gcccgaaggc    2160 tacgtccagg agcgcaccat cttcttcaag gacgacggca actacaagac ccgcgccgag    2220
gtgaagttcg agggcgacac cctggtgaac cgcatcgagc tgaagggcat cgacttcaag    2280
gaggacggca acatcctggg gcacaagctg gagtacaact acaacagcca caacgtctat    2340
atcatggccg acaagcagaa gaacggcatc aaggtgaact tcaagatccg ccacaacatc    2400
gaggacggca gcgtgcagct cgccgaccac taccagcaga caccccat cggcgacggc    2460 cccgtgctgc tgcccgacaa ccactacctg agctaccagt ccgccctgag caaagacccc    2520
aacgagaagc gcgatcacat ggtcctgctg gagttcgtga ccgccgccgg gatcactctc    2580
ggcatggacg agctgtacaa gtaa    2604
```

<210> SEQ ID NO 11
<211> LENGTH: 867
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
Met Gln Val Ser Lys Arg Met Leu Ala Gly Gly Val Arg Ser Met Pro
1               5                   10                  15

Ser Pro Leu Leu Ala Cys Trp Gln Pro Ile Leu Leu Val Leu Leu Gly
            20                  25                  30

Ser Val Leu Ser Gly Ser Ala Thr Gly Cys Pro Pro Arg Cys Glu Cys
        35                  40                  45

Ser Ala Gln Asp Arg Ala Val Leu Cys His Arg Lys Arg Phe Val Ala
    50                  55                  60

Val Pro Glu Gly Ile Pro Thr Glu Thr Arg Leu Leu Asp Leu Gly Lys
65                  70                  75                  80

Asn Arg Ile Lys Thr Leu Asn Gln Asp Glu Phe Ala Ser Phe Pro His
                85                  90                  95

Leu Glu Glu Leu Glu Leu Asn Glu Asn Ile Val Ser Ala Val Glu Pro
            100                 105                 110

Gly Ala Phe Asn Asn Leu Phe Asn Leu Arg Thr Leu Gly Leu Arg Ser
        115                 120                 125
```

```
Asn Arg Leu Lys Leu Ile Pro Leu Gly Val Phe Thr Gly Leu Ser Asn
    130                 135                 140

Leu Thr Lys Leu Asp Ile Ser Glu Asn Lys Ile Val Ile Leu Leu Asp
145                 150                 155                 160

Tyr Met Phe Gln Asp Leu Tyr Asn Leu Lys Ser Leu Glu Val Gly Asp
                165                 170                 175

Asn Asp Leu Val Tyr Ile Ser His Arg Ala Phe Ser Gly Leu Asn Ser
                180                 185                 190

Leu Glu Gln Leu Thr Leu Glu Lys Cys Asn Leu Thr Ser Ile Pro Thr
        195                 200                 205

Glu Ala Leu Ser His Leu His Gly Leu Ile Val Leu Arg Leu Arg His
210                 215                 220

Leu Asn Ile Asn Ala Ile Arg Asp Tyr Ser Phe Lys Arg Leu Tyr Arg
225                 230                 235                 240

Leu Lys Val Leu Glu Ile Ser His Trp Pro Tyr Leu Asp Thr Met Thr
                245                 250                 255

Pro Asn Cys Leu Tyr Gly Leu Asn Leu Thr Ser Leu Ser Ile Thr His
                260                 265                 270

Cys Asn Leu Thr Ala Val Pro Tyr Leu Ala Val Arg His Leu Val Tyr
        275                 280                 285

Leu Arg Phe Leu Asn Leu Ser Tyr Asn Pro Ile Ser Thr Ile Glu Gly
290                 295                 300

Ser Met Leu His Glu Leu Leu Arg Leu Gln Glu Ile Gln Leu Val Gly
305                 310                 315                 320

Gly Gln Leu Ala Val Val Glu Pro Tyr Ala Phe Arg Gly Leu Asn Tyr
                325                 330                 335

Leu Arg Val Leu Asn Val Ser Gly Asn Gln Leu Thr Thr Leu Glu Glu
                340                 345                 350

Ser Val Phe His Ser Val Gly Asn Leu Glu Thr Leu Ile Leu Asp Ser
        355                 360                 365

Asn Pro Leu Ala Cys Asp Cys Arg Leu Leu Trp Val Phe Arg Arg Arg
370                 375                 380

Trp Arg Leu Asn Phe Asn Arg Gln Gln Pro Thr Cys Ala Thr Pro Glu
385                 390                 395                 400

Phe Val Gln Gly Lys Glu Phe Lys Asp Phe Pro Asp Val Leu Leu Pro
                405                 410                 415

Asn Tyr Phe Thr Cys Arg Arg Ala Arg Ile Arg Asp Arg Lys Ala Gln
                420                 425                 430

Gln Val Phe Val Asp Glu Gly His Thr Val Gln Phe Val Cys Arg Ala
        435                 440                 445

Asp Gly Asp Pro Pro Ala Ile Leu Trp Leu Ser Pro Arg Lys His
450                 455                 460

Leu Val Ser Ala Lys Ser Asn Gly Arg Leu Thr Val Phe Pro Asp Gly
465                 470                 475                 480

Thr Leu Glu Val Arg Tyr Ala Gln Val Gln Asp Asn Gly Thr Tyr Leu
                485                 490                 495

Cys Ile Ala Ala Asn Ala Gly Gly Asn Asp Ser Met Pro Ala His Leu
                500                 505                 510

His Val Arg Ser Tyr Ser Pro Asp Trp Pro His Gln Pro Asn Lys Thr
        515                 520                 525

Phe Ala Phe Ile Ser Asn Gln Pro Gly Glu Gly Glu Ala Asn Ser Thr
530                 535                 540

Arg Ala Thr Val Pro Phe Pro Phe Asp Ile Lys Thr Leu Ile Ile Ala
```

```
                       545                 550                 555                 560
                   Thr Thr Met Gly Phe Ile Ser Phe Leu Gly Val Val Leu Phe Cys Leu
                                   565                 570                 575
                   Val Leu Leu Phe Leu Trp Ser Arg Gly Lys Gly Asn Thr Lys His Asn
                                   580                 585                 590
                   Ile Glu Ile Glu Tyr Val Pro Arg Lys Ser Asp Ala Gly Ile Ser Ser
                                   595                 600                 605
                   Ala Asp Ala Pro Arg Lys Phe Asn Met Lys Met Ile Ser Arg Asp Pro
                                   610                 615                 620
                   Pro Val Ala Thr Met Val Ser Lys Gly Glu Glu Leu Phe Thr Gly Val
                   625                 630                 635                 640
                   Val Pro Ile Leu Val Glu Leu Asp Gly Asp Val Asn Gly His Lys Phe
                                   645                 650                 655
                   Ser Val Ser Gly Glu Gly Glu Gly Asp Ala Thr Tyr Gly Lys Leu Thr
                                   660                 665                 670
                   Leu Lys Phe Ile Cys Thr Thr Gly Lys Leu Pro Val Pro Trp Pro Thr
                                   675                 680                 685
                   Leu Val Thr Thr Phe Gly Tyr Gly Leu Gln Cys Phe Ala Arg Tyr Pro
                                   690                 695                 700
                   Asp His Met Lys Gln His Asp Phe Phe Lys Ser Ala Met Pro Glu Gly
                   705                 710                 715                 720
                   Tyr Val Gln Glu Arg Thr Ile Phe Phe Lys Asp Asp Gly Asn Tyr Lys
                                   725                 730                 735
                   Thr Arg Ala Glu Val Lys Phe Glu Gly Asp Thr Leu Val Asn Arg Ile
                                   740                 745                 750
                   Glu Leu Lys Gly Ile Asp Phe Lys Glu Asp Gly Asn Ile Leu Gly His
                                   755                 760                 765
                   Lys Leu Glu Tyr Asn Tyr Asn Ser His Asn Val Tyr Ile Met Ala Asp
                                   770                 775                 780
                   Lys Gln Lys Asn Gly Ile Lys Val Asn Phe Lys Ile Arg His Asn Ile
                   785                 790                 795                 800
                   Glu Asp Gly Ser Val Gln Leu Ala Asp His Tyr Gln Gln Asn Thr Pro
                                   805                 810                 815
                   Ile Gly Asp Gly Pro Val Leu Leu Pro Asp Asn His Tyr Leu Ser Tyr
                                   820                 825                 830
                   Gln Ser Ala Leu Ser Lys Asp Pro Asn Glu Lys Arg Asp His Met Val
                                   835                 840                 845
                   Leu Leu Glu Phe Val Thr Ala Ala Gly Ile Thr Leu Gly Met Asp Glu
                                   850                 855                 860
                   Leu Tyr Lys
                   865

<210> SEQ ID NO 12
<211> LENGTH: 936
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atgaccagca aggtgtacga ccccgagcag aggaagagga tgatcaccgg cccccagtgg      60
tgggccaggt gcaagcagat gaacgtgctg acagcttca tcaactacta cgacagcgag      120
aagcacgccg agaacgccgt gatcttcctg cacggcaacg ccgctagtag ctacctgtgg     180
```

-continued

| | |
|---|---|
| aggcacgtgg tgccccacat cgagcccgtg gccaggtgca tcatccccga tctgatcggc | 240 |
| atgggcaaga gcggcaagag cggcaacggc agctacaggc tgctggacca ctacaagtac | 300 |
| ctgaccgcct ggttcgagct cctgaacctg cccaagaaga tcatcttcgt gggccacgac | 360 |
| tggggcgcct gcctggcctt ccactacagc tacgagcacc aggacaagat caaggccatc | 420 |
| gtgcacgccg agagcgtggt ggacgtgatc gagagctggg acgagtggcc agacatcgag | 480 |
| gaggacatcg ccctgatcaa gagcgaggag ggcgagaaga tggtgctgga gaacaacttc | 540 |
| ttcgtggaga ccatgctgcc cagcaagatc atgagaaagc tggagcccga ggagttcgcc | 600 |
| gcctacctgg agcccttcaa ggagaagggc gaggtgagaa gacccacccct gagctggccc | 660 |
| agagagatcc ccctggtgaa gggcggcaag cccgacgtgg tgcagatcgt gagaaactac | 720 |
| aacgcctacc tgagagccag cgacgacctg cccaagatgt tcatcgagag cgaccccggc | 780 |
| ttcttcagca cgccatcgt ggagggcgcc aagaagttcc ccaacaccga gttcgtgaag | 840 |
| gtgaagggcc tgcacttcag ccaggaggac gcccccgacg agatgggcaa gtacatcaag | 900 |
| agcttcgtgg agagagtgct gaagaacgag cagtaa | 936 |

<210> SEQ ID NO 13
<211> LENGTH: 2820
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

| | |
|---|---|
| atgcaggtga gcaagaggat gctggcgggg ggcgtgagga gcatgcccag ccccctcctg | 60 |
| gcctgctggc agcccatcct cctgctggtg ctgggctcag tgctgtcagg ctcggccacg | 120 |
| ggctgcccgc ccgctgcga gtgctccgcc caggaccgcc tgtgctgtg ccaccgcaag | 180 |
| cgctttgtgg cagtccccga gggcatcccc accgagacgc gcctgctgga cctaggcaag | 240 |
| aaccgcatca aaacgctcaa ccaggacgag ttcgccagct cccgcacct ggaggagctg | 300 |
| gagctcaacg agaacatcgt gagcgccgtg gagcccggcg ccttcaacaa cctcttcaac | 360 |
| ctccggacgc tgggtctccg cagcaaccgc ctgaagctca tccgctagg cgtcttcact | 420 |
| ggcctcagca acctgaccaa gctggacatc agcgagaaca agatcgttat cctactggac | 480 |
| tacatgtttc aggacctgta caacctcaag tcactggagg ttggcgacaa tgacctcgtc | 540 |
| tacatctctc accgcgcctt cagcggcctc aacagcctgg agcagctgac gctggagaaa | 600 |
| tgcaacctga cctccatccc caccgaggcg ctgtcccacc tgcacggcct catcgtcctg | 660 |
| aggctccggc acctcaacat caatgccatc cgggactact ccttcaagag gctgtaccga | 720 |
| ctcaaggtct ggagatctct ccactggccc tacttggaca ccatgacacc caactgcctc | 780 |
| tacggcctca acctgacgtc cctgtccatc acacactgca atctgaccgc tgtgccctac | 840 |
| ctggccgtcc gccacctagt ctatctccgc ttcctcaacc tctcctacaa ccccatcagc | 900 |
| accattgagg gctccatgtt gcatgagctg ctccggctgc aggagatcca gctggtgggc | 960 |
| gggcagctgg ccgtggtgga gccctatgcc ttcgcggcc tcaactacct gcgcgtgctc | 1020 |
| aatgtctctg caaccagct gaccacactg gaggaatcag tcttccactc ggtgggcaac | 1080 |
| ctggagacac tcatcctgga ctccaacccg ctggcctgcg actgtcggct cctgtgggtg | 1140 |
| ttccggcgcc gctggcggct caacttcaac cggcagcagc ccacgtgcgc cacgcccgag | 1200 |
| tttgtccagg gcaaggagtt caaggacttc cctgatgtgc tactgcccaa ctacttcacc | 1260 |

```
tgccgccgcg cccgcatccg ggaccgcaag gcccagcagg tgtttgtgga cgagggccac    1320
acggtgcagt ttgtgtgccg ggccgatggc gacccgccgc cgccatcctc tggctctca    1380 ccccgaaagc acctggtctc agccaagagc aatgggcggc tcacagtctt ccctgatggc    1440
acgctggagt gcgctacgc ccaggtacag acaacggca cgtacctgtg catcgcggcc    1500
aacgcgggcg gcaacgactc catgcccgcc cacctgcatg tgcgcagcta ctcgcccgac    1560 tggcccatc agcccaacaa gaccttcgct ttcatctcca accagccggg cgagggagag    1620
gccaacagca cccgcgccac tgtgcctttc cccttcgaca tcaagaccct catcatcgcc    1680
accaccatgg gcttcatctc tttcctgggc gtcgtcctct tctgcctggt gctgctgttt    1740
ctctggagcc ggggcaaggg caacacaaag cacaacatcg agatcgagta tgtgccccga    1800
aagtcggacg caggcatcag ctccgccgac gcgccccgca gttcaacat gaagatgata    1860 tcacgggatc caccggtagc aaccatgacc agcaaggtgt acgaccccga gcagaggaag    1920
aggatgatca ccggcccca gtggtgggc aggtgcaagc agatgaacgt gctggacagc    1980
ttcatcaact actacgacag cgagaagcac gccgagaacg ccgtgatctt cctgcacggc    2040
aacgccgcta gtagctacct gtggaggcac gtggtgcccc acatcgagcc cgtggccagg    2100
tgcatcatcc ccgatctgat cggcatgggc aagagcggca gagcggcaa cggcagctac    2160 aggctgctgg accactacaa gtacctgacc gcctggttcg agctcctgaa cctgcccaag    2220
aagatcatct tcgtgggcca cgactgggc gcctgcctgg ccttccacta cagctacgag    2280
caccaggaca agatcaaggc catcgtgcac gccgagagcg tggtggacgt gatcgagagc    2340
tgggacgagt ggccagacat cgaggaggac atcgccctga tcaagagcga ggagggcgag    2400
aagatggtgc tggagaacaa cttcttcgtg gagaccatgc tgcccagcaa gatcatgaga    2460
aagctggagc ccgaggagtt cgccgcctac ctggagccct tcaaggagaa gggcgaggtg    2520
agaagaccca ccctgagctg gccagagag atccccctgg tgaagggcgg caagcccgac    2580
gtggtgcaga tcgtgagaaa ctacaacgcc tacctgagag ccagcgacga cctgcccaag    2640
atgttcatcg agagcgaccc cggcttcttc agcaacgcca tcgtggaggg cgccaagaag    2700
ttccccaaca ccgagttcgt gaaggtgaag ggcctgcact tcagccagga ggacgccccc    2760
gacgagatgg gcaagtacat caagagcttc gtggagagag tgctgaagaa cgagcagtaa    2820
```

<210> SEQ ID NO 14
<211> LENGTH: 939
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Gln Val Ser Lys Arg Met Leu Ala Gly Gly Val Arg Ser Met Pro
1               5                   10                  15

Ser Pro Leu Leu Ala Cys Trp Gln Pro Ile Leu Leu Val Leu Gly
            20                  25                  30

Ser Val Leu Ser Gly Ser Ala Thr Gly Cys Pro Pro Arg Cys Glu Cys
        35                  40                  45

Ser Ala Gln Asp Arg Ala Val Leu Cys His Arg Lys Arg Phe Val Ala
    50                  55                  60

Val Pro Glu Gly Ile Pro Thr Glu Thr Arg Leu Leu Asp Leu Gly Lys
65                  70                  75                  80

Asn Arg Ile Lys Thr Leu Asn Gln Asp Glu Phe Ala Ser Phe Pro His

```
            85                  90                  95
Leu Glu Glu Leu Glu Leu Asn Glu Asn Ile Val Ser Ala Val Glu Pro
            100                 105                 110

Gly Ala Phe Asn Asn Leu Phe Asn Leu Arg Thr Leu Gly Leu Arg Ser
            115                 120                 125

Asn Arg Leu Lys Leu Ile Pro Leu Gly Val Phe Thr Gly Leu Ser Asn
        130                 135                 140

Leu Thr Lys Leu Asp Ile Ser Glu Asn Lys Ile Val Ile Leu Leu Asp
145                 150                 155                 160

Tyr Met Phe Gln Asp Leu Tyr Asn Leu Lys Ser Leu Glu Val Gly Asp
                165                 170                 175

Asn Asp Leu Val Tyr Ile Ser His Arg Ala Phe Ser Gly Leu Asn Ser
            180                 185                 190

Leu Glu Gln Leu Thr Leu Glu Lys Cys Asn Leu Thr Ser Ile Pro Thr
            195                 200                 205

Glu Ala Leu Ser His Leu His Gly Leu Ile Val Leu Arg Leu Arg His
        210                 215                 220

Leu Asn Ile Asn Ala Ile Arg Asp Tyr Ser Phe Lys Arg Leu Tyr Arg
225                 230                 235                 240

Leu Lys Val Leu Glu Ile Ser His Trp Pro Tyr Leu Asp Thr Met Thr
                245                 250                 255

Pro Asn Cys Leu Tyr Gly Leu Asn Leu Thr Ser Leu Ser Ile Thr His
            260                 265                 270

Cys Asn Leu Thr Ala Val Pro Tyr Leu Ala Val Arg His Leu Val Tyr
            275                 280                 285

Leu Arg Phe Leu Asn Leu Ser Tyr Asn Pro Ile Ser Thr Ile Glu Gly
        290                 295                 300

Ser Met Leu His Glu Leu Leu Arg Leu Gln Glu Ile Gln Leu Val Gly
305                 310                 315                 320

Gly Gln Leu Ala Val Val Glu Pro Tyr Ala Phe Arg Gly Leu Asn Tyr
                325                 330                 335

Leu Arg Val Leu Asn Val Ser Gly Asn Gln Leu Thr Thr Leu Glu Glu
            340                 345                 350

Ser Val Phe His Ser Val Gly Asn Leu Glu Thr Leu Ile Leu Asp Ser
            355                 360                 365

Asn Pro Leu Ala Cys Asp Cys Arg Leu Leu Trp Val Phe Arg Arg Arg
        370                 375                 380

Trp Arg Leu Asn Phe Asn Arg Gln Gln Pro Thr Cys Ala Thr Pro Glu
385                 390                 395                 400

Phe Val Gln Gly Lys Glu Phe Lys Asp Phe Pro Asp Val Leu Leu Pro
                405                 410                 415

Asn Tyr Phe Thr Cys Arg Arg Ala Arg Ile Arg Asp Arg Lys Ala Gln
            420                 425                 430

Gln Val Phe Val Asp Glu Gly His Thr Val Gln Phe Val Cys Arg Ala
        435                 440                 445

Asp Gly Asp Pro Pro Ala Ile Leu Trp Leu Ser Pro Arg Lys His
450                 455                 460

Leu Val Ser Ala Lys Ser Asn Gly Arg Leu Thr Val Phe Pro Asp Gly
465                 470                 475                 480

Thr Leu Glu Val Arg Tyr Ala Gln Val Gln Asp Asn Gly Thr Tyr Leu
                485                 490                 495

Cys Ile Ala Ala Asn Ala Gly Gly Asn Asp Ser Met Pro Ala His Leu
            500                 505                 510
```

```
His Val Arg Ser Tyr Ser Pro Asp Trp Pro His Gln Pro Asn Lys Thr
            515                 520                 525

Phe Ala Phe Ile Ser Asn Gln Pro Gly Glu Gly Glu Ala Asn Ser Thr
530                 535                 540

Arg Ala Thr Val Pro Phe Pro Phe Asp Ile Lys Thr Leu Ile Ile Ala
545                 550                 555                 560

Thr Thr Met Gly Phe Ile Ser Phe Leu Gly Val Val Leu Phe Cys Leu
                565                 570                 575

Val Leu Leu Phe Leu Trp Ser Arg Gly Lys Gly Asn Thr Lys His Asn
            580                 585                 590

Ile Glu Ile Glu Tyr Val Pro Arg Lys Ser Asp Ala Gly Ile Ser Ser
        595                 600                 605

Ala Asp Ala Pro Arg Lys Phe Asn Met Lys Met Ile Ser Arg Asp Pro
        610                 615                 620

Pro Val Ala Thr Met Thr Ser Lys Val Tyr Asp Pro Glu Gln Arg Lys
625                 630                 635                 640

Arg Met Ile Thr Gly Pro Gln Trp Trp Ala Arg Cys Lys Gln Met Asn
                645                 650                 655

Val Leu Asp Ser Phe Ile Asn Tyr Tyr Asp Ser Glu Lys His Ala Glu
            660                 665                 670

Asn Ala Val Ile Phe Leu His Gly Asn Ala Ala Ser Ser Tyr Leu Trp
        675                 680                 685

Arg His Val Val Pro His Ile Glu Pro Val Ala Arg Cys Ile Ile Pro
        690                 695                 700

Asp Leu Ile Gly Met Gly Lys Ser Gly Lys Ser Gly Asn Gly Ser Tyr
705                 710                 715                 720

Arg Leu Leu Asp His Tyr Lys Tyr Leu Thr Ala Trp Phe Glu Leu Leu
                725                 730                 735

Asn Leu Pro Lys Lys Ile Ile Phe Val Gly His Asp Trp Gly Ala Cys
            740                 745                 750

Leu Ala Phe His Tyr Ser Tyr Glu His Gln Asp Lys Ile Lys Ala Ile
        755                 760                 765

Val His Ala Glu Ser Val Val Asp Val Ile Glu Ser Trp Asp Glu Trp
        770                 775                 780

Pro Asp Ile Glu Glu Asp Ile Ala Leu Ile Lys Ser Glu Glu Gly Glu
785                 790                 795                 800

Lys Met Val Leu Glu Asn Asn Phe Phe Val Glu Thr Met Leu Pro Ser
                805                 810                 815

Lys Ile Met Arg Lys Leu Glu Pro Glu Glu Phe Ala Ala Tyr Leu Glu
            820                 825                 830

Pro Phe Lys Glu Lys Gly Glu Val Arg Arg Pro Thr Leu Ser Trp Pro
        835                 840                 845

Arg Glu Ile Pro Leu Val Lys Gly Gly Lys Pro Asp Val Val Gln Ile
        850                 855                 860

Val Arg Asn Tyr Asn Ala Tyr Leu Arg Ala Ser Asp Asp Leu Pro Lys
865                 870                 875                 880

Met Phe Ile Glu Ser Asp Pro Gly Phe Phe Ser Asn Ala Ile Val Glu
                885                 890                 895

Gly Ala Lys Lys Phe Pro Asn Thr Glu Phe Val Lys Val Lys Gly Leu
            900                 905                 910

His Phe Ser Gln Glu Asp Ala Pro Asp Glu Met Gly Lys Tyr Ile Lys
        915                 920                 925
```

Ser Phe Val Glu Arg Val Leu Lys Asn Glu Gln
    930                 935

<210> SEQ ID NO 15
<211> LENGTH: 4960
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta caactccgcc ccattgacgc aaatgggcgg taggcgtgt    540 acggtgggag gtctatataa gcagagctgg tttagtgaac cgtcagatcc gctagcgcta    600
ccggactcag atctcgagct caagcttcga attctgcagt cgacggtacc gcgggcccgg    660
gatccaccgg tagcaaccat gaccagcaag gtgtacgacc ccgagcagag gaagaggatg    720
atcaccggcc cccagtggtg ggccaggtgc aagcagatga acgtgctgga cagcttcatc    780
aactactacg acagcgagaa gcacgccgag aacgccgtga tcttcctgca cggcaacgcc    840
gctagtagct acctgtggag gcacgtggtg ccccacatcg agcccgtggc caggtgcatc    900
atccccgatc tgatcggcat gggcaagagc ggcaagagcg gcaacggcag ctacaggctg    960
ctggaccact acaagtacct gaccgcctgg ttcgagctcc tgaacctgcc caagaagatc   1020
atcttcgtgg gccacgactg gggcgcctgc ctggccttcc actacagcta cgagcaccag   1080
gacaagatca aggccatcgt gcacgccgag agcgtggtgg acgtgatcga gagctgggac   1140
gagtggccag acatcgagga ggacatcgcc ctgatcaaga gcgaggaggg cgagaagatg   1200
gtgctggaga caaacttctt cgtggagacc atgctgccca gcaagatcat gagaaagctg   1260
gagcccgagg agttcgccgc ctacctggag cccttcaagg agaagggcga ggtgagaaga   1320 cccacccctga gctggcccag agagatcccc ctggtgaagg gcggcaagcc cgacgtggtg   1380
cagatcgtga gaaactacaa cgcctacctg agagccagcg acgacctgcc caagatgttc   1440
atcgagagcg accccggctt cttcagcaac gccatcgtgg agggcgccaa gaagttcccc   1500
aacaccgagt tcgtgaaggt gaagggcctg cacttcagcc aggaggacgc ccccgacgag   1560
atgggcaagt acatcaagag cttcgtggag agagtgctga agaacgagca gtaatgtaca   1620
agtaaagcgg ccgcgactct agatcataat cagccatacc acatttgtag aggttttact   1680
tgctttaaaa aacctcccac acctcccct gaacctgaaa cataaaatga atgcaattgt   1740
tgttgttaac ttgtttattg cagcttataa tggttacaaa taaagcaata gcatcacaaa   1800
tttcacaaat aaagcatttt ttcactgca ttctagttgt ggtttgtcca aactcatcaa   1860
tgtatcttaa ggcgtaaatt gtaagcgtta atatttgtt aaaattcgcg ttaaattttt   1920
gttaaatcag ctcattttt aaccaatagg ccgaaatcgg caaaatccct tataaatcaa   1980

```
aagaatagac cgagatalggg ttgagtgttg ttccagtttg gaacaagagt ccactattaa    2040
agaacgtgga ctccaacgtc aaagggcgaa aaaccgtcta tcagggcgat ggcccactac    2100
gtgaaccatc accctaatca agttttttgg ggtcgaggtg ccgtaaagca ctaaatcgga    2160
accctaaagg gagcccccga tttagagctt gacggggaaa gccggcgaac gtggcgagaa    2220
aggaagggaa gaaagcgaaa ggagcgggcg ctagggcgct ggcaagtgta gcggtcacgc    2280
tgcgcgtaac caccacaccc gccgcgctta atgcgccgct acagggcgcg tcaggtggca    2340
cttttcgggg aaatgtgcgc ggaaccccta tttgtttatt tttctaaata cattcaaata    2400
tgtatccgct catgagacaa taaccctgat aaatgcttca ataatattga aaaaggaaga    2460
gtcctgaggc ggaaagaacc agctgtggaa tgtgtgtcag ttagggtgtg gaaagtcccc    2520
aggctcccca gcaggcagaa gtatgcaaag catgcatctc aattagtcag caaccaggtg    2580
tggaaagtcc ccaggctccc cagcaggcag aagtatgcaa agcatgcatc tcaattagtc    2640
agcaaccata gtcccgcccc taactccgcc catcccgccc ctaactccgc ccagttccgc    2700
ccattctccg ccccatggct gactaatttt ttttatttat gcagaggccg aggccgcctc    2760
ggcctctgag ctattccaga agtagtgagg aggcttttt ggaggcctag gcttttgcaa    2820
agatcgatca agagacagga tgaggatcgt ttcgcatgat tgaacaagat ggattgcacg    2880
caggttctcc ggccgcttgg gtggagaggc tattcggcta tgactgggca acagacaa    2940 tcggctgctc tgatgccgcc gtgttccggc tgtcagcgca ggggcgcccg gttcttttg    3000 tcaagaccga cctgtccggt gccctgaatg aactgcaaga cgaggcagcg cggctatcgt    3060
ggctggccac gacgggcgtt ccttgcgcag ctgtgctcga cgttgtcact gaagcgggaa    3120
gggactggct gctattgggc gaagtgccgg ggcaggatct cctgtcatct caccttgctc    3180
ctgccgagaa agtatccatc atggctgatg caatgcggcg gctgcatacg cttgatccgg    3240
ctacctgccc attcgaccac caagcgaaac atcgcatcga gcgagcacgt actcggatgg    3300
aagccggtct tgtcgatcag gatgatctgg acgaagagca tcaggggctc gcgccagccg    3360
aactgttcgc caggctcaag gcgagcatgc ccgacggcga ggatctcgtc gtgacccatg    3420
gcgatgcctg cttgccgaat atcatggtgg aaaatggccg cttttctgga ttcatcgact    3480
gtggccggct gggtgtggcg gaccgctatc aggacatagc gttggctacc cgtgatattg    3540
ctgaagagct tggcggcgaa tgggctgacc gcttcctcgt gctttacggt atcgccgctc    3600
ccgattcgca gcgcatcgcc ttctatcgcc ttcttgacga gttcttctga gcgggactct    3660
ggggttcgaa atgaccgacc aagcgacgcc caacctgcca tcacgagatt tcgattccac    3720
cgccgccttc tatgaaaggt tgggcttcgg aatcgttttc cgggacgccg gctggatgat    3780
cctccagcgc ggggatctca tgctggagtt cttcgcccac cctaggggga ggctaactga    3840
aacacggaag gagacaatac cggaaggaac ccgcgctatg acggcaataa aaagacagaa    3900
taaaacgcac ggtgttgggt cgtttgttca taaacgcggg gttcggtccc agggctggca    3960
ctctgtcgat accccaccga ccccattg ggccaatac gcccgcgttt cttcctttc     4020 cccaccccac cccccaagtt cgggtgaagg cccagggctc gcagccaacg tcggggcggc    4080
aggccctgcc atagcctcag gttactcata tatactttag attgatttaa aacttcatt    4140 ttaatttaaa aggatctagg tgaagatcct ttttgataat ctcatgacca aaatccctta    4200
acgtgagttt tcgttccact gagcgtcaga ccccgtagaa aagatcaaag gatcttcttg    4260
agatcctttt tttctgcgcg taatctgctg cttgcaaaca aaaaaaccac cgctaccagc    4320
```

-continued

```
ggtggtttgt ttgccggatc aagagctacc aactcttttt ccgaaggtaa ctggcttcag    4380
cagagcgcag ataccaaata ctgtccttct agtgtagccg tagttaggcc accacttcaa    4440
gaactctgta gcaccgccta catacctcgc tctgctaatc ctgttaccag tggctgctgc    4500
cagtggcgat aagtcgtgtc ttaccgggtt ggactcaaga cgatagttac cggataaggc    4560
gcagcggtcg ggctgaacgg ggggttcgtg cacacagccc agcttggagc gaacgaccta    4620
caccgaactg agatacctac agcgtgagct atgagaaagc gccacgcttc ccgaagggag    4680
aaaggcggac aggtatccgg taagcggcag ggtcggaaca ggagagcgca cgagggagct    4740
tccaggggga aacgcctggt atctttatag tcctgtcggg tttcgccacc tctgacttga    4800
gcgtcgattt ttgtgatgct cgtcaggggg gcggagccta tggaaaaacg ccagcaacgc    4860
ggccttttta cggttcctgg ccttttgctg gccttttgct cacatgttct ttcctgcgtt    4920
atcccctgat tctgtggata accgtattac cgccatgcat                          4960
```

<210> SEQ ID NO 16
<211> LENGTH: 4733
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

```
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta caactccgcc ccattgacg caaatgggcg gtaggcgtgt    540
acggtgggag gtctatataa gcagagctgg tttagtgaac cgtcagatcc gctagcgcta    600
ccggactcag atctcgagct caagcttcga attctgcagt cgacggtacc gcgggcccgg    660
gatccaccgg tcgccaccat ggtgagcaag ggcgaggagc tgttcaccgg ggtggtgccc    720
atcctggtcg agctggacgg cgacgtaaac ggccacaagt tcagcgtgtc cggcgagggc    780
gagggcgatg ccacctacgg caagctgacc ctgaagttca tctgcaccac cggcaagctg    840
cccgtgccct ggcccaccct cgtgaccacc ttcggctacg gcctgcagtg cttcgcccgc    900
taccccgacc acatgaagca gcacgacttc ttcaagtccg ccatgcccga aggctacgtc    960
caggagcgca ccatcttctt caaggacgac ggcaactaca agacccgcgc cgaggtgaag   1020
ttcgagggcg acaccctggt gaaccgcatc gagctgaagg gcatcgactt caaggaggac   1080
ggcaacatcc tggggcacaa gctggagtac aactacaaca gccacaacgt ctatatcatg   1140
gccgacaagc agaagaacgg catcaaggtg aacttcaaga tccgccacaa catcgaggac   1200
ggcagcgtgc agctcgccga ccactaccag cagaacaccc ccatcggcga cggccccgtg   1260
ctgctgcccg acaaccacta cctgagctac cagtccgccc tgagcaaaga ccccaacgag   1320
aagcgcgatc acatggtcct gctggagttc gtgaccgccg ccgggatcac tctcggcatg   1380
```

```
gacgagctgt acaagtaaag cggccgcgac tctagatcat aatcagccat accacatttg    1440
tagaggtttt acttgcttta aaaaacctcc cacacctccc cctgaacctg aaacataaaa    1500
tgaatgcaat tgttgttgtt aacttgttta ttgcagctta taatggttac aaataaagca    1560
atagcatcac aaatttcaca aataaagcat tttttcact gcattctagt tgtggtttgt     1620
ccaaactcat caatgtatct taaggcgtaa attgtaagcg ttaatatttt gttaaaattc    1680
gcgttaaatt tttgttaaat cagctcattt tttaaccaat aggccgaaat cggcaaaatc    1740
ccttataaat caaaagaata gaccgagata gggttgagtg ttgttccagt ttggaacaag    1800
agtccactat taagaacgt ggactccaac gtcaaagggc gaaaaaccgt ctatcagggc      1860
gatggcccac tacgtgaacc atcaccctaa tcaagttttt tggggtcgag gtgccgtaaa    1920
gcactaaatc ggaaccctaa agggagcccc cgatttagag cttgacgggg aaagccggcg    1980
aacgtggcga gaaaggaagg gaagaaagcg aaaggagcgg gcgctagggc gctggcaagt    2040
gtagcggtca cgctgcgcgt aaccaccaca cccgccgcgc ttaatgcgcc gctacagggc    2100
gcgtcaggtg gcacttttcg gggaaatgtg cgcggaaccc ctatttgttt attttctaa    2160 atacattcaa atatgtatcc gctcatgaga caataaccct gataaatgct tcaataatat    2220
tgaaaaagga gagtcctga ggcggaaaga accagctgtg gaatgtgtgt cagttagggt      2280
gtggaaagtc cccaggctcc ccagcaggca gaagtatgca aagcatgcat ctcaattagt    2340
cagcaaccag gtgtggaaag tccccaggct ccccagcagg cagaagtatg caaagcatgc    2400
atctcaatta gtcagcaacc atagtcccgc ccctaactcc gcccatcccg cccctaactc    2460
cgcccagttc cgcccattct ccgccccatg gctgactaat tttttttatt tatgcagagg    2520
ccgaggccgc ctcggcctct gagctattcc agaagtagtg aggaggcttt tttggaggcc    2580
taggcttttg caaagatcga tcaagagaca ggatgaggat cgtttcgcat gattgaacaa    2640
gatggattgc acgcaggttc tccggccgct tgggtggaga ggctattcgg ctatgactgg    2700
gcacaacaga caatcggctg ctctgatgcc gccgtgttcc ggctgtcagc gcaggggcgc    2760
ccggttcttt ttgtcaagac cgacctgtcc ggtgccctga atgaactgca agacgaggca    2820
gcgcggctat cgtggctggc cacgacgggc gttccttgcg cagctgtgct cgacgttgtc    2880
actgaagcgg gaagggactg gctgctattg ggcgaagtgc cggggcagga tctcctgtca    2940
tctcaccttg ctcctgccga gaaagtatcc atcatggctg atgcaatgcg gcggctgcat    3000
acgcttgatc cggctacctg cccattcgac caccaagcga aacatcgcat cgagcgagca    3060
cgtactcgga tggaagccgg tcttgtcgat caggatgatc tggacgaaga gcatcagggg    3120
ctcgcgccag ccgaactgtt cgccaggctc aaggcgagca tgcccgacgg cgaggatctc    3180
gtcgtgaccc atggcgatgc ctgcttgccg aatatcatgg tggaaaatgg ccgcttttct    3240
ggattcatcg actgtggccg ctgggtgtg gcggaccgct atcaggacat agcgttggct      3300
acccgtgata ttgctgaaga gcttggcggc gaatgggctg accgcttcct cgtgctttac    3360
ggtatcgccg ctcccgattc gcagcgcatc gccttctatc gccttcttga cgagttcttc    3420
tgagcgggac tctggggttc gaaatgaccg accaagcgac gcccaacctg ccatcacgag    3480
atttcgattc caccgccgcc ttctatgaaa ggttgggctt cggaatcgtt ttccgggacg    3540
ccggctggat gatcctccag cgcggggatc tcatgctgga gttcttcgcc caccctaggg    3600
ggaggctaac tgaaacacgg aaggagacaa taccggaagg aacccgcgct atgacggcaa    3660 taaaagaca gaataaaacg cacggtgttg ggtcgtttgt tcataaacgc ggggttcggt     3720
cccagggctg gcactctgtc gataccccac cgagaccca ttggggccaa tacgcccgcg      3780
```

```
tttcttcctt ttccccaccc caccccccaa gttcgggtga aggcccaggg ctcgcagcca    3840
acgtcggggc ggcaggccct gccatagcct caggttactc atatatactt tagattgatt    3900
taaaacttca tttttaattt aaaaggatct aggtgaagat cctttttgat aatctcatga    3960
ccaaaatccc ttaacgtgag ttttcgttcc actgagcgtc agaccccgta gaaaagatca    4020
aaggatcttc ttgagatcct ttttttctgc gcgtaatctg ctgcttgcaa acaaaaaaac    4080
caccgctacc agcggtggtt tgtttgccgg atcaagagct accaactctt tttccgaagg    4140
taactggctt cagcagagcg cagataccaa atactgtcct tctagtgtag ccgtagttag    4200
gccaccactt caagaactct gtagcaccgc ctacatacct cgctctgcta atcctgttac    4260
cagtggctgc tgccagtggc gataagtcgt gtcttaccgg gttggactca agacgatagt    4320
taccggataa ggcgcagcgg tcgggctgaa cggggggttc gtgcacacag cccagcttgg    4380
agcgaacgac ctacaccgaa ctgagatacc tacagcgtga gctatgagaa agcgccacgc    4440
ttcccgaagg gagaaaggcg gacaggtatc cggtaagcgg cagggtcgga acaggagagc    4500
gcacgaggga gcttccaggg ggaaacgcct ggtatcttta tagtcctgtc gggtttcgcc    4560
acctctgact tgagcgtcga ttttgtgat gctcgtcagg ggggcggagc ctatggaaaa    4620
acgccagcaa cgcggccttt ttacggttcc tggccttttg ctggccttt gctcacatgt    4680
tctttcctgc gttatccct gattctgtgg ataaccgtat taccgccatg cat           4733
```

<210> SEQ ID NO 17
<211> LENGTH: 6816
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta acaactccgc cccattgacg caaatgggcg gtaggcgtgt     540
acggtgggag gtctatataa gcagagctgg tttagtgaac cgtcagatcc gctagcgcta     600
ccggactcag atctcgagct caagcttcga attctgcagt cgacgccacc atgcaggtga     660
gcaagaggat gctggcgggg ggcgtgagga gcatgcccag ccccctcctg gcctgctggc     720
agcccatcct cctgctggtg ctgggctcag tgctgtcagg ctcggccacg ggctgcccgc     780
cccgctgcga gtgctcgccc caggaccgcg ctgtgctgtg ccaccgcaag cgctttgtgg     840
cagtccccga gggcatcccc accgagacgc gcctgctgga cctaggcaag aaccgcatca     900
aaacgctcaa ccaggacgag ttcgccagct cccgcacct ggaggagctg gagctcaacg     960
agaacatcgt gagcgccgtg gagcccgcg ccttcaacaa cctcttcaac ctccggacgc    1020
tgggtctccg cagcaaccgc ctgaagctca tcccgctagg cgtcttcact ggcctcagca    1080
```

```
acctgaccaa gctggacatc agcgagaaca agatcgttat cctactggac tacatgtttc    1140
aggacctgta caacctcaag tcactggagg ttggcgacaa tgacctcgtc tacatctctc    1200
accgcgcctt cagcggcctc aacagcctgg agcagctgac gctggagaaa tgcaacctga    1260
cctccatccc caccgaggcg ctgtcccacc tgcacggcct catcgtcctg aggctccggc    1320
acctcaacat caatgccatc cgggactact ccttcaagag gctgtaccga ctcaaggtct    1380
tggagatctc ccactggccc tacttggaca ccatgacacc caactgcctc tacggcctca    1440
acctgacgtc cctgtccatc acacactgca atctgaccgc tgtgccctac ctggccgtcc    1500
gccacctagt ctatctccgc ttcctcaacc tctcctacaa ccccatcagc accattgagg    1560
gctccatgtt gcatgagctg ctccggctgc aggagatcca gctggtgggc gggcagctgg    1620
ccgtggtgga gccctatgcc ttccgcggcc tcaactacct cgcgcgtgctc aatgtctctg    1680 gcaaccagct gaccacactg gaggaatcag tcttccactc ggtgggcaac ctggagacac    1740
tcatcctgga ctccaacccg ctggcctgcg actgtcggct cctgtgggtg ttccggcgcc    1800
gctggcggct caacttcaac cggcagcagc ccacgtgcgc cacgcccgag tttgtccagg    1860
gcaaggagtt caaggacttc cctgatgtgc tactgcccaa ctacttcacc tgccgccgcg    1920
cccgcatccg ggaccgcaag gcccagcagg tgtttgtgga cgagggccac acggtgcagt    1980
ttgtgtgccg ggccgatggc gacccgccgc ccgccatcct ctggctctca ccccgaaagc    2040
acctggtctc agccaagagc aatgggcggc tcacagtctt ccctgatggc acgctggagg    2100
tgcgctacgc ccaggtacag acaacggca cgtacctgtg catcgcggcc aacgcgggcg    2160
gcaacgactc catgcccgcc cacctgcatg tgcgcagcta ctcgcccgac tggccccatc    2220
agcccaacaa gaccttcgct ttcatctcca ccagccgggg cgaggagag gccaacagca    2280 cccgcgccac tgtgcctttc cccttcgaca tcaagaccct catcatcgcc accaccatgg    2340
gcttcatctc tttcctgggc gtcgtcctct tctgcctggt gctgctgttt ctctggagcc    2400
ggggcaaggg caacacaaag cacaacatcg agatcgagta tgtgccccga aagtcggacg    2460
caggcatcag ctccgccgac gcgccccgca agttcaacat gaagatgata tcacgggatc    2520
caccggtagc aaccatgacc agcaaggtgt acgaccccga gcagaggaag aggatgatca    2580 ccggcccca gtggtgggcc aggtgcaagc agatgaacgt gctggacagc ttcatcaact    2640
actacgacag cgagaagcac gccgagaacg ccgtgatctt cctgcacggc aacgccgcta    2700
gtagctacct gtggaggcac gtggtgcccc acatcgagcc cgtggccagg tgcatcatcc    2760
ccgatctgat cggcatgggc aagagcggca gagcggcaa cggcagctac aggctgctgg    2820
accactacaa gtacctgacc gcctggttcg agctcctgaa cctgcccaag aagatcatct    2880
tcgtgggcca cgactgggc gcctgcctgg ccttccacta cagctacgag caccaggaca    2940
agatcaaggc catcgtgcac gccgagagcg tggtggacgt gatcgagagc tgggacgagt    3000
ggccagacat cgaggaggac atcgccctga tcaagagcga ggaggcgag aagatggtgc    3060 tggagaacaa cttcttcgtg gagaccatgc tgcccagcaa gatcatgaga aagctggagc    3120
ccgaggagtt cgccgcctac ctggagccct caaggagaa gggcgaggtg agaagaccca    3180
ccctgagctg gcccagagag atccccctgg tgaagggcgg caagcccgac gtggtgcaga    3240
tcgtgagaaa ctacaacgcc tacctgagag ccagcgacga cctgcccaag atgttcatcg    3300
agagcgaccc cggcttcttc agcaacgcca tcgtggaggg cgccaagaag ttccccaaca    3360
ccgagttcgt gaaggtgaag ggcctgcact tcagccagga ggacgccccc gacgagatgg    3420
```

```
gcaagtacat caagagcttc gtggagagag tgctgaagaa cgagcagtaa tgtacaagta    3480
aagcggccgc gactctagat cataatcagc cataccacat ttgtagaggt tttacttgct    3540
ttaaaaaacc tcccacacct cccctgaac ctgaaacata aaatgaatgc aattgttgtt    3600
gttaacttgt ttattgcagc ttataatggt tacaaataaa gcaatagcat cacaaatttc    3660
acaaataaag cattttttc actgcattct agttgtggtt tgtccaaact catcaatgta    3720
tcttaaggcg taaattgtaa gcgttaatat tttgttaaaa ttcgcgttaa attttgtta    3780 aatcagctca ttttttaacc aataggccga atcggcaaa atcccttata atcaaaaga    3840 atagaccgag atagggttga gtgttgttcc agtttggaac aagagtccac tattaaagaa    3900
cgtggactcc aacgtcaaag ggcgaaaaac cgtctatcag ggcgatggcc cactacgtga    3960
accatcaccc taatcaagtt ttttggggtc gaggtgccgt aaagcactaa atcggaaccc    4020 taagggagc ccccgattta gagcttgacg gggaaagccg gcgaacgtgg cgagaaagga    4080
agggaagaaa gcgaaaggag cgggcgctag ggcgctggca agtgtagcgg tcacgctgcg    4140
cgtaaccacc acaccegccg cgcttaatgc gccgctacag ggcgcgtcag gtggcacttt    4200
tcggggaaat gtgcgcggaa cccctatttg tttatttttc taaatacatt caaatatgta    4260
tccgctcatg agacaataac cctgataaat gcttcaataa tattgaaaaa ggaagagtcc    4320
tgaggcggaa agaaccagct gtggaatgtg tgtcagttag ggtgtggaaa gtccccaggc    4380
tccccagcag gcagaagtat gcaaagcatg catctcaatt agtcagcaac caggtgtgga    4440
aagtccccag gctccccagc aggcagaagt atgcaaagca tgcatctcaa ttagtcagca    4500
accatagtcc cgcccctaac tccgcccatc ccgcccctaa ctccgcccag ttccgcccat    4560
tctccgcccc atggctgact aattttttt atttatgcag aggccgaggc cgcctcggcc    4620
tctgagctat tccagaagta gtgaggaggc ttttttggag gcctaggctt ttgcaaagat    4680
cgatcaagag acaggatgag gatcgtttcg catgattgaa caagatggat tgcacgcagg    4740
ttctccggcc gcttgggtgg agaggctatt cggctatgac tgggcacaac agacaatcgg    4800
ctgctctgat gccgccgtgt tccggctgtc agcgcagggg cgcccggttc ttttttgtcaa    4860 gaccgacctg tccggtgccc tgaatgaact gcaagacgag gcagcgcggc tatcgtggct    4920
ggccacgacg ggcgttcctt gcgcagctgt gctcgacgtt gtcactgaag cgggaaggga    4980
ctggctgcta ttgggcgaag tgccggggca ggatctcctg tcatctcacc ttgctcctgc    5040
cgagaaagta tccatcatgg ctgatgcaat gcggcggctg catacgcttg atccggctac    5100
ctgcccattc gaccaccaag cgaaacatcg catcgagcga gcacgtactc ggatggaagc    5160
cggtcttgtc gatcaggatg atctggacga agagcatcag gggctcgcgc cagccgaact    5220
gttcgccagg ctcaaggcga gcatgcccga cggcgaggat ctcgtcgtga cccatggcga    5280
tgcctgcttg ccgaatatca tggtggaaaa tggccgcttt tctggattca tcgactgtgg    5340
ccggctgggt gtggcggacc gctatcagga catagcgttg gctacccgtg atattgctga    5400
agagcttggc ggcgaatggg ctgaccgctt cctcgtgctt tacggtatcg ccgctcccga    5460
ttcgcagcgc atcgccttct atcgccttct tgacgagttc ttctgagcgg gactctgggg    5520
ttcgaaatga ccgaccaagc gacgcccaac ctgccatcac gagatttcga ttccaccgcc    5580
gccttctatg aaaggttggg cttcggaatc gttttccggg acgccggctg atgatcctc    5640 cagcgcgggg atctcatgct ggagttcttc gcccacccta ggggaggct aactgaaaca    5700 cggaaggaga cataccgga aggaacccgc gctatgacgg caataaaaag acagaataaa    5760
acgcacggtg ttgggtcgtt tgttcataaa cgcggggttc ggtcccaggg ctggcactct    5820
```

```
gtcgataccc caccgagacc ccattggggc caatacgccc gcgtttcttc cttttcccca    5880 ccccacccc caagttcggg tgaaggccca gggctcgcag ccaacgtcgg ggcggcaggc     5940
cctgccatag cctcaggtta ctcatatata ctttagattg atttaaaact tcattttttaa    6000 tttaaaagga tctaggtgaa gatccttttt gataatctca tgaccaaaat cccttaacgt    6060
gagttttcgt tccactgagc gtcagacccc gtagaaaaga tcaaaggatc ttcttgagat    6120 ccttttttc tgcgcgtaat ctgctgcttg caaacaaaaa aaccaccgct accagcggtg     6180
gtttgtttgc cggatcaaga gctaccaact cttttccga aggtaactgg cttcagcaga     6240
gcgcagatac caaatactgt ccttctagtg tagccgtagt taggccacca cttcaagaac    6300
tctgtagcac cgcctacata cctcgctctg ctaatcctgt taccagtggc tgctgccagt    6360
ggcgataagt cgtgtcttac cgggttggac tcaagacgat agttaccgga taaggcgcag    6420
cggtcgggct gaacggggg ttcgtgcaca cagcccagct tggagcgaac gacctacacc     6480
gaactgagat acctacagcg tgagctatga gaaagcgcca cgcttcccga agggagaaag    6540
gcggacaggt atccggtaag cggcagggtc ggaacaggag agcgcacgag ggagcttcca    6600
gggggaaacg cctggtatct ttatagtcct gtcgggtttc gccacctctg acttgagcgt    6660
cgatttttgt gatgctcgtc aggggggcgg agcctatgga aaaacgccag caacgcggcc    6720
tttttacggt tcctggcctt ttgctggcct tttgctcaca tgttctttcc tgcgttatcc    6780
cctgattctg tggataaccg tattaccgcc atgcat                              6816

<210> SEQ ID NO 18
<211> LENGTH: 6589
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta caactccgc cccattgacg caaatgggcg gtaggcgtgt    540
acggtgggag gtctatataa gcagagctgg tttagtgaac cgtcagatcc gctagcgcta    600
ccggactcag atctcgagct caagcttcga attctgcagt cgacgccacc atgcaggtga    660
gcaagaggat gctggcgggg ggcgtgagga gcatgcccag cccctcctg gcctgctggc     720 agcccatcct cctgctggtg ctgggctcag tgctgtcagg ctcggccacg ggctgcccgc    780
cccgctgcga gtgctccgcc caggaccgcg ctgtgctgtg ccaccgcaag cgctttgtgg    840
cagtccccga gggcatcccc accgagacgc gcctgctgga cctaggcaag aaccgcatca    900
aaacgctcaa ccaggacgag ttcgccagct tcccgcacct ggaggagctg gagctcaacg    960
agaacatcgt gagcgccgtg gagcccggcg ccttcaacaa cctcttcaac ctccggacgc    1020
```

```
tgggtctccg cagcaaccgc ctgaagctca tcccgctagg cgtcttcact ggcctcagca    1080
acctgaccaa gctggacatc agcgagaaca agatcgttat cctactggac tacatgtttc    1140
aggacctgta caacctcaag tcactggagg ttggcgacaa tgacctcgtc tacatctctc    1200
accgcgcctt cagcggcctc aacagcctgg agcagctgac gctggagaaa tgcaacctga    1260
cctccatccc caccgaggcg ctgtcccacc tgcacggcct catcgtcctg aggctccggc    1320
acctcaacat caatgccatc cgggactact ccttcaagag gctgtaccga ctcaaggtct    1380
tggagatctc ccactggccc tacttggaca ccatgacacc caactgcctc tacggcctca    1440
acctgacgtc cctgtccatc acacactgca atctgaccgc tgtgccctac ctggccgtcc    1500
gccacctagt ctatctccgc ttcctcaacc tctcctacaa ccccatcagc accattgagg    1560
gctccatgtt gcatgagctg ctccggctgc aggagatcca gctggtgggc gggcagctgg    1620
ccgtggtgga gccctatgcc ttccgcggcc tcaactacct gcgcgtgctc aatgtctctg    1680
gcaaccagct gaccacactg gaggaatcag tcttccactc ggtgggcaac ctggagacac    1740
tcatcctgga ctccaacccg ctggcctgcg actgtcggct cctgtgggtg ttccggcgcc    1800
gctggcggct caacttcaac cggcagcagc ccacgtgcgc cacgcccgag tttgtccagg    1860
gcaaggagtt caaggacttc cctgatgtgc tactgcccaa ctacttcacc tgccgccgcg    1920
cccgcatccg ggaccgcaag gcccagcagg tgtttgtgga cgagggccac acggtgcagt    1980
ttgtgtgccg ggccgatggc gacccgccgc ccgccatcct ctggctctca ccccgaaagc    2040
acctggtctc agccaagagc aatgggcggc tcacagtctt ccctgatggc acgctggagg    2100
tgcgctacgc ccaggtacag gacaacggca cgtacctgtg catcgcggcc aacgcgggcg    2160
gcaacgactc catgcccgcc cacctgcatg tgcgcagcta ctcgcccgac tggccccatc    2220
agcccaacaa gaccttcgct ttcatctcca accagccggg cgagggagag gccaacagca    2280
cccgcgccac tgtgccttt cccttcgaca tcaagaccct catcatcgcc accaccatgg    2340
gcttcatctc tttcctgggc gtcgtcctct tctgcctggt gctgctgttt ctctggagcc    2400
ggggcaaggg caaacaaaag cacaacatcg agatcgagta tgtgccccga agtcggacg    2460
caggcatcag ctccgccgac gcgccccgca agttcaacat gaagatgata tcacgggatc    2520
caccggtcgc caccatggtg agcaagggcg aggagctgtt caccggggtg gtgcccatcc    2580
tggtcgagct ggacggcgac gtaaacggcc acaagttcag cgtgtccggc gagggcgagg    2640
gcgatgccac ctacggcaag ctgaccctga agttcatctg caccaccggc aagctgcccg    2700
tgccctggcc caccctcgtg accaccttcg gctacggcct gcagtgcttc gcccgctacc    2760
ccgaccacat gaagcagcac gacttcttca gtccgccat gcccgaaggc tacgtccagg    2820
agcgcaccat cttcttcaag gacgacggca actacaagac ccgcgccgag gtgaagttcg    2880
agggcgacac cctggtgaac cgcatcgagc tgaagggcat cgacttcaag gaggacggca    2940
acatcctggg gcacaagctg gagtacaact acaacagcca caacgtctat atcatggccg    3000
acaagcagaa gaacggcatc aaggtgaact tcaagatccg ccacaacatc gaggacggca    3060
gcgtgcagct cgccgaccac taccagcaga cacccccat cggcgacggc ccgtgctgc    3120
tgcccgacaa ccactacctg agctaccagt ccgccctgag caaagacccc aacgagaagc    3180
gcgatcacat ggtcctgctg gagttcgtga ccgccgccgg gatcactctc ggcatggacg    3240
agctgtacaa gtaaagcggc cgcgactcta gatcataatc agccatacca catttgtaga    3300
ggttttactt gctttaaaaa acctcccaca cctccccctg aacctgaaac ataaaatgaa    3360
```

```
tgcaattgtt gttgttaact tgtttattgc agcttataat ggttacaaat aaagcaatag    3420
catcacaaat ttcacaaata aagcattttt ttcactgcat tctagttgtg gtttgtccaa    3480
actcatcaat gtatcttaag gcgtaaattg taagcgttaa tattttgtta aaattcgcgt    3540 taaattttg ttaaatcagc tcatttttta accaataggc cgaaatcggc aaaatccctt     3600
ataaatcaaa agaatagacc gagatagggt tgagtgttgt tccagtttgg aacaagagtc    3660
cactattaaa gaacgtggac tccaacgtca aagggcgaaa aaccgtctat cagggcgatg    3720
gcccactacg tgaaccatca ccctaatcaa gttttttggg gtcgaggtgc cgtaaagcac    3780
taaatcggaa ccctaaaggg agccccgat ttagagcttg acggggaaag ccggcgaacg     3840
tggcgagaaa ggaagggaag aaagcgaaag gagcgggcgc tagggcgctg gcaagtgtag    3900
cggtcacgct gcgcgtaacc accacacccg ccgcgcttaa tgcgccgcta cagggcgcgt    3960
caggtggcac ttttcgggga aatgtgcgcg gaacccctat ttgtttattt ttctaaatac    4020
attcaaatat gtatccgctc atgagacaat aaccctgata aatgcttcaa taatattgaa    4080
aaaggaagag tcctgaggcg gaaagaacca gctgtgtgaat gtgtgtcagt tagggtgtgg    4140
aaagtcccca ggctccccag caggcagaag tatgcaaagc atgcatctca attagtcagc    4200
aaccaggtgt ggaaagtccc caggctcccc agcaggcaga agtatgcaaa gcatgcatct    4260
caattagtca gcaaccatag tcccgcccct aactccgccc atcccgcccc taactccgcc    4320
cagttccgcc cattctccgc cccatggctg actaattttt tttatttatg cagaggccga    4380
ggccgcctcg gcctctgagc tattccagaa gtagtgagga ggcttttttg gaggcctagg    4440
cttttgcaaa gatcgatcaa gagacaggat gaggatcgtt tcgcatgatt gaacaagatg    4500
gattgcacgc aggttctccg gccgcttggg tggagaggct attcggctat gactgggcac    4560
aacagacaat cggctgctct gatgccgccg tgttccggct gtcagcgcag gggcgcccgg    4620 ttcttttgt caagaccgac ctgtccggtg ccctgaatga actgcaagac gaggcagcgc     4680
ggctatcgtg gctggccacg acgggcgttc cttgcgcagc tgtgctcgac gttgtcactg    4740
aagcgggaag ggactggctg ctattgggcg aagtgccggg gcaggatctc ctgtcatctc    4800
accttgctcc tgccgagaaa gtatccatca tggctgatgc aatgcggcgg ctgcatacgc    4860
ttgatccggc tacctgccca ttcgaccacc aagcgaaaca tcgcatcgag cgagcacgta    4920
ctcggatgga agccggtctt gtcgatcagg atgatctgga cgaagagcat caggggctcg    4980
cgccagccga actgttcgcc aggctcaagg cgagcatgcc cgacggcgag gatctcgtcg    5040
tgacccatgg cgatgcctgc ttgccgaata tcatggtgga aaatggccgc ttttctggat    5100
tcatcgactg tggccggctg ggtgtggcgg accgctatca ggacatagcg ttggctaccc    5160
gtgatattgc tgaagagctt ggcggcgaat gggctgaccg cttcctcgtg ctttacggta    5220
tcgccgctcc cgattcgcag cgcatcgcct tctatcgcct tcttgacgag ttcttctgag    5280
cgggactctg gggttcgaaa tgaccgacca agcgacgccc aacctgccat cacgagattt    5340
cgattccacc gccgccttct atgaaaggtt gggcttcgga atcgttttcc gggacgccgg    5400
ctggatgatc ctccagcgcg gggatctcat gctggagttc ttcgcccacc ctaggggag     5460 gctaactgaa acacggaagg agacaatacc ggaaggaacc cgcgctatga cggcaataaa    5520
aagacagaat aaaacgcacg tgttgggtc gtttgttcat aaacgcgggg ttcggtccca     5580
gggctggcac tctgtcgata ccccaccgag accccattgg ggccaatacg cccgcgtttc    5640 ttcctttcc ccaccccacc ccccaagttc gggtgaaggc ccagggctcg cagccaacgt     5700
cggggcggca ggccctgcca tagcctcagg ttactcatat atactttaga ttgatttaaa    5760
```

| | |
|---|---|
| acttcatttt taatttaaaa ggatctaggt gaagatcctt tttgataatc tcatgaccaa | 5820 |
| aatcccttaa cgtgagtttt cgttccactg agcgtcagac cccgtagaaa agatcaaagg | 5880 |
| atcttcttga gatccttttt ttctgcgcgt aatctgctgc ttgcaaacaa aaaaaccacc | 5940 |
| gctaccagcg gtggtttgtt tgccggatca agagctacca actcttttc cgaaggtaac | 6000 |
| tggcttcagc agagcgcaga taccaaatac tgtccttcta gtgtagccgt agttaggcca | 6060 |
| ccacttcaag aactctgtag caccgcctac atacctcgct ctgctaatcc tgttaccagt | 6120 |
| ggctgctgcc agtggcgata agtcgtgtct taccgggttg gactcaagac gatagttacc | 6180 |
| ggataaggcg cagcggtcgg gctgaacggg gggttcgtgc acacagccca gcttggagcg | 6240 |
| aacgacctac accgaactga gatacctaca gcgtgagcta tgagaaagcg ccacgcttcc | 6300 |
| cgaagggaga aaggcggaca ggtatccggt aagcggcagg gtcggaacag gagagcgcac | 6360 |
| gagggagctt ccagggggaa acgcctggta tctttatagt cctgtcgggt ttcgccacct | 6420 |
| ctgacttgag cgtcgatttt tgtgatgctc gtcaggggg cggagcctat ggaaaaacgc | 6480 |
| cagcaacgcg gccttttac ggttcctggc cttttgctgg ccttttgctc acatgttctt | 6540 |
| tcctgcgtta tccctgatt ctgtggataa ccgtattacc gccatgcat | 6589 |

<210> SEQ ID NO 19
<211> LENGTH: 7311
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

| | |
|---|---|
| gacggatcgg gagatctccc gatccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca tgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggacttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta caaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gcttgccacc | 900 |
| atgcaggtga gcaagaggat gctggcgggg gcgtgagga gcatgcccag cccctcctg | 960 |
| gcctgctggc agcccatcct cctgctggtg ctgggctcag tgctgtcagg ctcggccacg | 1020 |
| ggctgcccgc ccgctgcga gtgctccgcc caggaccgcg ctgtgctgtg ccaccgcaag | 1080 |
| cgctttgtgg cagtccccga gggcatcccc accgagacgc gctgctgga cctaggcaag | 1140 |
| aaccgcatca aaacgctcaa ccaggacgag ttcgccagct tcccgcacct ggaggagctg | 1200 |

```
gagctcaacg agaacatcgt gagcgccgtg gagcccggcg ccttcaacaa cctcttcaac    1260
ctccggacgc tgggtctccg cagcaaccgc ctgaagctca tcccgctagg cgtcttcact    1320
ggcctcagca acctgaccaa gctggacatc agcgagaaca agatcgttat cctactggac    1380
tacatgtttc aggacctgta caacctcaag tcactggagg ttggcgacaa tgacctcgtc    1440
tacatctctc accgcgcctt cagcggcctc aacagcctgg agcagctgac gctggagaaa    1500
tgcaacctga cctccatccc caccgaggcg ctgtcccacc tgcacggcct catcgtcctg    1560
aggctccggc acctcaacat caatgccatc cgggactact ccttcaagag gctgtaccga    1620
ctcaaggtct ggagatctc ccactggccc tacttggaca ccatgacacc caactgcctc    1680
tacggcctca acctgacgtc cctgtccatc acacactgca atctgaccgc tgtgccctac    1740
ctggccgtcc gccacctagt ctatctccgc ttcctcaacc tctcctacaa ccccatcagc    1800
accattgagg ctccatgtt gcatgagctg ctccggctgc aggagatcca gctggtgggc    1860
gggcagctgg ccgtggtgga gcctatgcc ttccgcggcc tcaactacct gcgcgtgctc    1920
aatgtctctg caaccagct gaccacactg aggaatcag tcttccactc ggtgggcaac    1980
ctggagacac tcatcctgga ctccaacccg ctggcctgcg actgtcggct cctgtgggtg    2040
ttccggcgcc gctggcggct caacttcaac cggcagcagc ccacgtgcgc cacgcccgag    2100
tttgtccagg caaggagtt caaggacttc cctgatgtgc tactgcccaa ctacttcacc    2160
tgccgccgcg cccgcatccg ggaccgcaag gcccagcagg tgtttgtgga cgagggccac    2220
acggtgcagt ttgtgtgccg ggccgatggc gacccgccgc ccgccatcct ctggctctca    2280
ccccgaaagc acctggtctc agccaagagc aatgggcggc tcacagtctt ccctgatggc    2340
acgctggagg tgcgctacgc ccaggtacag gacaacggca cgtacctgtg catcgcggcc    2400
aacgcgggcg gcaacgactc catgcccgcc cacctgcatg tgcgcagcta ctcgcccgac    2460
tggccccatc agcccaacaa gaccttcgct ttcatctcca accagccggg cgagggagag    2520
gccaacagca cccgcgccac tgtgcctttc cccttcgaca tcaagaccct catcatcgcc    2580
accaccatgg gcttcatctc ttttcctggg gtcgtcctct tctgcctggt gctgctgttt    2640
ctctggagcc ggggcaaggg caacacaaag cacaacatcg agatcgagta tgtgccccga    2700
aagtcggacg caggcatcag ctccgccgac gcgccccgca gttcaacat gaagatgata    2760 ggatccgcta gctatccata tgatgttcct gattatgctt gagaattctg cagatatcca    2820
tcacactggc ggccgctcga gcatgcatct agagggccct attctatagt gtcacctaaa    2880
tgctagagct cgctgatcag cctcgactgt gccttctagt tgccagccat ctgttgtttg    2940
cccctccccc gtgccttcct tgaccctgga aggtgccact cccactgtcc tttcctaata    3000
aaatgaggaa attgcatcgc attgtctgag taggtgtcat tctattctgg ggggtggggt    3060
ggggcaggac agcaaggggg aggattggga agacaatagc aggcatgctg gggatgcggt    3120
gggctctatg gcttctgagg cggaaagaac cagctgggc tctaggggt atccccacgc    3180 gccctgtagc ggcgcattaa gcgcggcggg tgtggtggtt acgcgcagcg tgaccgctac    3240
acttgccagc gccctagcgc ccgctccttt cgctttcttc ccttcctttc tcgccacgtt    3300
cgccggcttt ccccgtcaag ctctaaatcg gggcatccct ttagggttcc gatttagtgc    3360
tttacggcac ctcgacccca aaaaacttga ttagggtgat ggttcacgta gtgggccatc    3420
gccctgatag acggtttttc gccctttgac gttggagtcc acgttcttta atagtggact    3480
cttgttccaa actggaacaa cactcaaccc tatctcggtc tattcttttg atttataagg    3540
```

```
gattttgggg atttcggcct attggttaaa aaatgagctg atttaacaaa aatttaacgc    3600
gaattaattc tgtggaatgt gtgtcagtta gggtgtggaa agtccccagg ctccccaggc    3660
aggcagaagt atgcaaagca tgcatctcaa ttagtcagca accaggtgtg gaaagtcccc    3720
aggctcccca gcaggcagaa gtatgcaaag catgcatctc aattagtcag caaccatagt    3780 cccgcccta actccgccca tcccgcccct aactccgccc agttccgccc attctccgcc    3840
ccatggctga ctaattttt tatttatgc agaggccgag gccgcctctg cctctgagct    3900
attccagaag tagtgaggag gcttttttgg aggcctaggc ttttgcaaaa agctcccggg    3960
agcttgtata tccattttcg gatctgatca agagacagga tgaggatcgt ttcgcatgat    4020
tgaacaagat ggattgcacg caggttctcc ggccgcttgg gtggagaggc tattcggcta    4080
tgactgggca caacagacaa tcggctgctc tgatgccgcc gtgttccggc tgtcagcgca    4140
ggggcgcccg gttcttttg tcaagaccga cctgtccggt gccctgaatg aactgcagga    4200
cgaggcagcg cggctatcgt ggctggccac gacgggcgtt ccttgcgcag ctgtgctcga    4260
cgttgtcact gaagcgggaa gggactggct gctattgggc gaagtgccgg gcaggatct    4320 cctgtcatct caccttgctc ctgccgagaa agtatccatc atggctgatg caatgcggcg    4380
gctgcatacg cttgatccgg ctacctgccc attcgaccac caagcgaaac atcgcatcga    4440
gcgagcacgt actcggatgg aagccggtct tgtcgatcag gatgatctgg acgaagagca    4500 tcagggctc gcgccagccg aactgttcgc caggctcaag gcgcgcatgc ccgacggcga    4560
ggatctcgtc gtgacccatg gcgatgcctg cttgccgaat atcatggtgg aaaatggccg    4620 ctttctgga ttcatcgact gtggccggct gggtgtggcg accgctatc aggacatagc    4680 gttggctacc cgtgatattg ctgaagagct tggcggcgaa tgggctgacc gcttcctcgt    4740
gctttacggt atcgccgctc ccgattcgca gcgcatcgcc ttctatcgcc ttcttgacga    4800
gttcttctga gcgggactct ggggttcgaa atgaccgacc aagcgacgcc caacctgcca    4860
tcacgagatt tcgattccac cgccgccttc tatgaaaggt tgggcttcgg aatcgttttc    4920
cgggacgccg gctggatgat cctccagcgc ggggatctca tgctggagtt cttcgcccac    4980
cccaacttgt ttattgcagc ttataatggt tacaaataaa gcaatagcat cacaaatttc    5040
acaaataaag catttttttc actgcattct agttgtggtt tgtccaaact catcaatgta    5100
tcttatcatg tctgtatacc gtcgacctct agctagagct tggcgtaatc atggtcatag    5160
ctgtttcctg tgtgaaattg ttatccgctc acaattccac acaacatacg agccggaagc    5220
ataaagtgta aagcctgggg tgcctaatga gtgagctaac tcacattaat tgcgttgcgc    5280
tcactgcccg ctttccagtc gggaaacctg tcgtgccagc tgcattaatg aatcggccaa    5340
cgcgcgggga gaggcggttt gcgtattggg cgctcttccg cttcctcgct cactgactcg    5400
ctgcgctcgg tcgttcggct gcggcgagcg gtatcagctc actcaaaggc ggtaatacgg    5460
ttatccacag aatcagggga taacgcagga aagaacatgt gagcaaaagg ccagcaaaag    5520
gccaggaacc gtaaaaaggc cgcgttgctg gcgtttttcc ataggctccg ccccctgac    5580 gagcatcaca aaaatcgacg ctcaagtcag aggtggcgaa acccgacagg actataaaga    5640
taccaggcgt ttccccctgg aagctccctc gtgcgctctc ctgttccgac cctgccgctt    5700
accggatacc tgtccgcctt tctcccttcg ggaagcgtgg cgctttctca atgctcacgc    5760
tgtaggtatc tcagttcggt gtaggtcgtt cgctccaagc tgggctgtgt gcacgaaccc    5820
cccgttcagc ccgaccgctg cgccttatcc ggtaactatc gtcttgagtc aacccggta    5880 agacacgact tatcgccact ggcagcagcc actggtaaca ggattagcag agcgaggtat    5940
```

```
gtaggcggtg ctacagagtt cttgaagtgg tggcctaact acggctacac tagaaggaca    6000
gtatttggta tctgcgctct gctgaagcca gttaccttcg gaaaaagagt tggtagctct    6060
tgatccggca aacaaaccac cgctggtagc ggtggttttt ttgtttgcaa gcagcagatt    6120
acgcgcagaa aaaaggatc tcaagaagat cctttgatct tttctacggg gtctgacgct     6180
cagtggaacg aaaactcacg ttaagggatt ttggtcatga gattatcaaa aaggatcttc    6240
acctagatcc ttttaaatta aaaatgaagt tttaaatcaa tctaaagtat atatgagtaa    6300
acttggtctg acagttacca atgcttaatc agtgaggcac ctatctcagc gatctgtcta    6360
tttcgttcat ccatagttgc ctgactcccc gtcgtgtaga taactacgat acgggagggc    6420
ttaccatctg gccccagtgc tgcaatgata ccgcgagacc cacgctcacc ggctccagat    6480
ttatcagcaa taaccagcc agccggaagg gccgagcgca gaagtggtcc tgcaacttta     6540
tccgcctcca tccagtctat taattgttgc cgggaagcta gagtaagtag ttcgccagtt    6600
aatagtttgc gcaacgttgt tgccattgct acaggcatcg tggtgtcacg ctcgtcgttt    6660
ggtatggctt cattcagctc cggttcccaa cgatcaaggc gagttacatg atccccatg     6720 ttgtgcaaaa aagcggttag ctccttcggt cctccgatcg ttgtcagaag taagttggcc    6780
gcagtgttat cactcatggt tatggcagca ctgcataatt ctcttactgt catgccatcc    6840
gtaagatgct tttctgtgac tggtgagtac tcaaccaagt cattctgaga atagtgtatg    6900
cggcgaccga gttgctcttg cccggcgtca atacgggata ataccgcgcc acatagcaga    6960
actttaaaag tgctcatcat tggaaaacgt tcttcggggc gaaaactctc aaggatctta    7020
ccgctgttga gatccagttc gatgtaaccc actcgtgcac ccaactgatc ttcagcatct    7080
tttactttca ccagcgtttc tgggtgagca aaaacaggaa ggcaaaatgc cgcaaaaaag    7140
ggaataaggg cgacacggaa atgttgaata ctcatactct tcctttttca atattattga    7200
agcatttatc agggttattg tctcatgagc ggatacatat ttgaatgtat ttagaaaaat    7260
aaacaaatag gggttccgcg cacatttccc cgaaaagtgc cacctgacgt c             7311
```

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cgtcgccgtc cagctcgacc ag                                              22